United States Patent
Li et al.

(10) Patent No.: US 12,111,322 B2
(45) Date of Patent: Oct. 8, 2024

(54) MASS SPECTROMETRY-BASED METHOD FOR SIMULTANEOUS QUALITATIVE AND QUANTITATIVE PROTEIN CITRULLINATION ANALYSIS OF COMPLEX BIOLOGICAL SAMPLES

(71) Applicant: Wisconsin Alumni Research Foundation, Madison, WI (US)

(72) Inventors: Lingjun Li, Madison, WI (US); Yatao Shi, Arlington, MA (US); Zihui Li, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 605 days.

(21) Appl. No.: 17/121,242

(22) Filed: Dec. 14, 2020

(65) Prior Publication Data
US 2021/0181206 A1 Jun. 17, 2021

Related U.S. Application Data

(60) Provisional application No. 62/947,850, filed on Dec. 13, 2019.

(51) Int. Cl.
*G01N 33/68* (2006.01)

(52) U.S. Cl.
CPC ..... *G01N 33/6848* (2013.01); *G01N 2440/18* (2013.01); *G01N 2458/15* (2013.01)

(58) Field of Classification Search
CPC ........... G01N 2440/18; G01N 33/6848; G01N 33/6851; G01N 2458/15
See application file for complete search history.

(56) References Cited

U.S. PATENT DOCUMENTS

| | | | |
|---|---|---|---|
| 9,388,132 B2 | 7/2016 | Li et al. | |
| 10,119,974 B2 | 11/2018 | Li et al. | |
| 11,408,897 B2 | 8/2022 | Li et al. | |
| 11,535,576 B2 | 12/2022 | Li et al. | |
| 2011/0165606 A1* | 7/2011 | Tutturen | G01N 33/6842 548/304.1 |
| 2016/0258961 A1* | 9/2016 | Thompson | G01N 33/6893 |
| 2018/0299464 A1 | 10/2018 | Li et al. | |

(Continued)

OTHER PUBLICATIONS

Goshe, M.B. et al. "Phosphoprotein Isotope-Coded Affinity Tag Approach for Isolating and Quantitating Phosphopeptides in Proteome-Wide Analyses," Anal. Chem. 2001, 73, 2578-2586 (Year: 2001).*

(Continued)

*Primary Examiner* — Jennifer Wecker
*Assistant Examiner* — Michelle Adams
(74) *Attorney, Agent, or Firm* — Leydig, Voit & Mayer, Ltd.

(57) ABSTRACT

The present invention discloses mass spectrometry (MS)-based methods and tagging reagents for qualitative and quantitative analysis of post-translational modified (PTM) proteins in biological and clinical samples. The present invention utilizes thiol-containing tagging reagents which are able to bind to or derivatize biomolecules, preferably post-translational modified (PTM) polypeptides such as citrullinated and homocitrullinated polypeptides. The tagging reagents are preferably biotin-derived tags able to react with a side chain of the modified polypeptides.

14 Claims, 45 Drawing Sheets

Specification includes a Sequence Listing.

(56) References Cited

U.S. PATENT DOCUMENTS

2019/0225559 A1 7/2019 Li et al.

OTHER PUBLICATIONS

Murray, C.I. et al. (2012) "Identification and Quantification of S-Nitrosylation by Cysteine Reactive Tandem Mass Tag Switch Assay," Mol. Cell. Proteomics 11(2): M111.013441 (Year: 2012).*
Clancy, K.W. et al. "Detection and identification of protein citrullination in complex biological systems," Current Opinion in Chemical Biology 2016, 30:1-6. (Year: 2016).*
Noort, D. et al. "Verification of Exposure to Organophosphates: Generic Mass Spectrometric Method for Detection of Human Butyrylcholinesterase Adducts," Anal. Chem. 2006, 78, 18, 6640-6644 (Year: 2006).*
Paige, J.S. et al. "Nitrosothiol Reactivity Profiling Identifies S-Nitrosylated Proteins with Unexpected Stability," Chemistry & Biology 15, 1307-1316, 2008 (Year: 2008).*
Bicker et al. (2012) "Seeing Citrulline: Development of a Phenylglyoxal-Based Probe To Visualize Protein Citrullination" J. Am. Chem. Soc. 134(41): pp. 17015-17018.
Boersema et al. (2009) "Multiplex peptide stable isotope dimethyl labeling for quantitative proteomics" Nat Protoc. 4(4): pp. 484-494.
Dwivedi et al. (2017) "Citrullination and Neutrophil Extracellular Traps" Protein Deimination in Human Health and Disease, pp. 137-159.
Elkon, Keith B. (2013) "Poking Holes in Rheumatoid Joints" Sci. Transl. Med 5(2019) pp. 209fs39.

Fert-Bober et al. (2015) "Citrullination of myofilament proteins in heart failure" Cardiovascular Research 108(2): pp. 232-242.
Fert-Bober et al. (2019) "Mapping Citrullinated Sites in Multiple Organs of Mice Using Hypercitrullinated Library" J Proteome Res. 18(5): pp. 2270-2278.
Frost et al. (2015) "High-Resolution Enabled 12-Plex DiLeu Isobaric Tags for Quantitative Proteomics" Anal. Chem., 87(3): pp. 1646-1654.
Frost et al. (2017) "Mass Defect-Based Dimethyl Pyrimidinyl Ornithine (DiPyrO) Tags for Multiplex Quantitative Proteomics" Anal. Chem., 89(20): pp. 10798-10805.
Frost et al. (May 2020) "21-plex DiLeu Isobaric Tags for High-Throughput Quantitative Proteomics" Anal. Chem. 92(12): pp. 8228-8234.
Holm et al. (2006) "Specific modification of peptide-bound citrulline residues" Anal Biochem. 352(1): pp. 68-76.
Ishigami et al. (2005) "Abnormal accumulation of citrullinated proteins catalyzed by peptidylarginine deiminase in hippocampal extracts from patients with Alzheimer's disease" Journal of Neuroscience Research 80(1): pp. 120-128.
Kunieda et al. (2018) "Development of a fluorescent probe for detection of citrulline based on photo-induced electron transfer" Bioorg Med Chem Lett, 28(5): pp. 969-973.
Tutturen et al. (2014) "Assessing the Citrullinome in Rheumatoid Arthritis Synovial Fluid with and without Enrichment of Citrullinated Peptides" J. Proteome Res. 13(6): pp. 2867-2873.
Wang et al. (2017) "PADI2-Mediated Citrullination Promotes Prostate Cancer Progression" Cancer Research 77(21): pp. 5755-5768.
Takakashi (1968) "The Reaction of Phenylglyoxal with Arginine Residues in Proteins," The Journal of Biological Chemistry 243(23): pp. 6171-6179.

* cited by examiner

Dimethyl labeling

DiPyrO

DiLeu

TMT

1) Thiol-containing biotin tag without cleavable groups

The simplest thiol-containing biotin tag

Examples of R group:

2) Protected thiol-containing biotin tag without cleavable groups

Protected by disulfide bond

Protected by pyridyl disulfide bond a b (i) Full MS m/z= 448.2528-448.2618; +3     (ii) Full MS m/z=448.2525-448.2615; +3

(iii) Full MS m/z=696.8809-696.8949; +2    (iv) Full MS m/z=565.9593-565.9707; +3

MASS SPECTROMETRY-BASED METHOD FOR SIMULTANEOUS QUALITATIVE AND QUANTITATIVE PROTEIN CITRULLINATION ANALYSIS OF COMPLEX BIOLOGICAL SAMPLES

CROSS-REFERENCE TO RELATED APPLICATIONS

This application claims priority from U.S. Provisional Patent Application No. 62/947,850 filed Dec. 13, 2019, which is incorporated by reference herein to the extent that there is no inconsistency with the present disclosure.

STATEMENT REGARDING FEDERALLY SPONSORED RESEARCH OR DEVELOPMENT

This invention was made with government support under AG060242 awarded by the National Institutes of Health. The government has certain rights in the invention.

BACKGROUND OF THE INVENTION

Post-translational modifications (PTMs) represent the biochemical modifications of proteins following ribosomal translation to form the mature protein, which could be induced by the cleavage of peptide bonds, the formation of disulfide bonds, the modification of existing functional groups and the addition of new functional groups. Examples of PTMs include, but are not limited to, acetylation, amidation, citrullination, glycosylation, lipidation, methylation, nitrosylation, phosphorylation, proteolysis, and ubiquitination.

PTMs play an important role in the regulation of protein folding and translocation, protein-protein interactions as well as the protein physiological functions. It has been revealed that abnormal alteration of many protein PTMs are associated with the onset and progress of many devastating diseases. Hence, comprehensive and systematic profiling of the dynamic changes of disease-related protein PTMs is not only critical to unravel the pathogenesis of diseases, but beneficial to the diagnosis and treatment of diseases in clinic.

Protein citrullination is initially known as a protein PTM involved in rheumatoid arthritis and multiple sclerosis. Recently, more evidence also suggests that it is involved in many serious diseases, including Alzheimer's disease, cardiovascular disease, and cancers. However, the current understanding about this PTM is still rather limited and impeded, primarily due to the lack of effective analytical methods for the large-scale analysis of citrullinated proteins in complex biological samples.

Current citrullination studies mainly rely on conventional antibody-based techniques such as enzyme-linked immunosorbent assay (ELISA), immunohistochemistry (IHC) and Western blotting (WB). However, current antibodies either target a specific citrullinated protein or are applied to general protein citrullination analysis. Precise and high throughput identification of low-abundance citrullinated proteins in complex biological samples is still not achievable. In addition, information in terms of protein citrullination localization cannot be revealed by these antibody-based detection methods.

In recent years, mass spectrometry (MS)-based bottom-up proteomics has been proven to be a useful tool for large-scale-analysis of many important PTMs, such as protein phosphorylation, methylation and glycosylation. However, its application to protein citrullination analysis suffers from several challenges including: i) methods enabling specific capture of citrullinated peptides for MS analysis are not effective; and ii) the mass shift of 0.984 Da induced by citrullination is the same as that of another modification called deamidation. Furthermore, $^{13}C$ isotopic peaks in tandem MS spectra have a mass shift of 1.0033 Da, which is close to that of citrullination. These will interfere with the accurate annotation of peptide fragment ions upon automated MS data processing, leading to misidentification of citrullination sites.

To address these challenges, various analytical strategies, such as chemical derivatization and biotin tag-assisted enrichment, have been employed, but no methods have so far simultaneously overcome the above challenges that allow successful application to complex biological sample analysis. For example, a biotin tag designed for MS-based large-scale citrullination analysis has been reported but has several drawbacks including: a) the tag imparts a mass shift of +516.2 Da per tag to labeled peptides, which negatively affects the solubility, chromatographic separation and ionization efficiency of labeled peptides, and b) the biotin tag itself has multiple fragmentation sites, resulting in a large amount of tag-derived fragment ions in MS/MS spectra. The fragmentation of this tag itself greatly suppresses the peptide backbone fragmentation and therefore significantly reduces the quality of peptide MS/MS spectra, leading to fewer numbers of citrullinated protein identifications.

In the present invention, novel thiol and thioether-containing biotin tags are described for the specific chemical derivatization of any biomolecule containing an ureido group or similar functional group. Furthermore, a novel method is described below, which integrates chemical derivatization and biotin tag-assisted enrichment strategy with mass spectrometry (MS)-based technology, for the large-scale and high-confident identification of citrullinated proteins from biological samples. In addition, it is demonstrated that the novel method can be combined with multiple MS-based quantitative strategies, including isotopic and isobaric tag labeling techniques, enabling the concurrently qualitative and quantitative analysis of citrullinated proteins from various biological samples.

SUMMARY OF THE INVENTION

The present invention discloses mass spectrometry (MS)-based methods and tagging reagents for qualitative and quantitative analysis of biological and clinical samples. The present invention utilizes thiol (SH) and thioether ($R^1$—S—$R^2$) containing tagging reagents that are able to bind to or derivatize biomolecules, preferably polypeptides having one or more post-translational modifications (PTMs).

In an embodiment, the methods and tagging reagents are suitable for any molecule able to react to the thiol-containing or thioether-containing tagging reagent. Preferably, the molecule is a polypeptide, especially a polypeptide which has undergone post-translational modification. In an embodiment, the present methods and tagging reagents are suitable for use with polypeptides having PTMs that include, but are not limited to, acetylation, acylation, alkylation, amidation, carbamylation, citrullination, glycosylation, hydroxylation, iodination, lipidation, methionine oxidation, methylation, nitrosylation, phosphorylation, prenylation, sulfonation, neddylation, SUMOylation, and ubiquitination. In an embodiment, the polypeptides are citrullinated polypeptides.

In an embodiment, the present invention provides a method for the analysis of a target biomolecule and/or for the large-scale profiling of target biomolecules in samples, said method comprising the steps of: a) providing a sample containing the target biomolecule; b) reacting the target biomolecule with a tagging reagent to generate a labeled biomolecule, wherein the tagging reagent comprises a thiol group or thioether group which reacts with a functional group of the target biomolecule, and wherein reacting the tagging reagent with the target biomolecule imparts a mass shift to the target biomolecule; c) ionizing the labeled biomolecule to form a precursor ion; and d) detecting and analyzing the precursor ion using a mass spectrometer. Additionally, the precursor ions may be fragmented to form one or more fragment ions, where the fragment ions are detected and analyzed in MS$^2$ mass spectrometry. The method optionally comprises the step of: e) identifying biomolecules with mass spectrometry data, where the identification is performed manually and/or automatically.

In an embodiment, the tagging reagent comprises a tag having the formula:

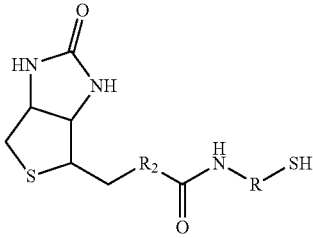

wherein R is selected from the group consisting of substituted and unsubstituted $C_1$ to $C_{24}$ alkyl groups, $C_1$ to $C_{24}$ cycloalkyl groups, $C_1$ to $C_{24}$ alkenyl groups, $C_1$ to $C_{24}$ cycloalkenyl groups, $C_4$ to $C_{24}$ aryl groups and $C_4$ to $C_{24}$ arylalkyl groups; and $R_2$ is selected from the group consisting of substituted and unsubstituted $C_1$ to $C_{10}$ alkyl groups and $C_1$ to $C_{10}$ alkenyl groups. Preferably, $R_2$ is selected from the group consisting of substituted and unsubstituted $C_1$ to $C_6$ alkyl groups and $C_1$ to $C_6$ alkenyl groups.

In an embodiment, the tagging reagent comprises a tag having the formula:

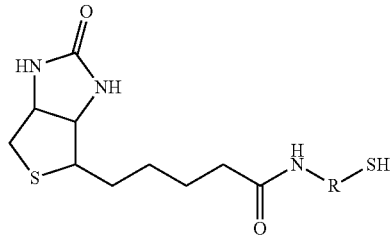

wherein R is selected from the group consisting of substituted and unsubstituted $C_1$ to $C_{24}$ alkyl groups, $C_1$ to $C_{24}$ cycloalkyl groups, $C_1$ to $C_{24}$ alkenyl groups, $C_1$ to $C_{24}$ cycloalkenyl groups, $C_4$ to $C_{24}$ aryl groups and $C_4$ to $C_{24}$ arylalkyl groups.

Optionally, R in the above formulas is selected from the group consisting of substituted and unsubstituted $C_1$ to $C_{12}$ alkyl groups, $C_1$ to $C_{12}$ cycloalkyl groups, $C_1$ to $C_{12}$ alkenyl groups, $C_1$ to $C_{12}$ cycloalkenyl groups, $C_4$ to $C_{12}$ aryl groups and $C_4$ to $C_{12}$ arylalkyl groups. In an embodiment, R is:

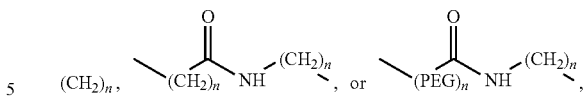

where n is an integer from 1 to 12, preferably from 1 to 6, from 1 to 4, or from 1 to 2.

The tagging reagent may comprise one or more cleavable groups, which are able to be cleaved prior to the ionizing step by methods known in the art, such as by the use of a reducing agent, strong acid, hydrazine, sodium dithionite, trypsin/lysine, or ultraviolet light. In an embodiment, R is:

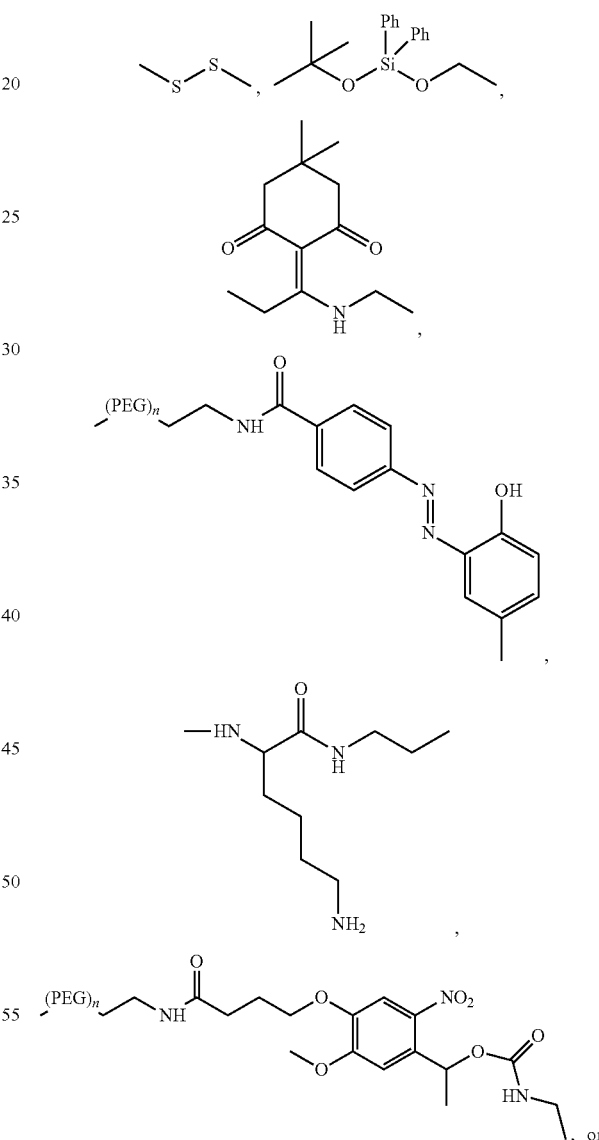

-continued

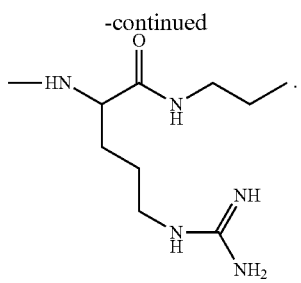

In an embodiment, the tagging reagent comprises a disulfide bond. Optionally, the tagging reagent comprises a tag having the formula:

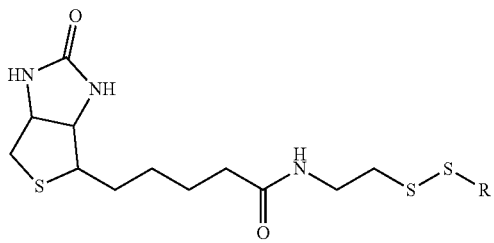

wherein R is selected from the group consisting of substituted and unsubstituted $C_1$ to $C_{24}$ alkyl groups, $C_1$ to $C_{24}$ cycloalkyl groups, $C_1$ to $C_{24}$ alkenyl groups, $C_1$ to $C_{24}$ cycloalkenyl groups, $C_4$ to $C_{24}$ aryl groups, $C_4$ to $C_{24}$ arylalkyl groups, and hydrogen. Optionally, R is selected from the group consisting of substituted and unsubstituted $C_1$ to $C_{12}$ alkyl groups, $C_1$ to $C_{12}$ cycloalkyl groups, $C_1$ to $C_{12}$ alkenyl groups, $C_1$ to $C_{12}$ cycloalkenyl groups, $C_4$ to $C_{12}$ aryl groups, $C_4$ to $C_{12}$ arylalkyl groups, and hydrogen.

In an embodiment, the tagging reagent comprises:

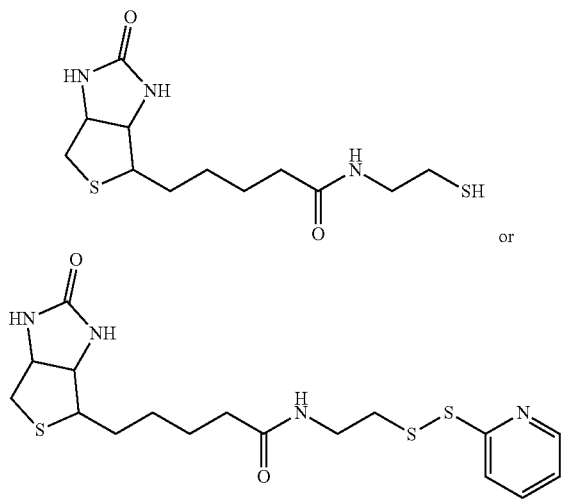

In an embodiment, the tagging reagent is attached to a solid support, such as resin beads, magnetic beads, or assay plates. In a further embodiment, the tagging reagent comprises a tag having the formula: $X-(CH_2)_n-R-SH$, wherein X is a solid support, such as resin/magnetic beads or an assay plate, n is an integer from 0 to 24, preferably from 0 to 12, from 0 to 6, or from 0 to 4, and R comprises one or more cleavable groups. Preferably, R comprise one or more cleavable groups, such as:

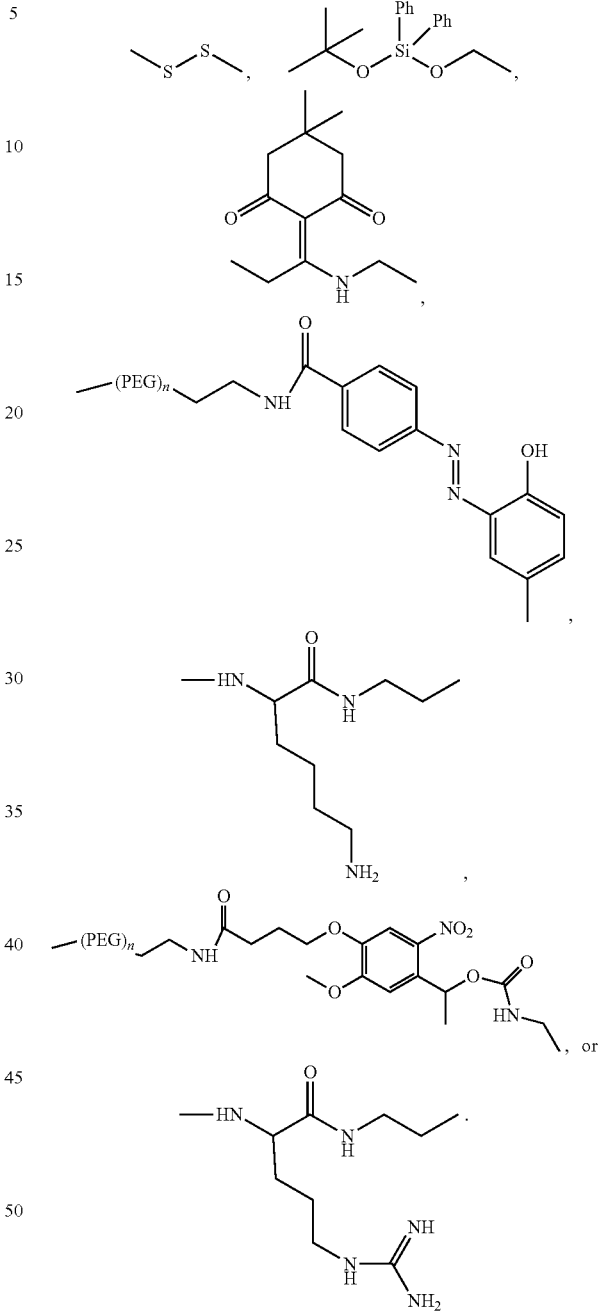

Optionally, the tagging reagent is an isotopically or isobarically enriched tagging reagent comprising one or more heavy isotopically labeled atoms. The tagging reagent can be any of the tagging reagents described above, wherein any number of carbons in the tagging reagent are $^{12}C$ or $^{13}C$, $^{14}N$ or $^{15}N$, $^1H$ or $^2H$; and $^{16}O$ or $^{18}O$.

The methods and tagging reagents described herein can be integrated with various MS-based quantitative proteomics strategies for relative quantitation of labeled biomolecules, particularly polypeptides having PTMs. As illustrated in FIG. 1, these strategies include stable isotopic labeling strategies, such as SILAC, dimethyl labeling, and mass defect-based tag labeling (e.g., DiPyrO tags), and isobaric labeling strategies such as tandem mass tag (TMT) labeling, dimethyl leucine (DiLeu) labeling and iTRAQ labeling (Boersema et al., Nat. Protoc., 2009, 4(4): 484-494; Dustin et al., Anal. Chem., 2017, 89(20): 10798-10805; Dustin et al., Anal. Chem., 2015, 87(3): 1646-1654; and Dustin et al., Anal. Chem. 2020, 92: 8228-8234). These strategies typically target amine groups at the N-termini of peptides, which allows the thiol and thioether containing tagging reagents of the present invention to react with the PTM side groups of a peptide. Consequently, these methods enable simultaneous qualitative and quantitative analysis of protein citrullination in biological and clinical samples.

Accordingly, in an embodiment, the method further comprises reacting the target biomolecule or labeled biomolecule with an isobaric labeling tag or a stable isotopic labeling tag. Preferably, the biomolecule is a polypeptide and the isobaric labeling tag or stable isotopic labeling tag is attached to the N-terminal region of the polypeptide. Preferably, the biomolecule is a citrullinated polypeptide and the stable isotopic labeling tag is an isotopically enriched dimethyl tag. Optionally, the isobaric labeling tag is a DiLeu, TMT or iTRAQ as discussed above.

In an embodiment, the method utilizes two or more isotopically enriched tagging reagents or two or more isobaric or stable isotopic labeling tags to label multiple samples containing the target biomolecules. In such applications, the method comprises providing two or more samples containing the target biomolecules; reacting the target biomolecules in each sample with a different isotopically enriched tagging reagent or a different isobaric or stable isotopic labeling tag, thereby generating samples comprising different isotopically or isobarically labeled target biomolecules; ionizing the isotopically or isobarically labeled target biomolecules in each sample to form precursor ions; and detecting and analyzing the precursor ions from each sample using a mass spectrometer. Preferably, the isotopically or isobarically enriched tagging reagents have molecular weights within 50 Da of each other, within 30 Da of each other, within 20 Da of each other, within 10 Da of each other, within 1 Da of each other, within 0.5 Da of each other, or within 0.1 Da of each other. In an embodiment, 2, 3, 4, 5, 6, 7, 8, 9, 10 or more different samples are reacted with different isotopically or isobarically enriched tagging reagents.

The reacting step optionally comprises additional reagents to generate the labeled biomolecules. For example, the reacting step optionally comprises adding a ketone, such as 2,3-butanedione, 2,3-butanedione monoxime, phenylglyoxal and derivatives thereof, with the tagging reagent to the target biomolecules. Phenylglyoxal was previously reported to be able to react with the citrulline residue. Accordingly, any phenylglyoxal derivatives that can react with a thiol group or other biotin tag structures should be able to help link the tag and citrullinated peptides. The structures of phenylglyoxal and its derivatives are shown below:

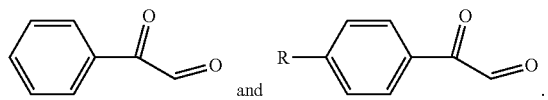

The R group, for example, can contain a thiol group or a conjugated system that is able to react with the biotin-thiol tag.

Preferably, the method further comprises enriching the labeled biomolecules in the sample prior to ionization. Enrichment of the labeled biomolecules, especially where a biotin-based tag is used, may be performed using streptavidin beads which are able to non-covalently bind with the labeled biomolecules.

In an embodiment, the tagging reagent imparts a mass shift to the target biomolecules, which allows the target biomolecules to be more easily identified and distinguished from other molecules, such as a protein having undergone a different PTM. However, the tagging reagents can not only change the solubility of tag-labeled biomolecules, but also affect the fragmentation patterns upon tandem mass spectrometry analysis. Thus, it is important to consider the influence of tagging reagents on MS-based fragmentation of tag-labeled biomolecules. If the tagging reagent has a mass over 500 Da, higher collisional energy is often required for the efficient fragmentation of these tag-labeled biomolecules. In addition, there are commonly more than one MS-cleavable sites present in these tagging reagents. When high collisional energy is used, the tagging reagents themselves will be cleaved, which could suppress the peptide backbone fragmentation and result in a tandem MS spectra with poor quality. Hence, a small tagging reagent with no more than one MS-cleavable site is preferable for MS-based analysis. In an embodiment, reacting the tagging reagent with the target biomolecules imparts a mass shift from approximately 1 Da to 500 Da to the target biomolecules. Preferably, reacting the tagging reagent with the target biomolecules imparts a mass shift from 10 Da to 400 Da to the target biomolecules, from 20 Da to 350 Da to the target biomolecules, from 20 Da to 250 Da to the target biomolecules, or from 100 Da to 200 Da to the target biomolecules.

One embodiment of the present invention provides tagging reagents comprising a thiol-containing biotin-based tag for the qualitative analysis of citrullinated peptides or proteins. In an embodiment, the biotin-based tag works together with 2,3-butanedione to specifically derivatize an ureido group at the side chain of peptidylcitrulline, enabling the concurrent biotinylation of citrullinated peptides and a mass shift from 0.984 Da to 355 Da upon citrullination. Following this, the biotin-modified citrullinated peptides are able to be enriched and released for MS-based identification. Meanwhile, due to the enlarged mass shift, citrullination sites can be precisely annotated, eliminating the interference of deamidation.

The biotin-based tags disclosed herein are easy to synthesize at high purity in just one step using simple chemistry and cheap commercial reagents. This makes the technology affordable to produce at high yield in a short time scale. Additionally, no particularly dangerous reaction conditions or reagents are involved. Previously reported tags have been large in size and need to be synthesized with expensive reagents in multi-step reactions.

The labeling efficiency of these biotins-based tags has been investigated with a synthesized citrullinated peptide standard. In an experiment, it was observed that >90% of citrullinated peptide standard could be derivatized using a 6 hr labeling reaction.

Until now, no MS-based method has been reported for quantitative analysis of citrullinated proteins from biological and clinical samples. In an embodiment, a biotin tag-assisted MS-based qualitative method is integrated with multiple MS-based quantitative proteomics strategies, such as, stable isotopic labeling strategies (stable isotope labeling by amino acids in cell culture (SILAC) & dimethyl labeling) or isobaric labeling strategies (TMT labeling & DiLeu labeling), to develop a MS-based method for simultaneous large-scale identification and relative quantitation of citrullinated proteins from different biological samples. In an embodiment, the biotin tag-assisted qualitative method is combined with the dimethyl labeling strategy. The qualitative performance of the combined method is tested with citrullinated peptide standard and complex biological samples.

DETAILED DESCRIPTION OF THE INVENTION

Definitions

Figure 1:
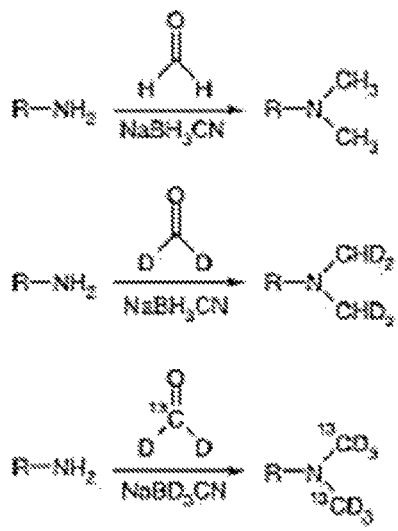
FIG. 1 illustrates MS-compatible quantitative strategies which are able to be combined with thiol and thioether tagging reagents and methods of the present invention to provide relative quantitation of labeled molecules, particularly polypeptides having PTMs.
Figure 1:
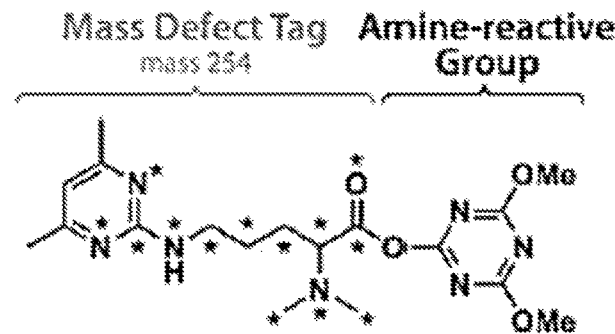
Figure 1:
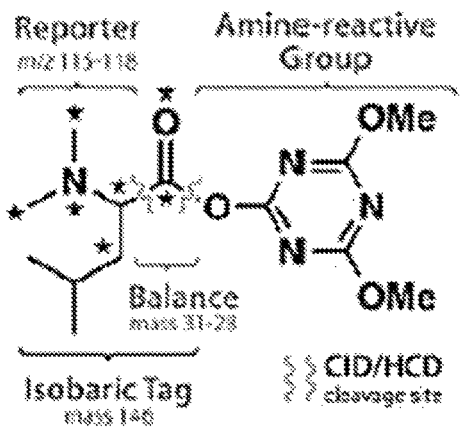
Figure 1:
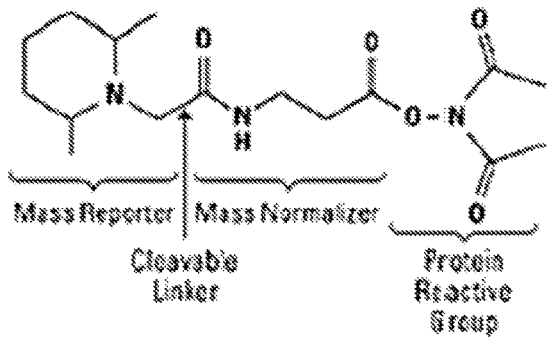

In general, the terms and phrases used herein have their art-recognized meaning, which can be found by reference to standard texts, journal references and contexts known to those skilled in the art. The following definitions are provided to clarify their specific use in the context of the invention.

As used herein, the term "analyzing" refers to a process for determining a property of an analyte. Analyzing can determine, for example, physical properties of analytes, such as mass, mass to charge ratio, concentration, absolute abundance, relative abundance, or atomic or substituent composition. In the context of proteomic analysis, the term analyzing can refer to determining the composition (e.g., amino acid sequence, PTM site) and/or abundance of a protein or peptide in a sample.

As used herein, the term "analyte" refers to a compound, mixture of compounds or other composition which is the subject of an analysis. Analytes include, but are not limited to, proteins, modified proteins, peptides, modified peptides, small molecules, pharmaceutical compounds, oligonucleotides, sugars, polymers, metabolites, lipids, and mixtures thereof.

As used herein, the term "mass spectrometry" (MS) refers to an analytical technique for the determination of the elemental composition, mass to charge ratio, absolute abundance and/or relative abundance of an analyte. Mass spectrometric techniques are useful for elucidating the composition and/or abundance of analytes, such as proteins, peptides and other chemical compounds. Mass spectrometry includes processes comprising ionizing analytes to generate charged species or species fragments, fragmentation of charged species or species fragments, such as product ions, and measurement of mass-to-charge ratios of charged species or species fragments, optionally including additional processes of isolation on the basis of mass to charge ratio, additional fragmentation processing, charge transfer processes, etc. Conducting a mass spectrometric analysis of an analyte results in the generation of mass spectrometry data for example, comprising the mass-to-charge ratios and corresponding intensity data for the analyte and/or analyte fragments. Mass spectrometry data corresponding to analyte ion and analyte ion fragments is commonly provided as intensities as a function of mass-to-charge (m/z) units representing the mass-to-charge ratios of the analyte ions and/or analyte ion fragments. Mass spectrometry commonly allows intensities corresponding to different analytes to be resolved in terms of different mass to charge ratios. In tandem mass spectrometry (MS/MS or $MS^2$), multiple sequences of mass spectrometry analysis are performed. For example, samples containing a mixture of proteins and peptides can be ionized and the resulting precursor ions separated according to their mass-to-charge ratio. Selected precursor ions can then be fragmented and further analyzed according to the mass-to-charge ratio of the fragments.

As used herein, the term "mass-to-charge ratio" refers to the ratio of the mass of a species to the charge state of a species. The term "m/z unit" refers to a measure of the mass to charge ratio. The Thomson unit (abbreviated as Th) is an example of an m/z unit and is defined as the absolute value of the ratio of the mass of an ion (in Daltons) to the charge of the ion (with respect to the elemental charge).

As used herein, the term "mass spectrometer" refers to a device which generates ions from a sample, separates the ions according to mass to charge ratio, and detects ions, such as product ions derived from isotopically enriched compound, isotopic tagging reagents, isotopically labeled amino acids and/or isotopically labeled peptide or proteins. Mass spectrometers include single stage and multistage mass spectrometers, which include tandem mass spectrometers that fragment the mass-separated ions and separate the product ions by mass.

As used herein, the term "precursor ion" is used herein to refer to an ion which is produced during ionization stage of mass spectrometry analysis, including the $MS^1$ ionization stage of MS/MS analysis.

"Fragment" refers to a portion of molecule, such as a peptide. Fragments may be singly or multiply charged ions, and may be derived from bond cleavage in a parent molecule, including site specific cleavage of polypeptide bonds in a parent peptide. Fragments may also be generated from multiple cleavage events or steps. Fragments may be a truncated peptide, either carboxy-terminal, amino-terminal or both, of a parent peptide. A fragment may refer to products generated upon the cleavage of a polypeptide bond, a C—C bond, a C—N bond, a C—O bond or combination of these processes. Fragments may refer to products formed by processes where one or more side chains of amino acids are removed, or a modification is removed, or any combination of these processes. Fragments useful in the present invention include fragments formed under metastable conditions or from the introduction of energy to the precursor by a variety of methods including, but not limited to, collision induced dissociation (CID), surface induced dissociation (SID), laser induced dissociation (LID), electron capture dissociation (ECD), electron transfer dissociation (ETD), or any combination of these methods or any equivalents known in the art of tandem mass spectrometry. Fragments useful in the present invention also include, but are not limited to, x-type fragments, y-type fragments, z-type fragments, a-type fragments, b-type fragments, c-type fragments, internal ion (or internal cleavage ions), immonium ions or satellite ions. The types of fragments derived from an analyte, such as an isotopically labeled analyte, isotopically labeled standard and/or isotopically labeled peptide or proteins, often depend on the sequence of the parent, method of fragmentation, charge state of the parent precursor ion, amount of energy introduced to the parent precursor ion and method of delivering energy into the parent precursor ion. Properties of fragments, such as molecular mass, may be characterized by analysis of a fragmentation mass spectrum.

The terms "peptide" and "polypeptide" are used synonymously in the present description, and refer to a class of compounds composed of amino acid residues chemically bonded together by amide bonds (or peptide bonds). Peptides and polypeptides are polymeric compounds comprising at least two amino acid residues or modified amino acid residues. Modifications can be naturally occurring or non-naturally occurring, such as modifications generated by chemical synthesis. Modifications to amino acids in peptides include, but are not limited to, acetylation, acylation, alkylation, amidation, carbamylation, citrullination, glycosylation, hydroxylation, iodination, lipidation, methionine oxidation, methylation, nitrosylation, phosphorylation, prenylation, sulfonation, neddylation, SUMOylation, ubiquitination, and the addition of cofactors. Peptides include proteins and further include compositions generated by degradation of proteins, for example by proteolytic digestion. Peptides and polypeptides can be generated by substantially complete digestion or by partial digestion of proteins. Polypeptides include, for example, polypeptides comprising 2 to 100 amino acid units, optionally for some embodiments 2 to 50 amino acid units and, optionally for some embodiments 2 to 20 amino acid units and, optionally for some embodiments 2 to 10 amino acid units.

"Protein" refers to a class of compounds comprising one or more polypeptide chains and/or modified polypeptide chains. Proteins can be modified by naturally occurring processes such as post-translational modifications or co-translational modifications. Exemplary post-translational modifications or co-translational modifications include, but are not limited to, phosphorylation, glycosylation, lipidation, prenylation, sulfonation, hydroxylation, acetylation, methylation, methionine oxidation, the addition of cofactors, proteolysis, and assembly of proteins into macromolecular complexes. Modification of proteins can also include non-naturally occurring derivatives, analogues and functional mimetics generated by chemical synthesis. Exemplary derivatives include chemical modifications such as alkylation, acylation, carbamylation, iodination or any modification that derivatizes the protein.

Quantitative analysis in chemistry is the determination of the absolute or relative abundance of one, several, or all particular substance(s) present in a sample. For biological samples, quantitative analysis performed via mass spectrometry can determine the relative abundances of peptides and proteins. The quantitation process typically involves isotopic labeling of protein and peptide analytes and analysis via mass spectrometry.

Many of the molecules disclosed herein contain one or more ionizable groups. Ionizable groups include groups from which a proton can be removed (e.g., —COOH) or added (e.g., amines) and groups which can be quaternized (e.g., amines). All possible ionic forms of such molecules and salts thereof are intended to be included individually in the disclosure herein. With regard to salts of the compounds herein, one of ordinary skill in the art can select from among a wide variety of available counterions that are appropriate for preparation of salts of this invention for a given application. In specific applications, the selection of a given anion or cation for preparation of a salt can result in increased or decreased solubility of that salt.

The compounds of this invention can contain one or more chiral centers. Accordingly, this invention is intended to include racemic mixtures, diasteromers, enantiomers, tautomers and mixtures enriched in one or more stereoisomer. The scope of the invention as described and claimed encompasses the racemic forms of the compounds as well as the individual enantiomers and non-racemic mixtures thereof.

As used herein, "isotopically enriched" and "isotopically labeled" refer to compounds (e.g., such as isotopically labeled amino acids, isotopically labeled standards, isotopically labeled analyte, isotopic tagging reagents, and/or isotopically labeled peptide or proteins) having one or more isotopic labels, such as one or more heavy stable isotopes, present in an amount greater than the naturally occurring abundance. An "isotopic label" refers to one or more heavy stable isotopes introduced to a compound, such as isotopically labeled amino acids, isotopically labeled standards, isotopically labeled analyte, isotopic tagging reagents, and/ or isotopically labeled peptide or proteins, such that the compound generates a signal when analyzed using mass spectrometry that can be distinguished from signals generated from other compounds, for example, a signal that can be distinguished from other isotopologues on the basis of mass-to-charge ratio. "Isotopically-heavy" refers to a compound or fragments/moieties thereof having one or more high mass, or heavy isotopes (e.g., stable heavy isotopes such as $^{13}C$, $^{15}N$, $^{2}H$, $^{17}O$, $^{18}O$, $^{33}S$, $^{34}S$, $^{37}Cl$, $^{81}Br$, $^{29}Si$, and $^{30}Si$).

In an embodiment, an isotopically enriched composition comprises a compound of the invention having a specific isotopic composition, wherein the compound is present in an abundance that is at least 10 times greater, for some embodiments at least 100 times greater, for some embodiments at least 1,000 times greater, for some embodiments at least 10,000 times greater, than the abundance of the same compound having the same isotopic composition in a naturally occurring sample. In another embodiment, an isotopically enriched composition has a purity with respect to a compound of the invention having a specific isotopic composition that is substantially enriched, for example, a purity equal to or greater than 90%, in some embodiments equal to or greater than 95%, in some embodiments equal to or greater than 99%, in some embodiments equal to or greater than 99.9%, in some embodiments equal to or greater than 99.99%, and in some embodiments equal to or greater than 99.999%. In another embodiment, an isotopically enriched composition is a sample that has been purified with respect to a compound of the invention having a specific isotopic composition, for example using isotope purification methods known in the art.

Overview

Post-translational modifications (PTMs) are involved in many serious diseases. Owing to the lack of effective methods for analyzing post-translational modified proteins, such as citrullination, comprehensive study of such modifications is an as-yet-unresolved challenge.

Figure 2:
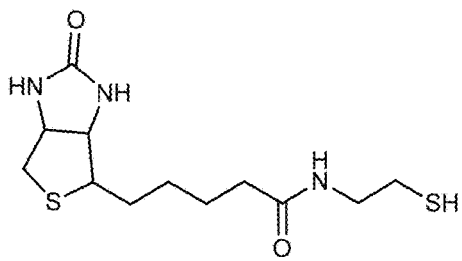
FIG. 2 shows exemplary thiol-containing biotin tags without cleavable groups in an embodiment of the present invention.
Figure 2:
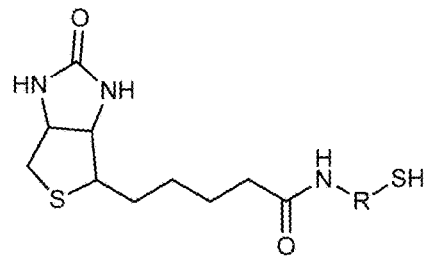
Figure 2:
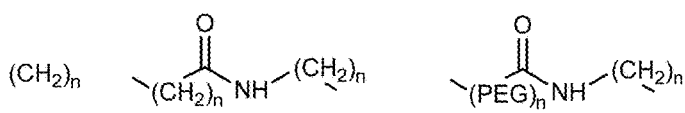
Figure 2:
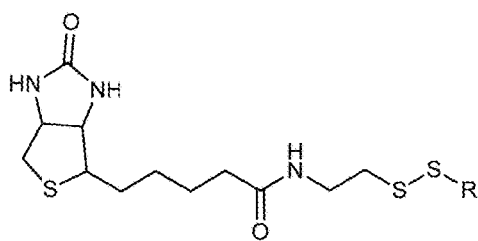
Figure 2:
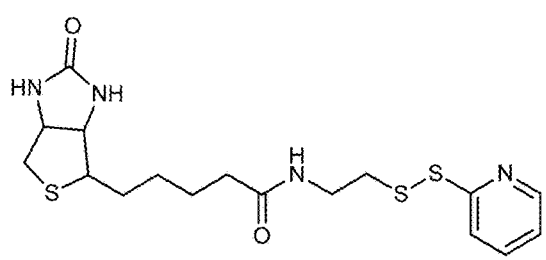
Figure 3:
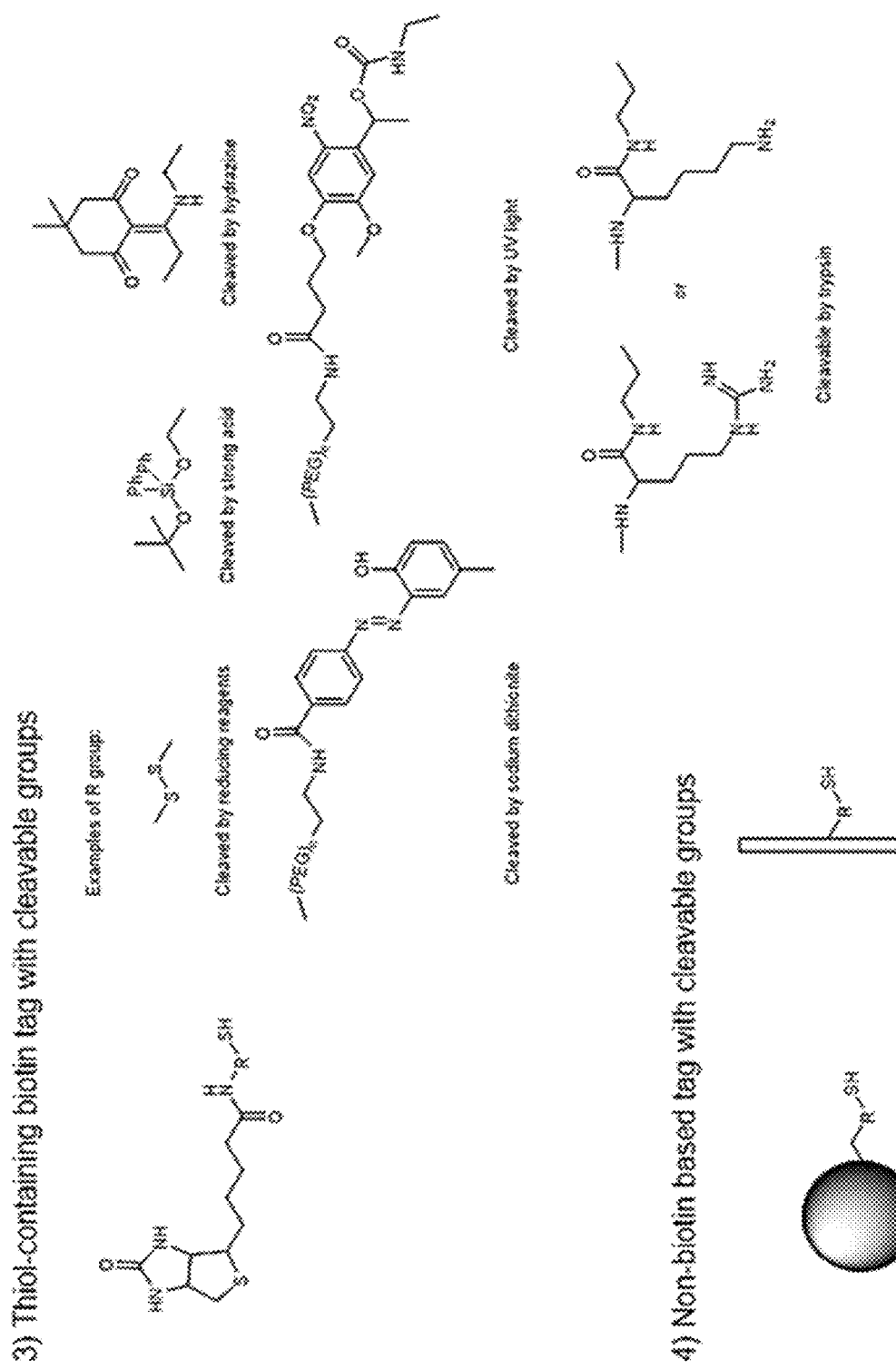
FIG. 3 shows exemplary thiol-containing tags containing cleavable groups in an embodiment of the present invention.

The present invention provides a novel multi-faceted method, combining a chemical derivatization, biotin tag-assisted enrichment strategy with mass spectrometry (MS)-based technologies, for the qualitative and quantitative analysis of target biomolecules, particularly post-translation modified proteins from complex biological samples. FIGS. 2 and 3 show exemplary thiol-containing biotin tags able to bind to such target biomolecules in order to generate labeled biomolecules able to be resolved by mass spectrometry analysis. For example, the methods of the present invention can be used to analyze the citrullination and homocitrullination/carbamylation of peptides. As illustrated further below, this method has been successfully applied to mouse tissue-specific protein citrullination analysis. In total, 619 citrullinated proteins and 1198 citrullination sites were identified with high confidence. Results indicate that citrullinated proteins are widely distributed in cellular compartments, and play important roles in many critical cellular and physiological processes.

Figure 4:
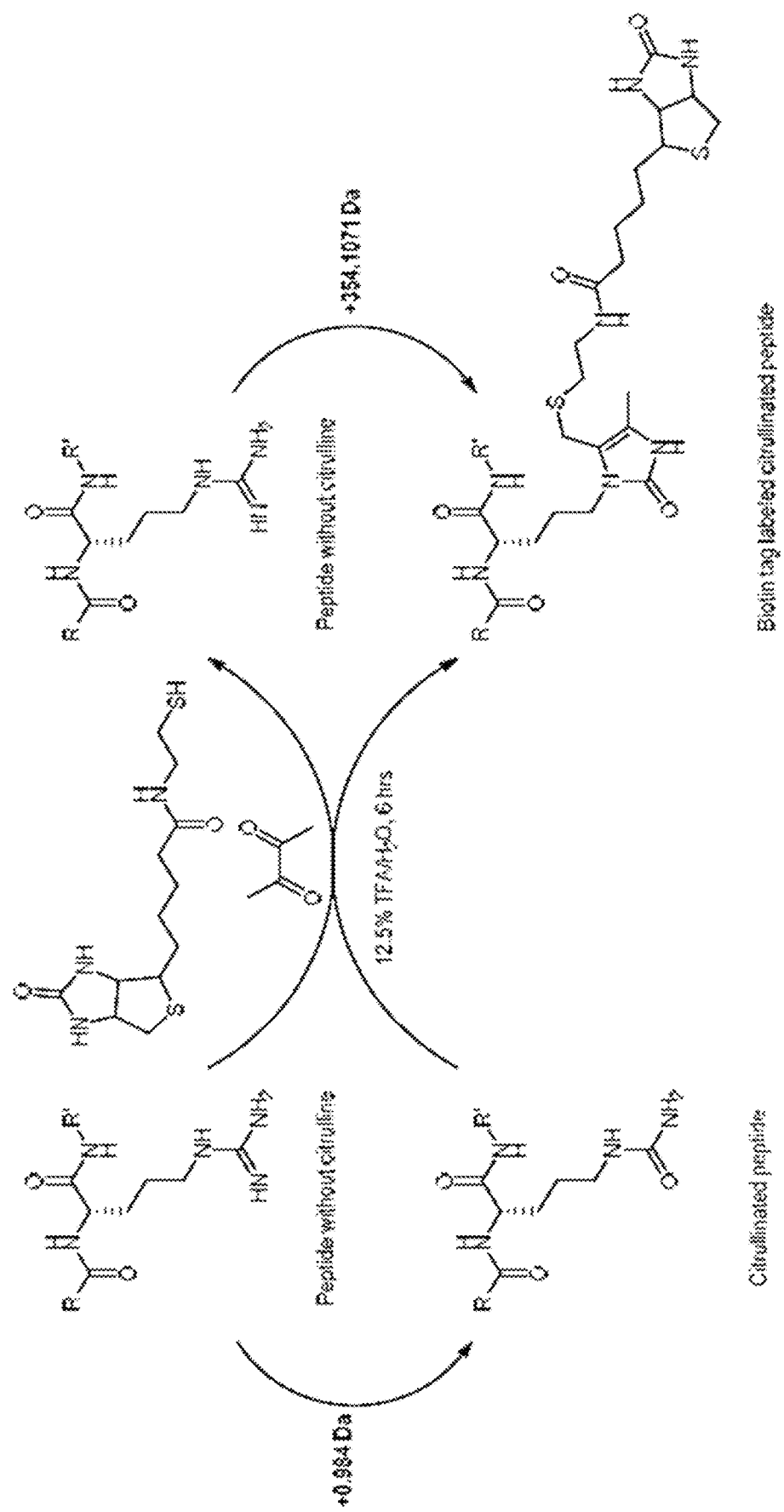
FIG. 4 shows an exemplary biotin tag-assisted chemical modification of a citrullinated peptide.

The biotin-based tags described herein can target peptidylcitrulline, and therefore enable selective enrichment of citrullinated peptides from samples for large-scale analysis (FIG. 4). It is easy to synthesize at high purity in just one step using simple chemistry and cheap commercial reagents. The previously reported tags used for citrullinated peptides are large in size and need to be synthesized with expensive reagents in multi-step reactions. The present tag is also much smaller and more hydrophilic than the previously reported tag. The peptide backbone fragmentation efficiency of peptides labeled by the present tag is not significantly suppressed, and more high-quality MS/MS spectra are able to be obtained, manifested by an overall increase in identifications of citrullinated proteins.

In at least one experiment, the labeling efficiency is >90% using a 6-hour labeling reaction, and the present biotin tag-assisted qualitative methods have been successfully combined with a isotopic dimethyl labeling strategy.

The previously reported biotin tag designed for MS-based large-scale citrullination analysis (Astrid E. V. Tutturen et al., J. Proteome Res. 2014, 13, 2867-2873) has significant drawbacks including: a) the tag can impart a mass shift of +516.2 Da per tag to labeled peptides, which negatively affects the solubility, chromatographic separation, and ionization efficiency of labeled peptides, especially when double-labeled; and b) the biotin tag itself has multiple fragmentation sites upon HCD fragmentation, resulting in a large amount of tag-derived fragment ions in MS/MS spectra. As mentioned in Tutteren et al., the fragmentation of their tag could suppress the fragmentation yield of peptide backbone, and therefore significantly reduce the quality of peptide MS/MS spectra, leading to fewer numbers of citrullinated protein identifications (17 reported in manuscript), even less than the direct analysis without enrichment.

The methods and tags described herein address these problems directly: a) the present tags are much smaller and more hydrophilic than the previously reported tag; and b) the backbone fragmentation efficiency of peptide labeled by the present tags is not significantly suppressed, and more high quality MS/MS spectra can therefore be obtained, manifested by the overall increase of identifications of citrullinated proteins following database search.

Citrullinated peptides labeled by the present tags can also be identified by various commonly used MS fragmentation techniques, and therefore are able to be widely adopted on different MS platforms. For example, two fragment ions at m/z 227 and 304 produced upon HCD and EThcD fragmentation, can be used as diagnostic ions to exclude the false identification of citrullinated proteins, further improving the identification accuracy.

Example 1

Figure 5:
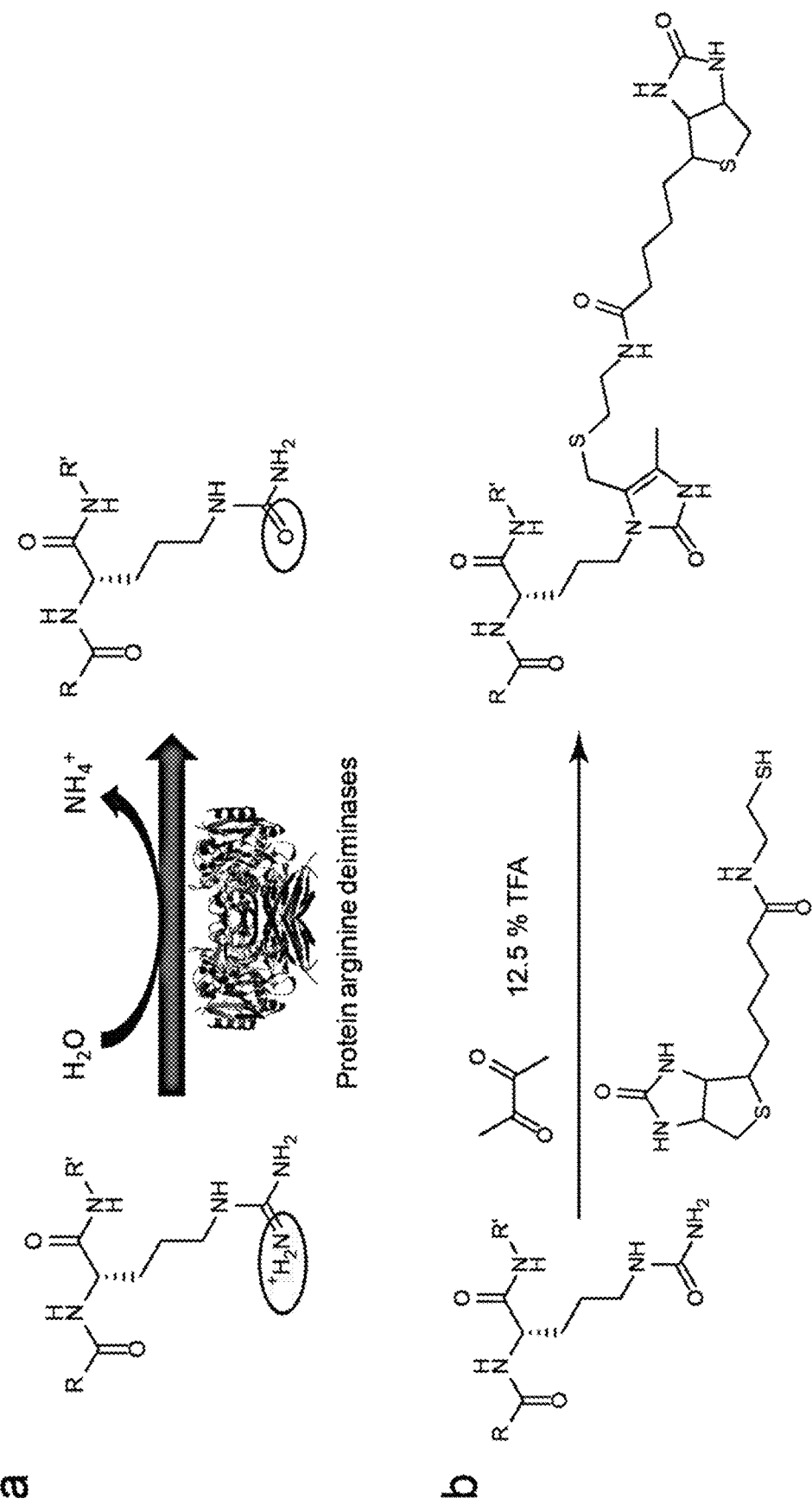
FIG. 5 illustrates (a) that a protein arginine residue can be modified to a citrulline residue catalyzed by protein arginine deiminase, and (b) that the ureido group of a peptidycitrulline residue can be specifically derivatized by 2, 3-butanedione and a novel biotin cysteamine tag in low pH aqueous solution.

Protein citrullination, catalyzed by a small family of enzymes called peptidylarginine deiminases (PADs), is an important PTM crucial for maintaining protein structures, functions and physiological homeostasis (FIG. 5, panel a). Proteins with aberrant citrullination could serve as autoantigens to stimulate immune system and initiate pathogenic immune responses, contributing to numerous autoimmune diseases, such as rheumatoid arthritis (RA) and multiple sclerosis. One instance is the presence of anti-citrullinated protein antibodies (ACPA) in the plasma of majority patients with RA, which has been used in clinic as a biomarker for RA diagnosis. Recently, accumulating evidence revealed the essential roles of protein citrullination in many important cellular processes and diseases. Although functionally important, the current understanding about citrullination in terms of its cellular distribution and function is rather limited and primarily impeded by the lack of effective analytical tools.

Current citrullination studies mainly rely on conventional antibody-based techniques such as immunohistochemistry (IHC), enzyme-linked immunosorbent assay (ELISA) analysis, and Western blotting (WB). However, these antibodies could either target a specific protein, or be applied for general citrullination analysis. Furthermore, protein citrullination site information is typically not revealed by these antibody-based detection methods. No antibodies are currently able to enrich citrullinated peptides/proteins from complex biological samples for large-scale citrullination analysis. Additionally, methods for global citrullination analysis are still missing.

In recent years, mass spectrometry (MS)-based bottom-up proteomics has been proven to be a useful tool for large-scale protein PTM analysis. However, its application to protein citrullination analysis suffers from several challenges including: i) methods enabling specific capture of citrullinated peptides for MS analysis are not effective; ii) the mass shift of 0.984 Da induced by citrullination is the same as that of another modification called deamidation; and iii) $^{13}$C isotopic peaks in tandem MS spectra have a mass shift of 1.0033 Da, which is close to that of citrullination. These will interfere with the accurate annotation of peptide fragment ions upon automated MS data processing, leading to misidentification of citrullination sites.

To address these challenges, a novel method is introduced integrating a chemical derivatization, biotin tag-assisted enrichment strategy with mass spectrometry (MS)-based technology, for the large-scale and high-confident identification of citrullinated proteins from biological samples.

A bifunctional thiol-containing biotin tag was developed for concurrent chemical derivatization and biotinylation of citrullinated peptides. The free thiol group of the tag, together with 2,3-butanedione, specifically modifies the ureido group at the side chain of peptidylcitrulline in low pH aqueous solution, while the biotin group enables the enrichment of derivatized citrullinated peptides. The biotin tag-modified citrullinated peptides were then enriched and released for MS analysis. The biotin tags disclosed herein are able to target peptidylcitrulline, and therefore enable unbiased enrichment of citrullinated peptides from samples for largescale analysis.

Furthermore, by integrating the biotin tag-based chemical derivatization strategy with the stable isotopic dimethyl labeling-based quantitation strategy, citrullinated proteins from different biological samples are able to be simultaneously identified and relatively quantified, which is critical to unravel the important cellular biological functions of protein citrullination.

Figure 6:
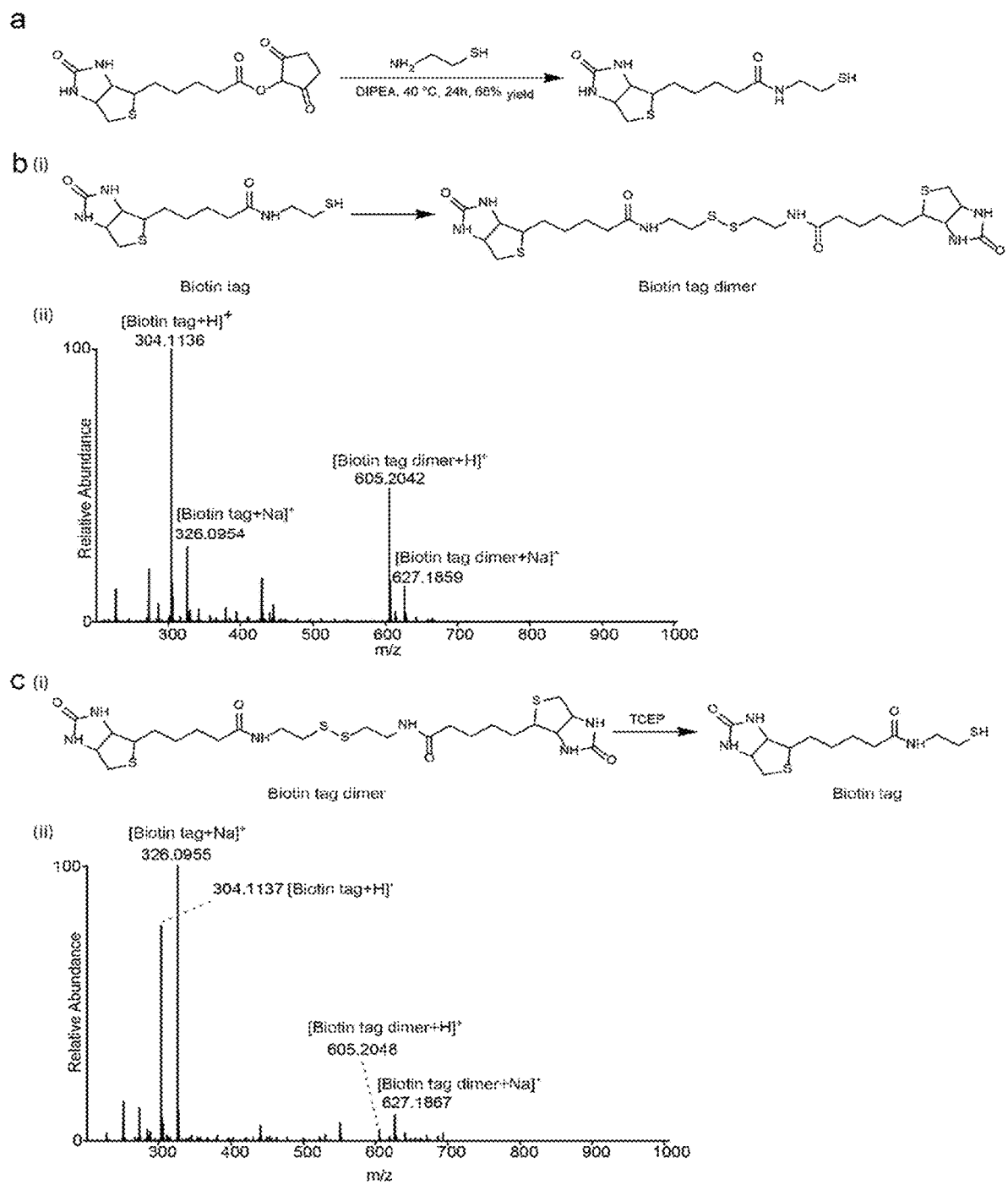
FIG. 6 shows synthesis and protection of a biotin cysteamine tag. (a) One step synthesis of biotin cysteamine tag. (b) The formation of biotin tag dimer upon tag synthesis and storage (i); MALDI-Orbitrap mass spectrometry analysis of biotin tag indicated the presence of biotin tag dimer (ii). (c) Tris (2-carboxyethyl) phosphine (TCEP), as a reducing reagent, could protect the biotin tag from the formation of dimer (i); The protection effect of TCEP was examined by the MALDI-LTQ orbitrap mass spectrometry analysis (ii).
Figure 7:
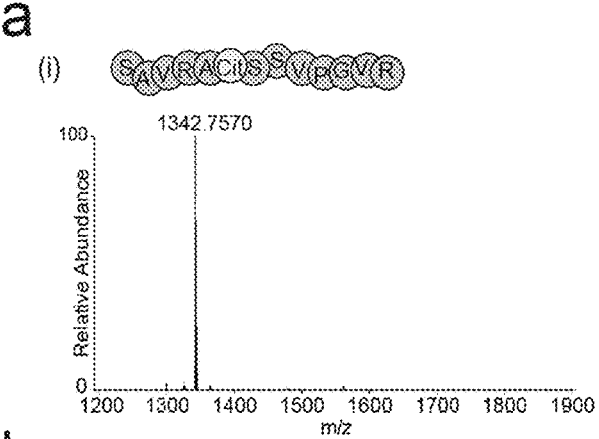
FIG. 7 shows results of a biotin tag-based chemical derivatization of a citrullinated peptide standard (SEQ ID NO:1). (a) Test the derivatization reaction with MALDI orbitrap mass spectrometry. The synthesized citrullinated peptide standard (i); modified citrullinated peptide standard post 6 h chemical derivatization with 2, 3-butanedione and biotin cysteamine tag (ii). (b) Test the derivatization reaction with ESI mass spectrometry. Standard citrullinated peptide before derivatization (i); citrullinated peptide standard was completely modified after 6 h derivatization (ii). Peak at m/z 1392.7745 could either be generated by the reaction of 2, 3-butanedione with citrullinated peptide standard (less than 1%), or by the neutral loss from biotin tag modified citrullinated peptide standard (about 1%) (iii). Biotin tag-modified citrullinated peptide standard. A stereoisomer resulting from the derivatization reaction was observed (iv).
Figure 7:
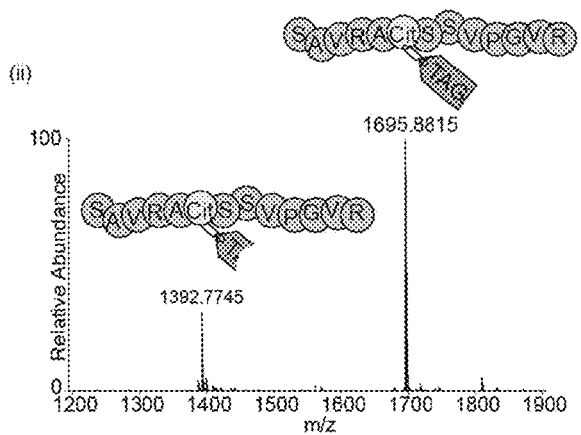
Figure 7:
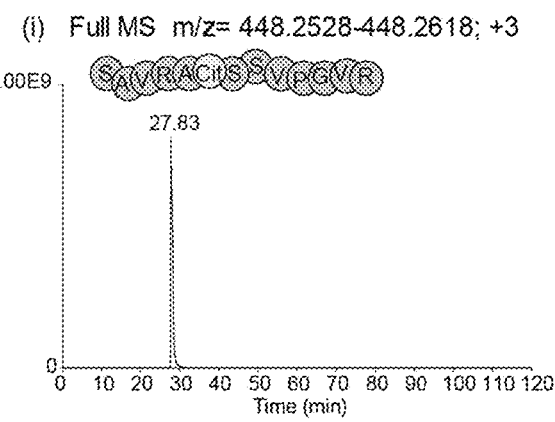
Figure 7:
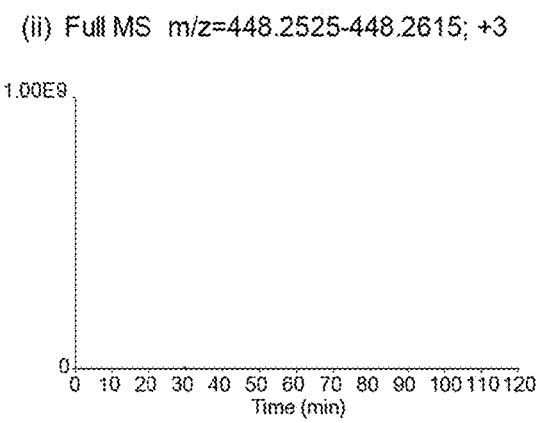
Figure 7:
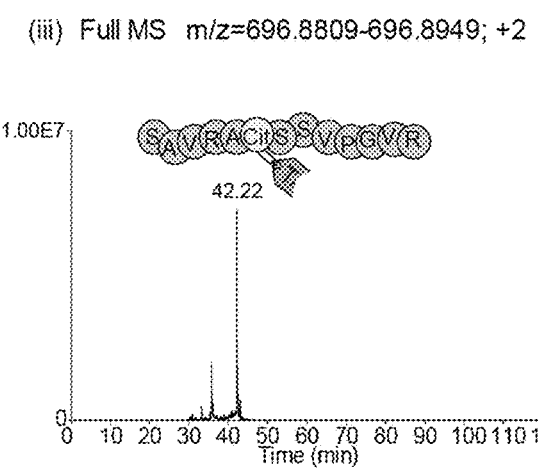
Figure 7:
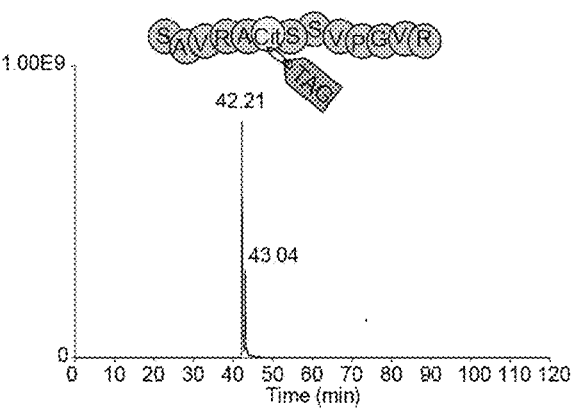
Figure 8:
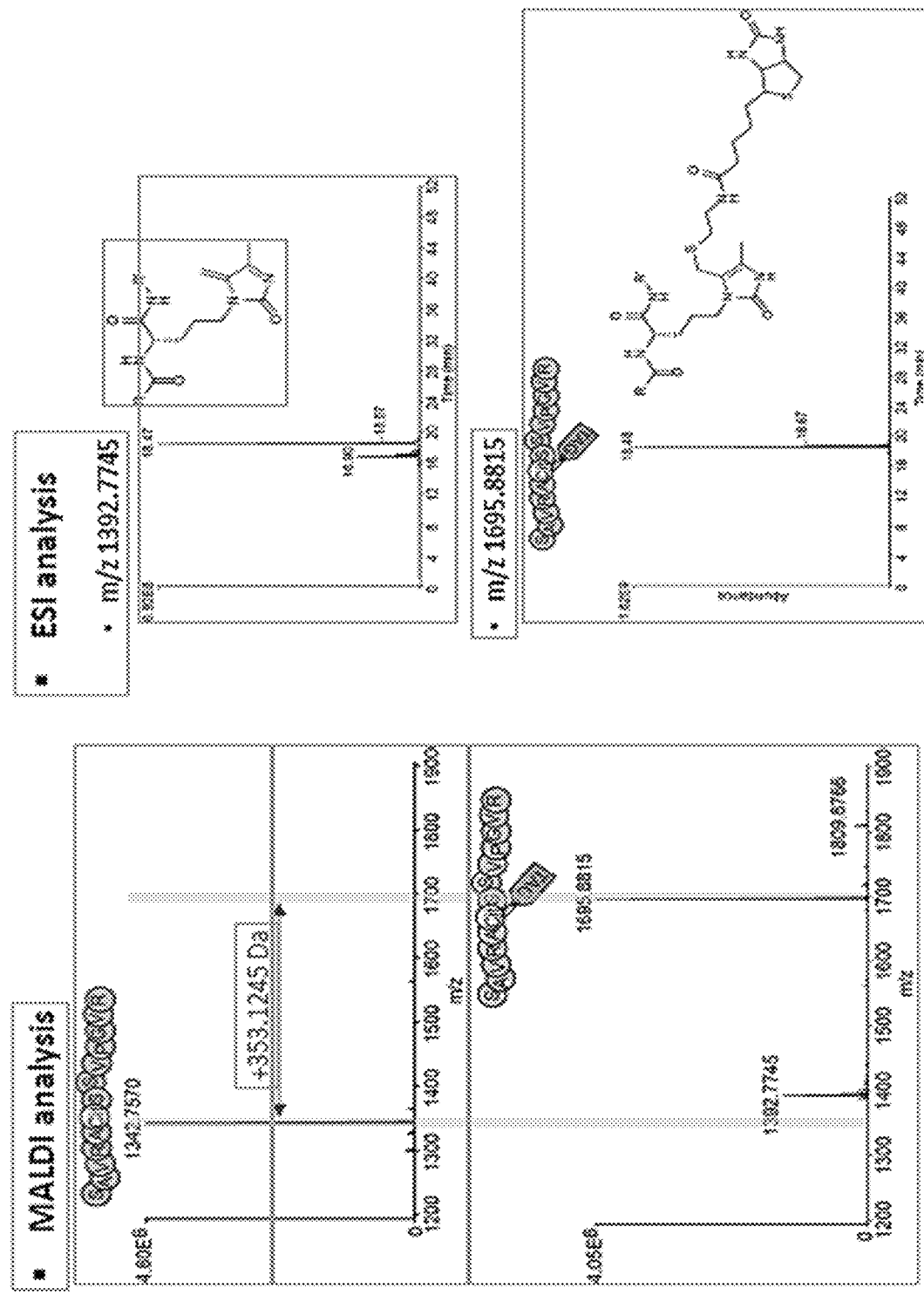
FIG. 8 shows MALDI and ESI analysis of a chemical derivatization of a citrullinated peptide standard (SEQ ID NO:1). The labeling efficiency was greater than 90%.
Figure 9:
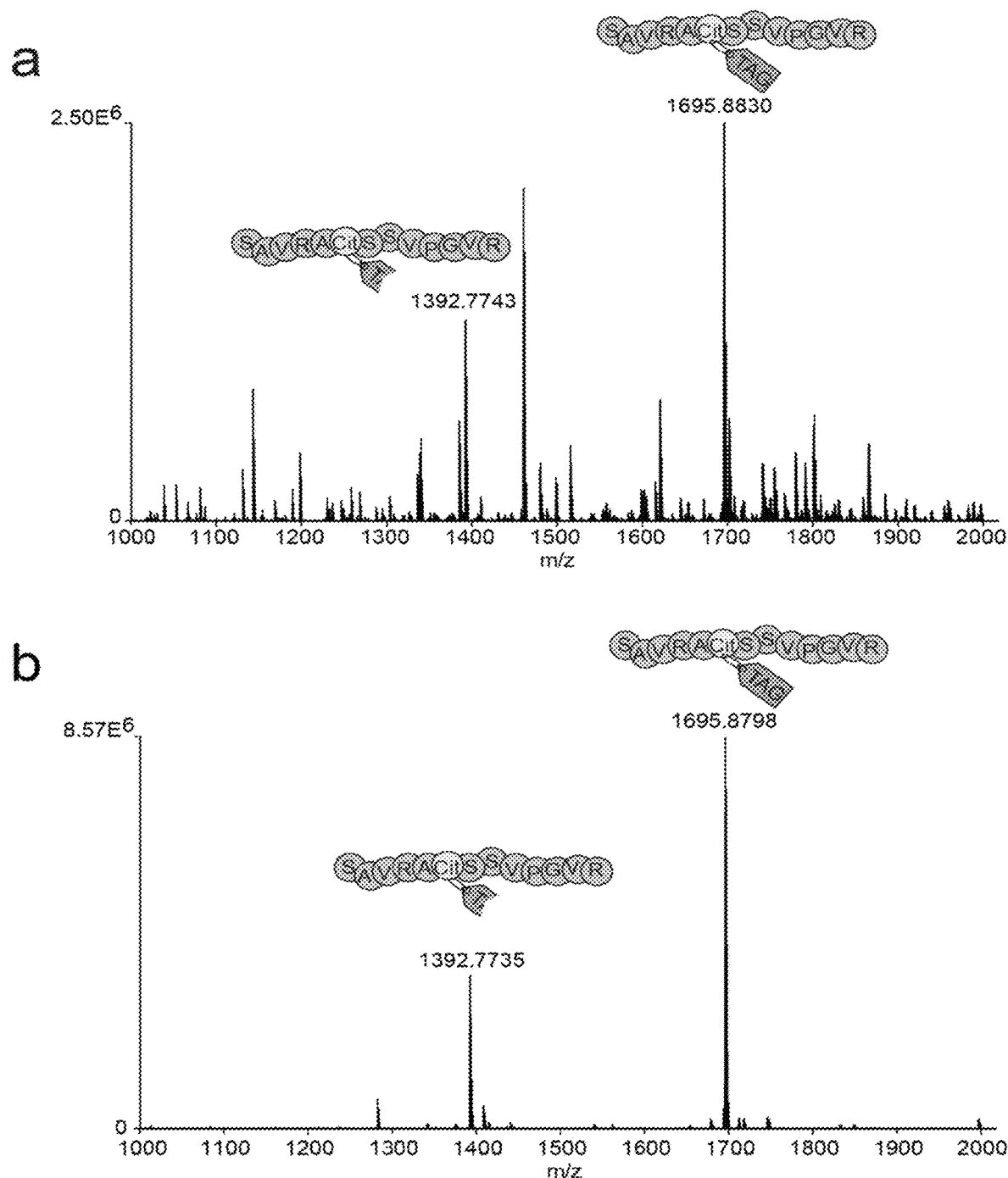
FIG. 9 illustrates the enrichment and release of a biotin tag-modified citrullinated peptide standard (SEQ ID NO:1) from a peptide mixture. (a) Biotin tag-modified citrullinated peptide standard was spiked into 400 μg peptide mixture digested from mouse brain. Before streptavidin enrichment, the sample was tested using MALDI-orbitrap MS. (b) Post streptavidin enrichment, the eluted sample was tested on MALDI-orbitrap MS. The result suggested that the biotin tag-modified citrullinated peptide standard could be successfully enriched from peptide mixture and released from streptavidin beads. Peak at m/z 1392.7735 resulted from the neutral loss of peak 1695.8798 upon laser desorption.

It was firstly noticed that a free thiol group, together with 2,3-butanedione, could specifically modify the ureido group at the side chain of peptidylcitrulline in low pH aqueous solution. Thus, a bifunctional thiol-containing biotin tag was developed for the concurrent chemical derivatization and biotinylation of citrullinated peptides (FIG. 5, panel b). Notably, the thiol-containing biotin tag was easy to be synthesized in just one step using simple chemistry and low-cost commercial reagents (FIG. 6, panel a). With the protection of tris (2-carboxyethyl) phosphine (TCEP), high purity biotin tag could be obtained and stored for long-term usage (FIG. 6, panels b and c). A citrullinated peptide standard (SAVRACitSSVPGVR (SEQ ID NO:1), Genscript) was synthesized to examine the chemical derivatization efficiency of the novel biotin tag. It was found that the citrullinated peptide standard could be efficiently derivatized after 6 h reaction (FIG. 7 and FIG. 8). Next, the derivatized citrullinated peptide standard was spiked into a peptide mixture, and demonstrated that the derivatized citrullinated peptide standard could be successfully enriched and released from streptavidin beads though no cleavable group was present in the spacer arm of the biotin tag (FIG. 9). A workflow for large-scale protein citrullination analysis of complex biological samples using streptavidin beads is shown in FIG. 10, panel a.

Figure 10:
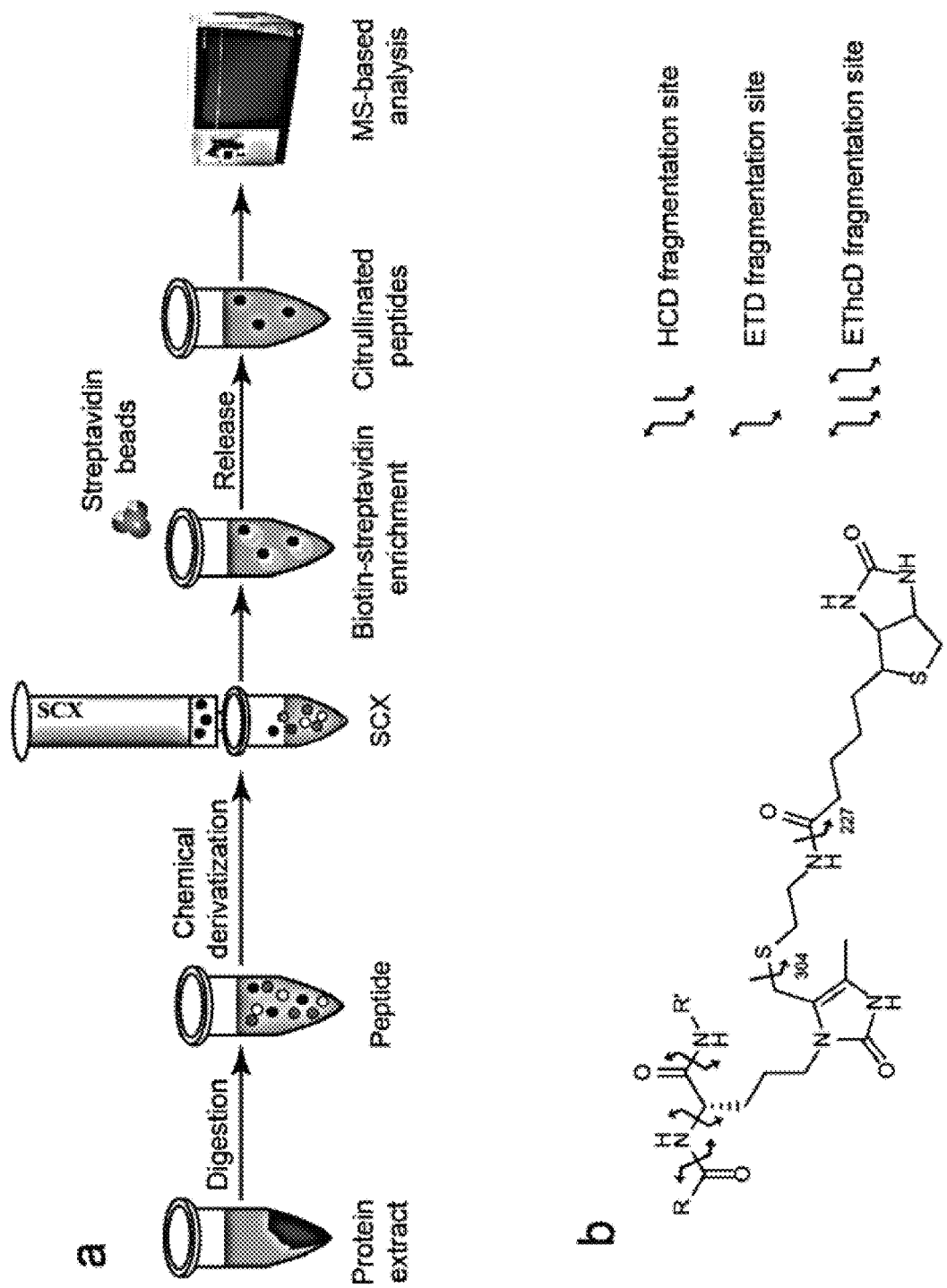
FIG. 10 shows (a) a workflow for large-scale protein citrullination analysis of complex biological samples using MS-based analysis, and (b) fragmentation sites of biotin tag-modified citrullinated peptides upon mass spectrometry-based analysis using HCD, ETD and EThcD fragmentation techniques.
Figure 11:
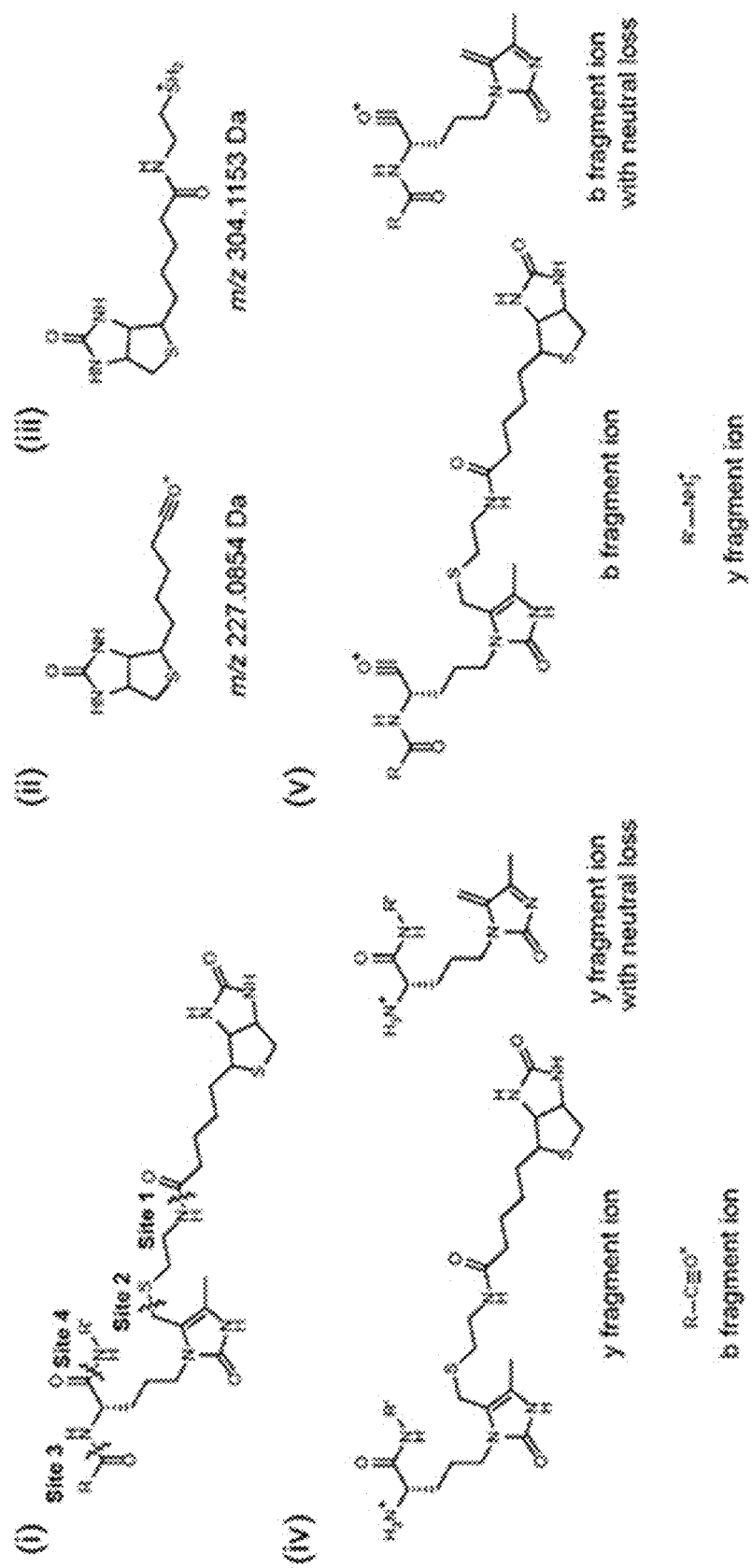
FIG. 11 illustrates a HCD fragmentation pattern of a biotin tag-modified citrullinated peptide. Cleavage sites of biotin tag-modified citrullinated peptide upon HCD fragmentation (i). Two diagnostic ions at m/z 227 (ii) and m/z 304 (iii) were produced from the modification group; Structural examples of b fragment ion, y fragment ion with the intact modification group and the y fragment ion produced from the neutral loss of biotin tag (iv); Structural examples of y fragment ion, b fragment ion with the intact modification group and the b fragment ion produced from the neutral loss of biotin tag (iv).
Figure 12:
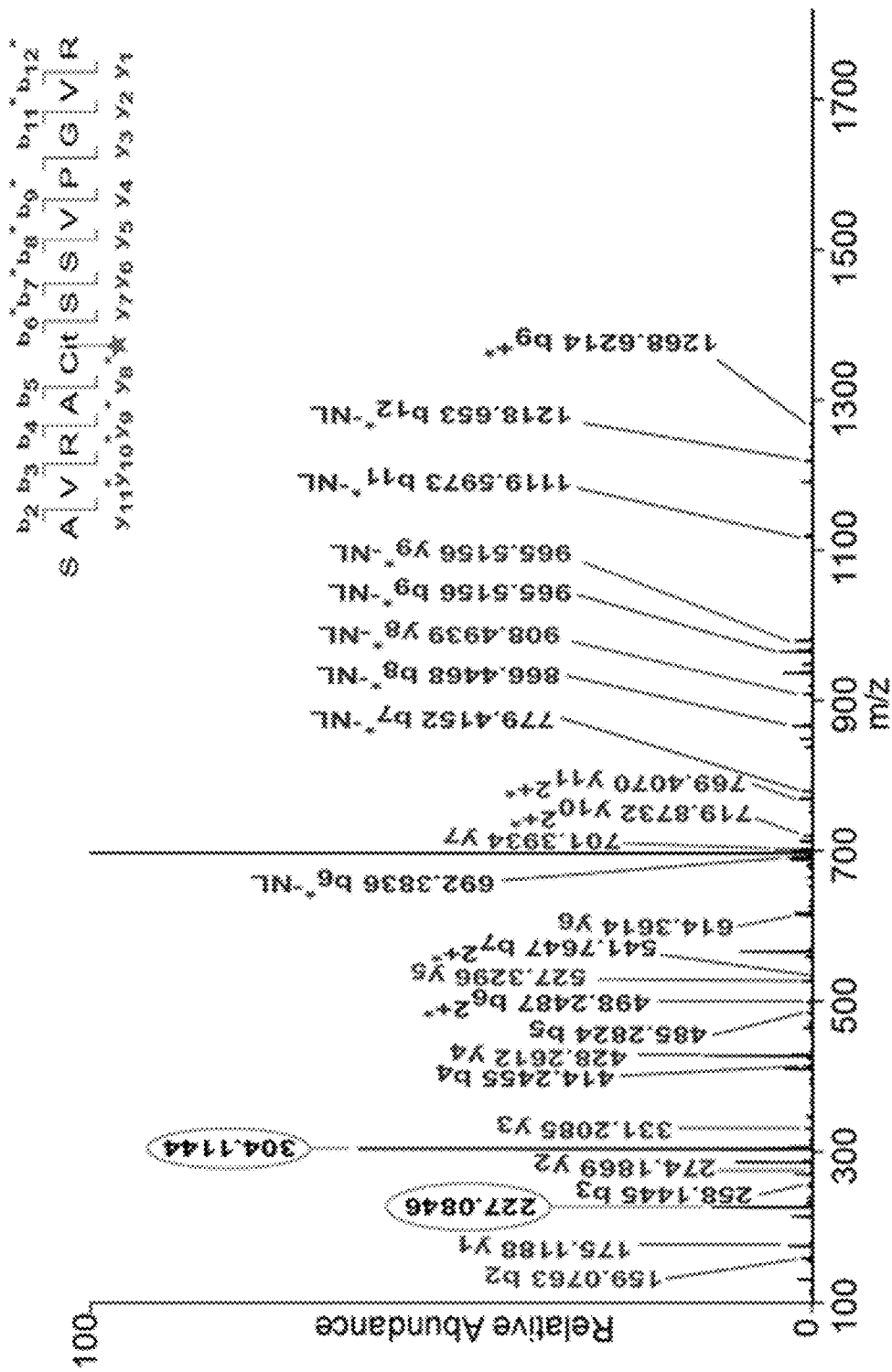
FIG. 12 shows a tandem MS spectrum of biotin tag-modified citrullinated peptide standard (SEQ ID NO:1) fragmented by HCD fragmentation technique. Two diagnostic ions at m/z 227 and m/z 304 were clearly observed. An array of b and y ions, especially ions resulted from the neutral loss of biotin tag, could be used for the identification of citrullinated peptide standard and its citrullination site. Star represents the intact chemical modification group.
Figure 13:
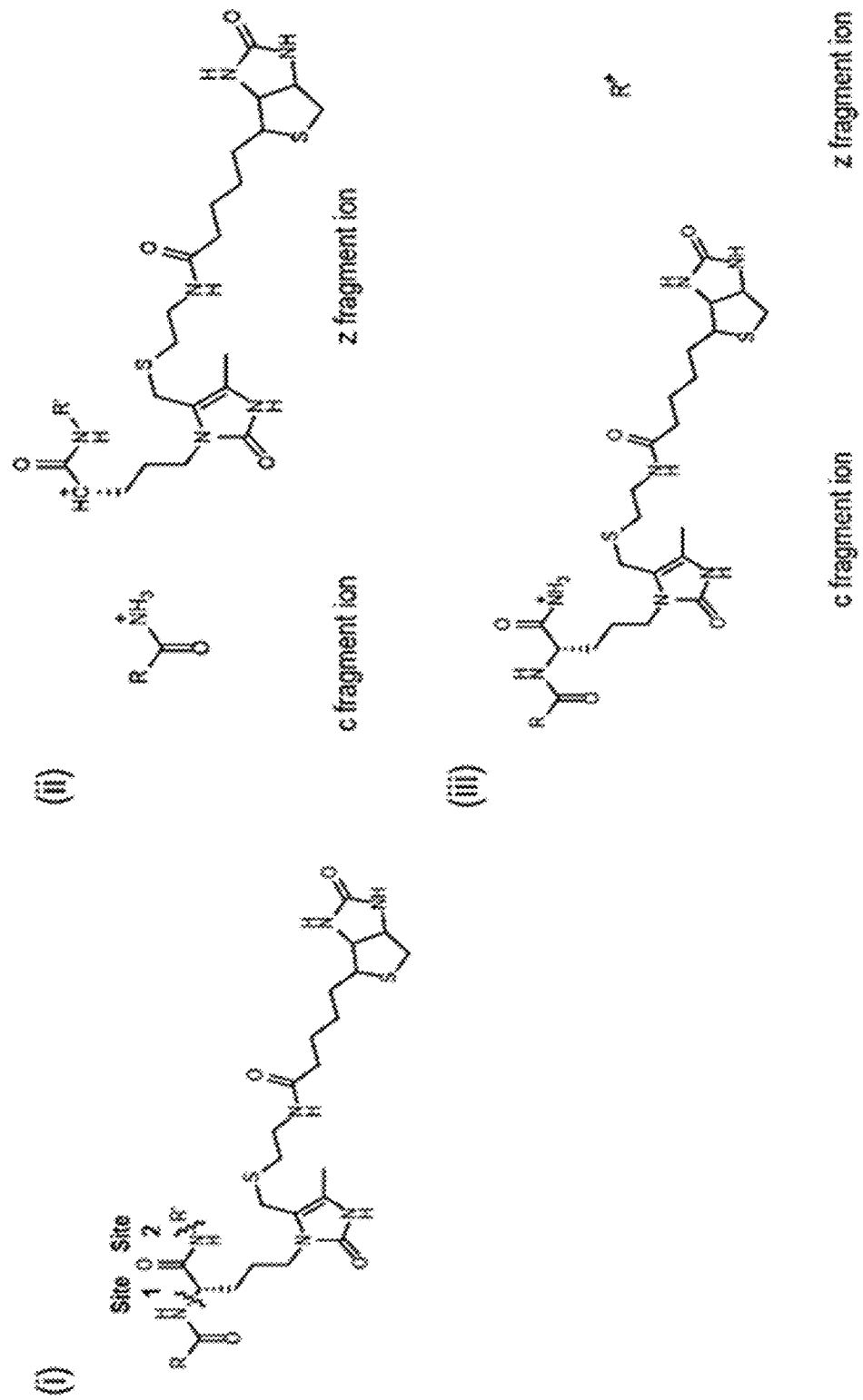
FIG. 13 shows an ETD fragmentation pattern of a biotin tag-modified citrullinated peptide. Cleavage sites of biotin tag-modified citrullinated peptide upon ETD fragmentation (i). No diagnostic ions were observed; Structural examples of c fragment ion, and z fragment ion with the intact modification group (ii); Structural examples of z fragment ion, and c fragment ion with the intact modification group (iii).
Figure 14:
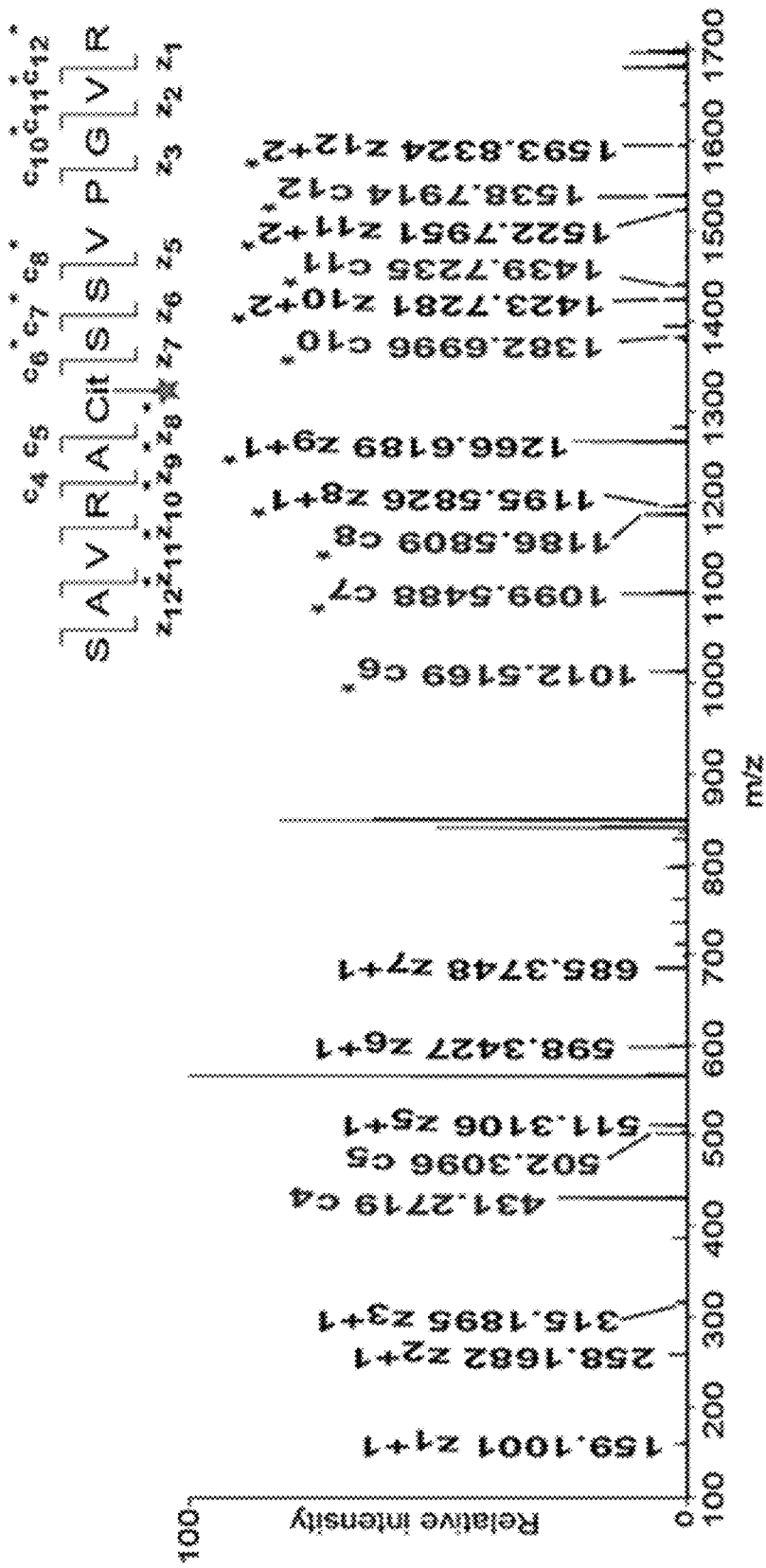
FIG. 14 shows a tandem MS spectrum of biotin tag-modified citrullinated peptide standard (SEQ ID NO:1) fragmented by ETD fragmentation technique. A large number of c and z ions, especially those c and z ions containing the intact modification group enable high-confident identification of citrullinated peptide standard and its citrullination site. Star represents the intact chemical modification group.
Figure 15:
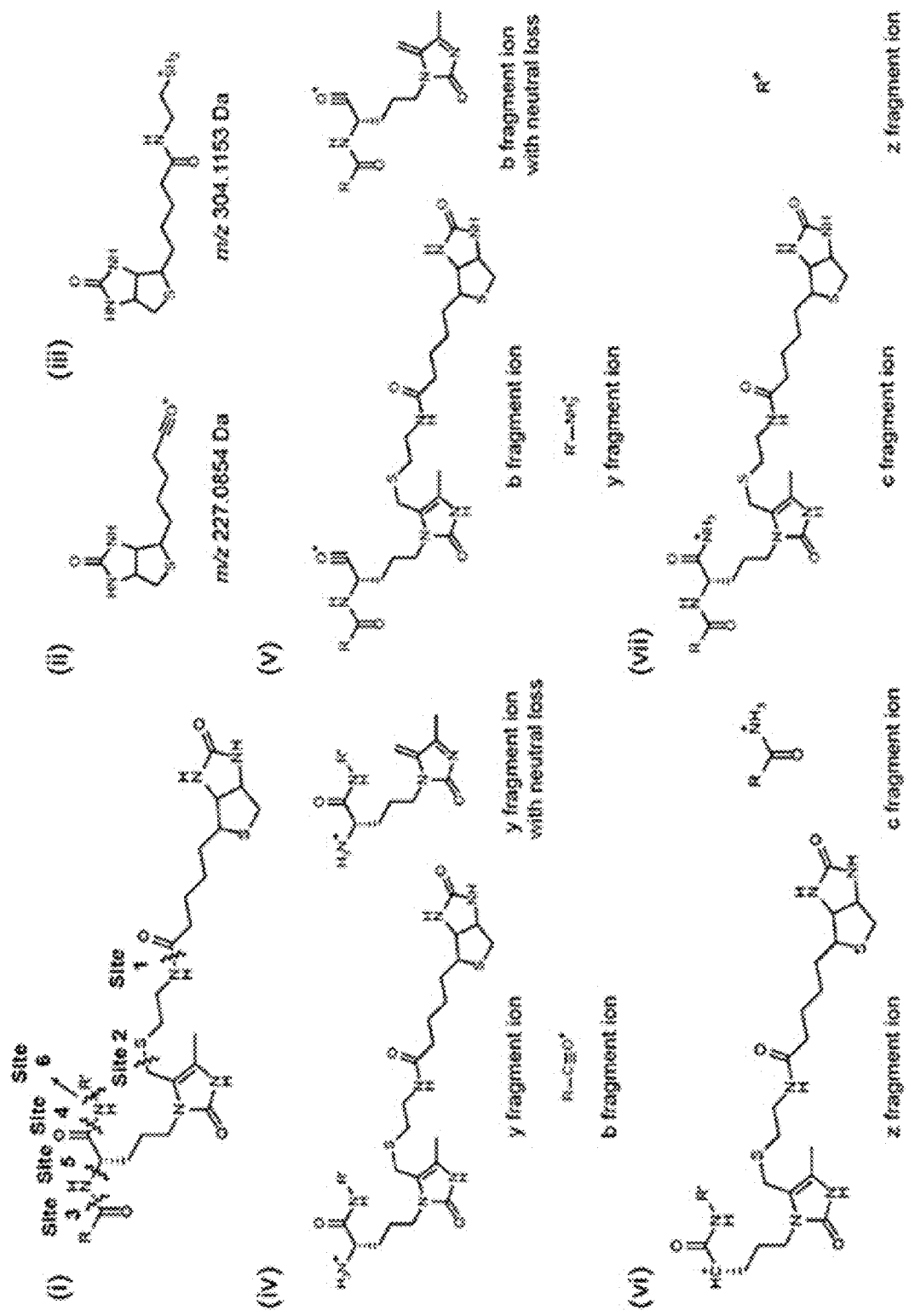
FIG. 15 shows an EThcD fragmentation pattern of biotin tag-modified citrullinated peptide. Cleavage sites of biotin tag-modified citrullinated peptide upon EThcD fragmentation (i). Two diagnostic ions at m/z 227 (ii) and m/z 304 (iii), fragment ions generated by HCD fragmentation technique (iv & v) and ETD fragmentation technique (iv & v) could be produced.
Figure 16:
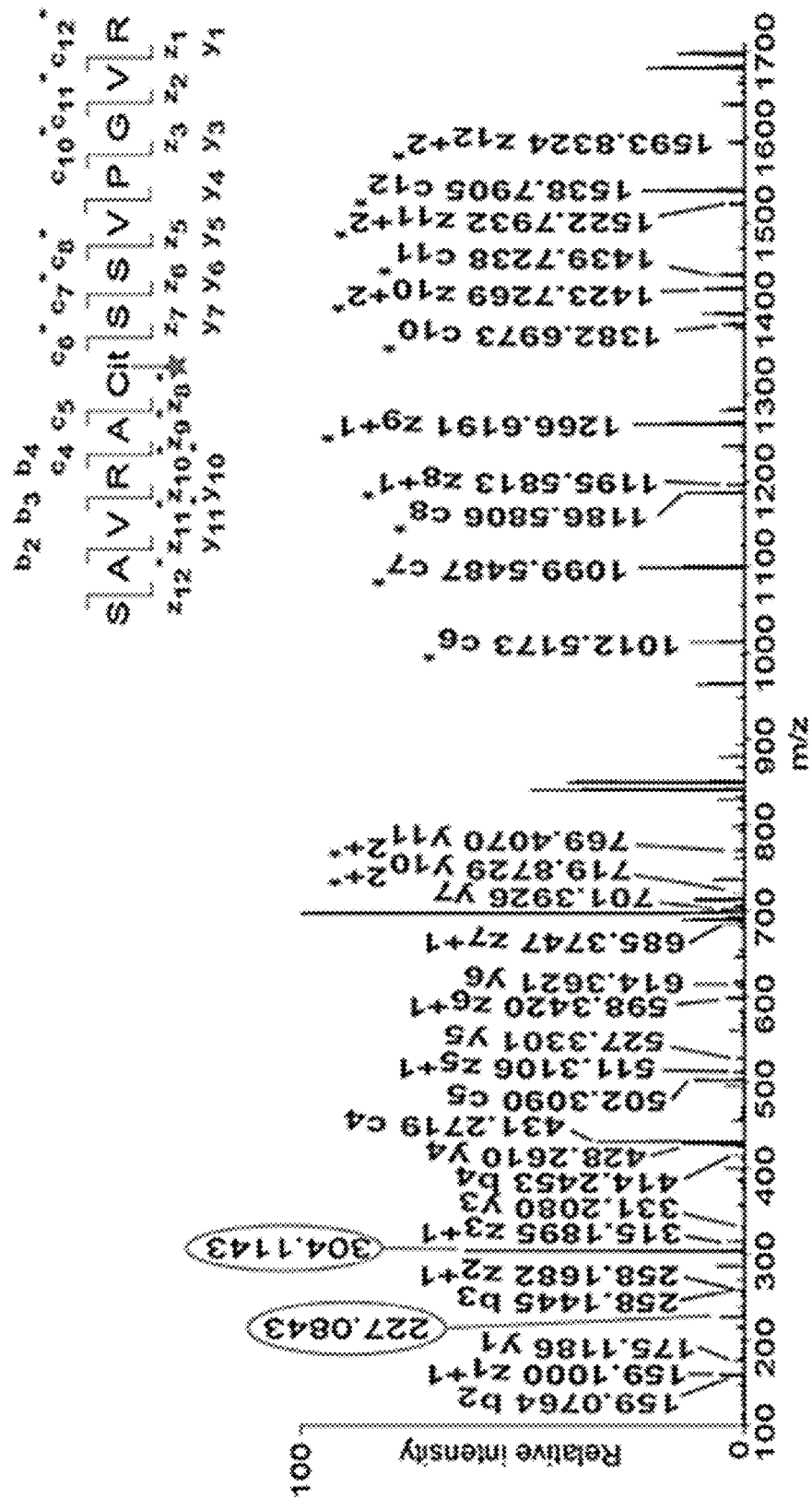
FIG. 16 shows a tandem MS spectrum of biotin tag-modified citrullinated peptide standard (SEQ ID NO:1) fragmented by EThcD fragmentation technique. Two diagnostic ions at m/z 227 and m/z 304, b and y fragment ions as well as c and z fragments were produced in one single spectrum, enabling high confident identification of citrullinated peptide standard and its citrullination sites.

The mass spectrometric fragmentation patterns of the biotin tag-modified citrullinated peptide standard was then investigated using higher-energy collisional dissociation (HCD), electron-transfer dissociation (ETD) and electron-transfer/higher-energy collision dissociation (EThcD) fragmentation techniques, respectively (FIG. 10, panel b). HCD fragmentation yielded a series of b and y peptide fragment ions including some ions resulting from the neutral loss of biotin tag group. Remarkably, two dominant ions at m/z 227 and 304 were observed, which were generated from the biotin head group and the cleavage of C—S bond linking biotin tag with imidazolone moiety, respectively (FIGS. 11 and 12). ETD fragmentation, in contrast to HCD fragmentation, did not generate ions at m/z 227 and 304, but numerous c and z fragment ions were observed, especially these fragment ions with intact modification group crucial for citrullination site assignment (FIGS. 13 and 14). EThcD fragmentation, compared to HCD and ETD fragmentation, produced two diagnostic ions at m/z 227 and 304, b and y ions as well as c and z ions in one single spectrum (FIGS. 15 and 16). These results suggested that the biotin tag-modified citrullinated peptide could generate high-quality tandem MS spectra for citrullinated peptide identification and citrullination site assignment.

Figure 17:
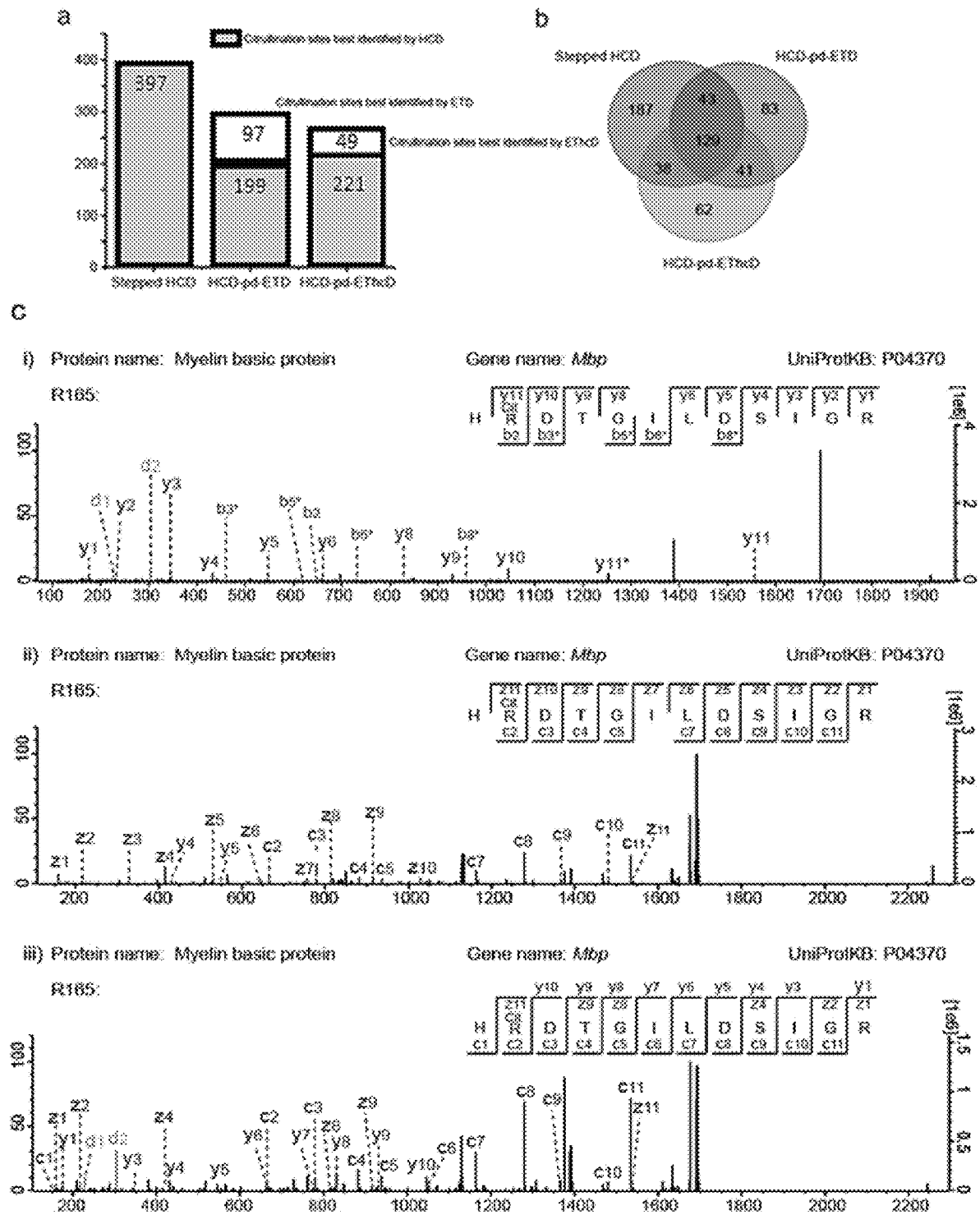
FIG. 17 shows the performance of different mass spectrometry-based fragmentation techniques for the large-scale protein citrullination analysis on the biological sample analysis. (a) High-confident citrullination sites identified from 400 μg peptides digested from mouse brain by using stepped-HCD method, HCD product ion-triggered ETD (HCD-pd-ETD) method and HCD product ion-triggered EThcD (HCD-pd-EThcD) method, respectively. (b) Venn diagram showing the overlap of citrullination sites identified by three different MS detection methods. (c) Example of the same citrullinated peptide (SEQ ID NO:2) identified by stepped-HCD method (i), HCD product ion-triggered ETD (HCD-pd-ETD) method (ii) and HCD product ion-triggered EThcD (HCD-pd-EThcD) method (iii), respectively.
Figure 18:
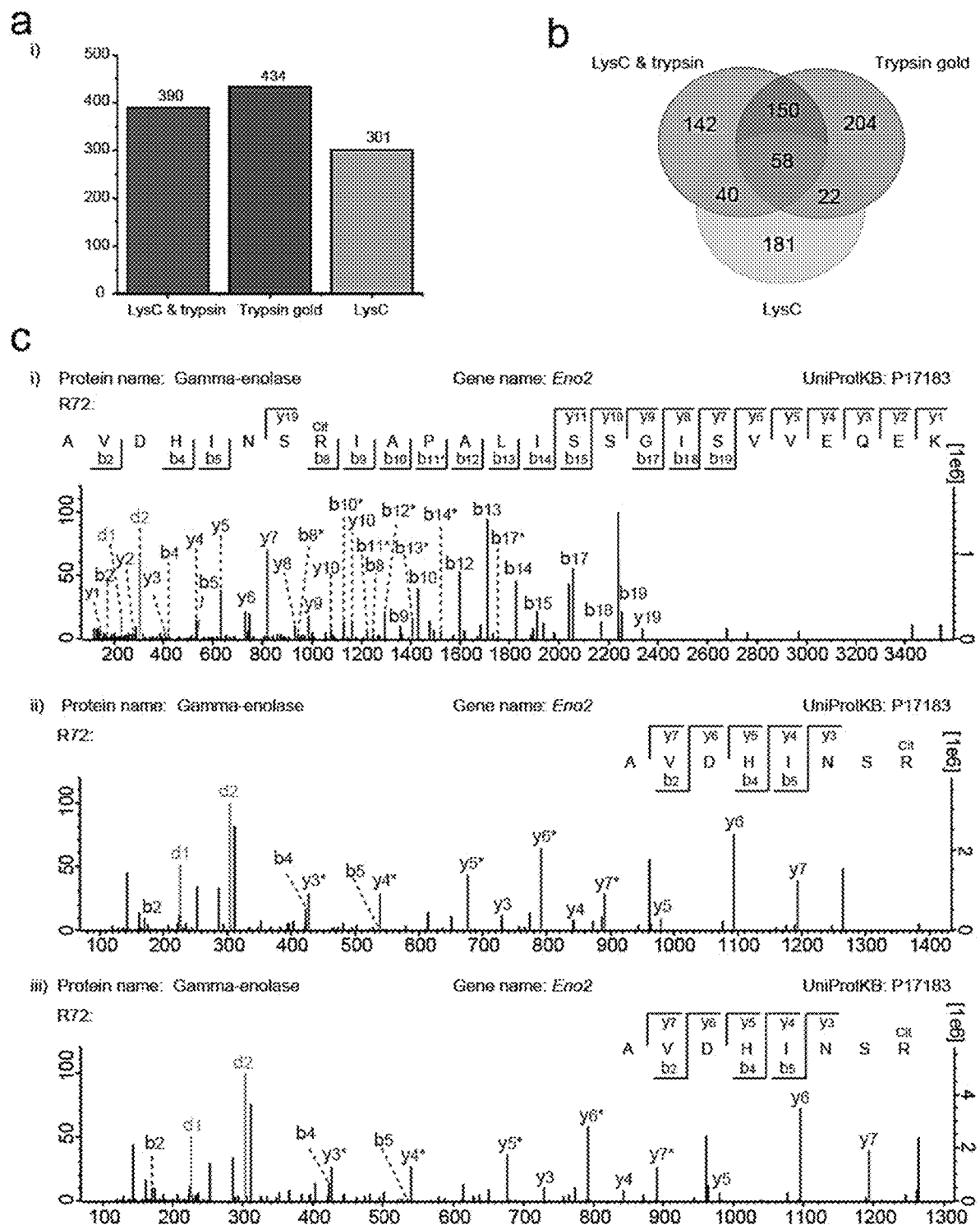
FIG. 18 shows a comparison of different enzymes used on sample preparation for the large-scale protein citrullination analysis. (a) High-confident citrullination sites identified by stepped HCD method from 400 µg peptides digested from the same mouse brain extract by enzyme LysC & trypsin gold mixture, enzyme trypsin gold and enzyme LysC, respectively. (b) Overlap of citrullinated sites identified from samples digested by three different enzymes. (c) Citrullinated peptides containing the same citrullination site were identified from the same brain extract digested by enzyme LysC enzyme (i) (SEQ ID NO:3), LysC & trypsin gold mixture (ii) (SEQ ID NO:4), and enzyme trypsin gold (iii) (SEQ ID NO:4), respectively.
Figure 19:
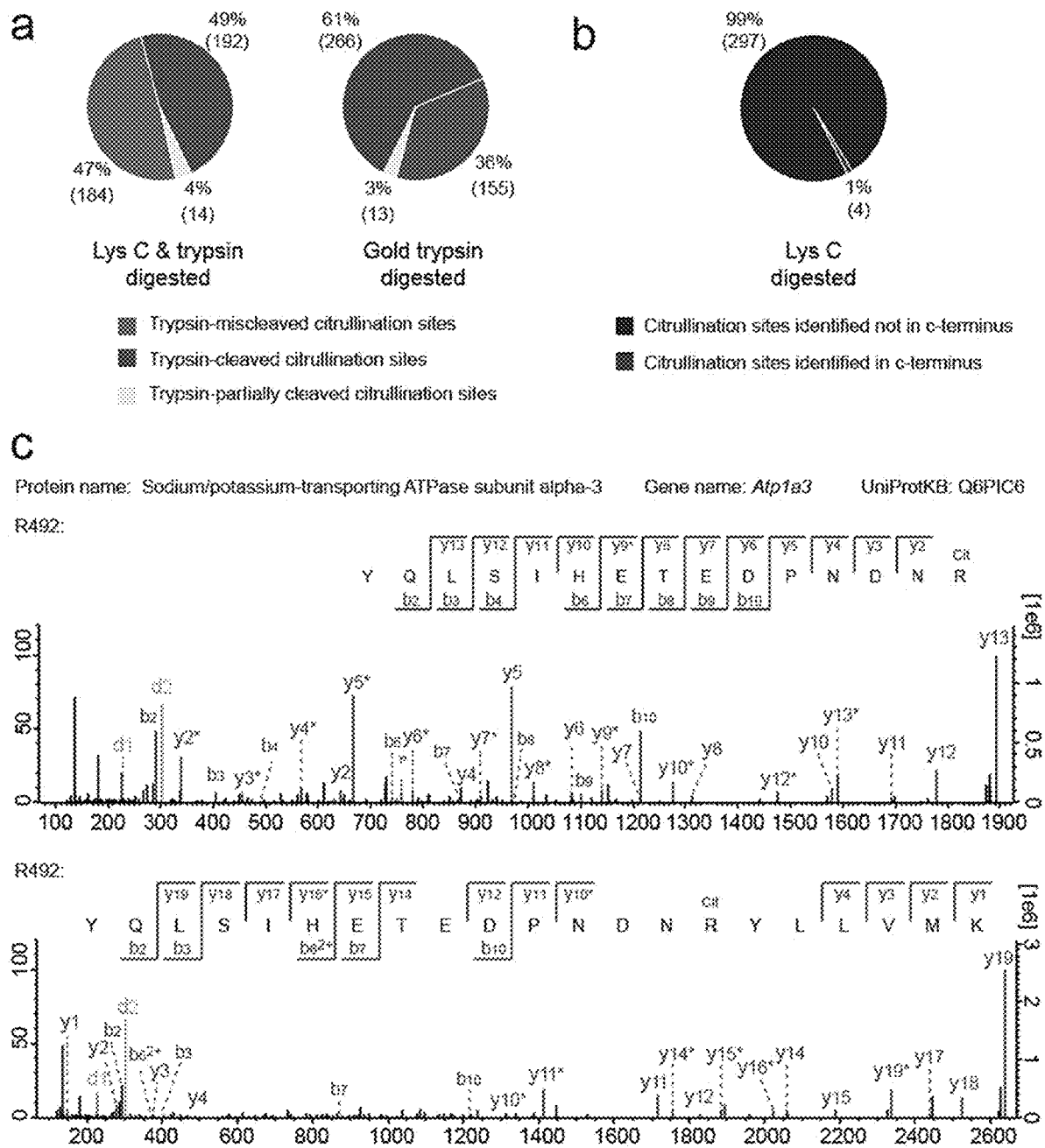
FIG. 19 shows citrullination sites able to be trypsin-cleavable in vitro. (a) Pie charts showed that more than 50% of identified citrullination sites could be cleaved by trypsin and annotated at the C-terminus of identified citrullinated peptides. (b) More than 99% of identified citrullination sites from LysC-digested sample were not at the C-terminus of identified citrullinated peptide, suggesting that citrullination sites identified at peptide C-terminus were not artificially induced upon sample preparation. (c) An example of the identified citrullination site, which was partially cleaved, from the mouse brain sample digested by LysC & trypsin. Two peptides (SEQ ID NO:5 (top) and SEQ ID NO:6) (bottom)) containing the same citrullination site were simultaneously identified from the identical sample.

The performance of the method was tested on complex biological samples, such as mouse brain, which has been reported to show high level of citrullination modification. Several MS detection strategies, including stepped-HCD, HCD product ion-triggered ETD (HCD-pd-ETD) and HCD product ion-triggered EThcD (HCD-pd-EThcD), were compared and it was found that all methods were suited for citrullination analysis though more citrullinated peptides could be identified by stepped HCD primarily due to the shorter duty cycle time (FIG. 17). Furthermore, it was noticed that a large number of citrullinated peptides with C-terminal citrulline residue were identified with high confidence, which is in contrast with a common understanding about protein citrullination that trypsin cannot cleave after the citrulline residue. To further investigate this contradictory result, the method was applied to analyze three peptide samples digested from the same mouse brain protein extract by trypsin, LysC and trypsin/LysC mixture, respectively (FIG. 18, panels a and b). For some citrullination sites, different citrullinated peptides were identified from the LysC-digested sample and trypsin or LysC/trypsin-digested sample (FIG. 18, panel c). Meanwhile, for the LysC-digested sample, few citrullinated peptides were identified with C-terminal citrulline residue. If treated by trypsin or LysC/trypsin mixture, more than 50% of identified citrullinated peptides had the citrulline residue at the C-terminus (FIG. 19). These results suggested that some citrullination sites were trypsin-cleavable in vitro though the mechanism is still uncertain.

Figure 20:
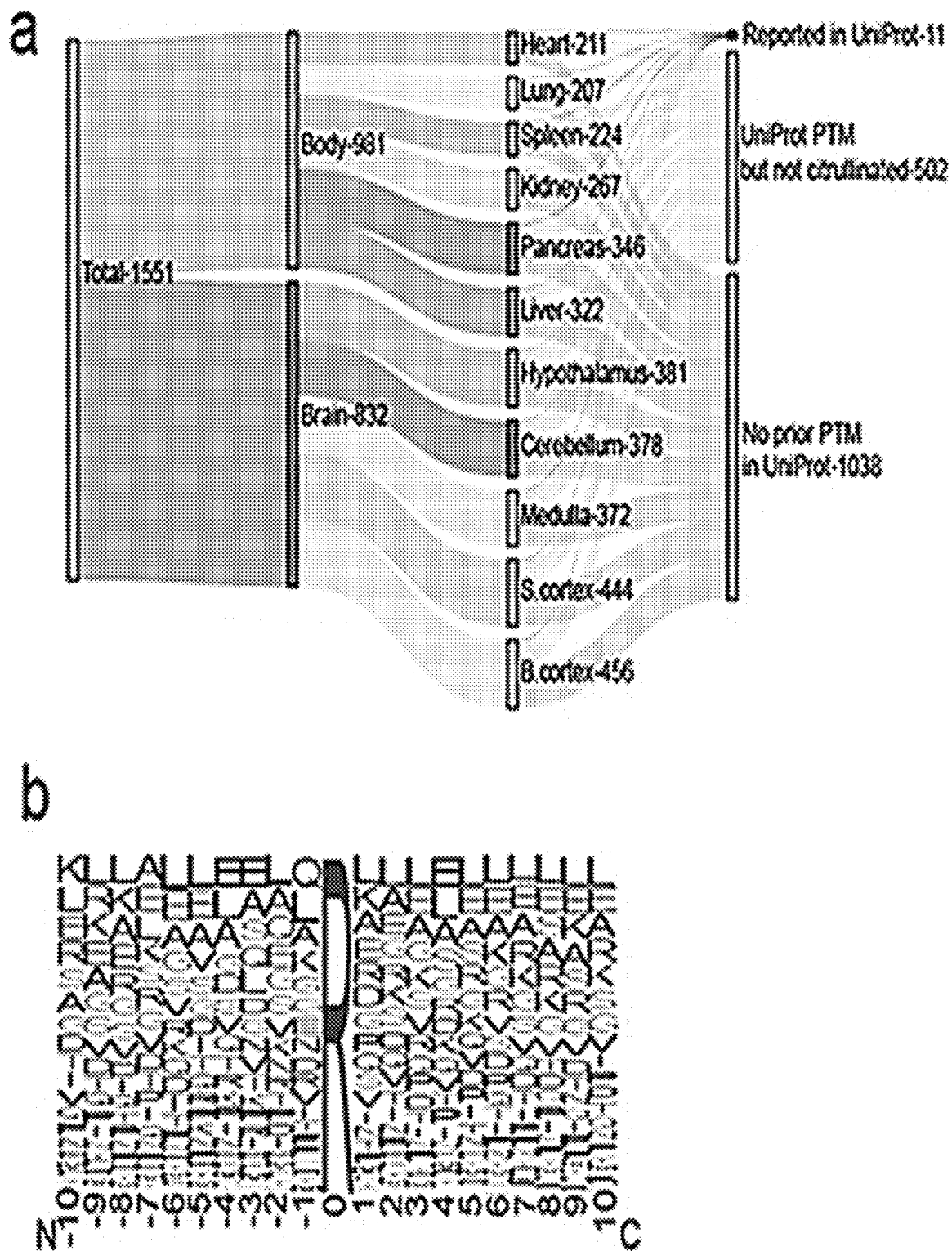
FIG. 20 shows a mouse tissue-specific protein citrullination analysis. (a) Unique citrullinated proteins identified with high confidence from mice (n=3). (b) Citrullination motif analysis of identified citrullination sites from mouse tissues.
Figure 21:
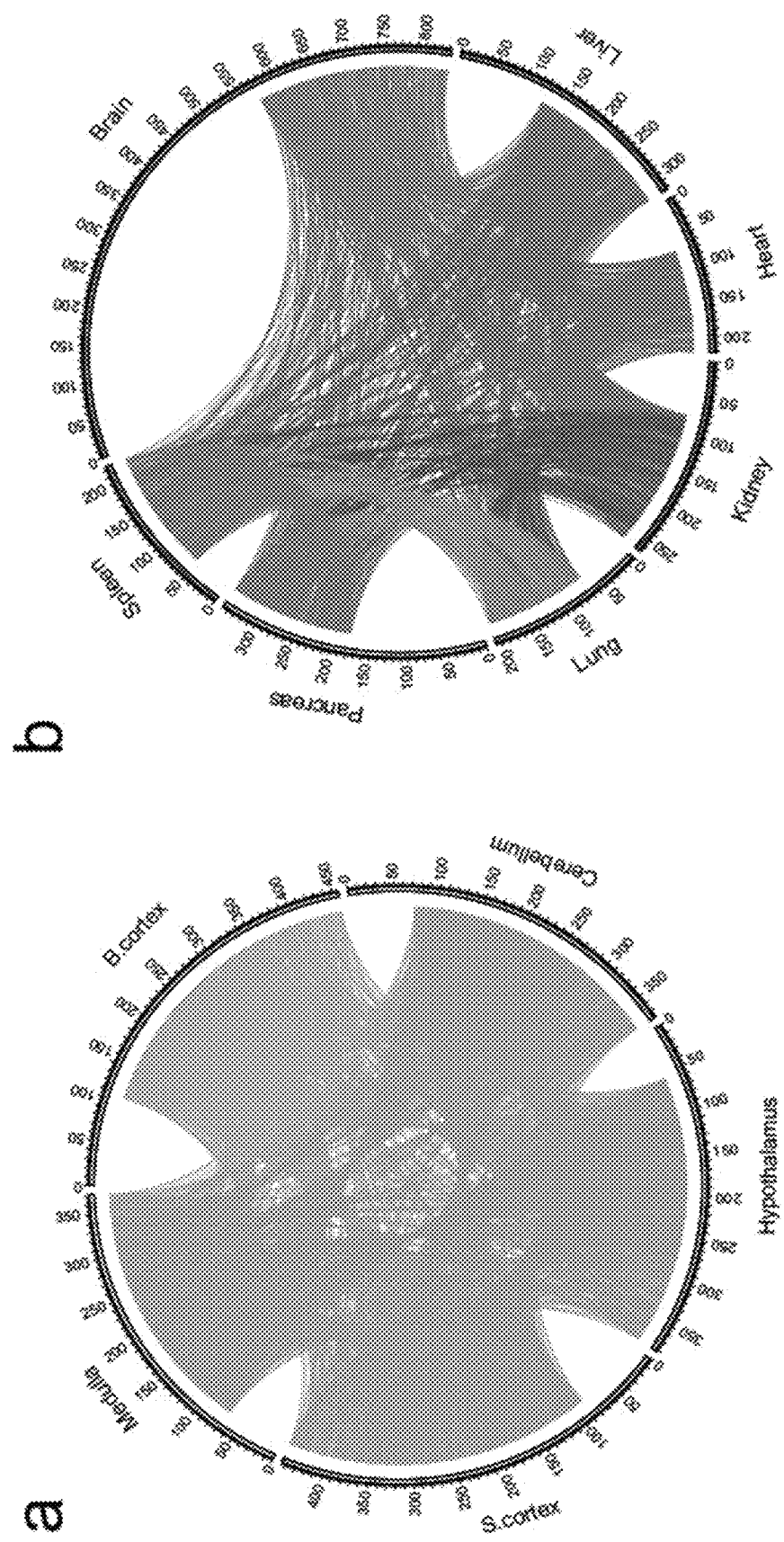
FIG. 21 shows a mouse-tissue specific distribution of citrullinated proteins. (a) The overlap of citrullinated proteins identified from different mouse brain regions. No apparent region-specific distribution pattern was identified. (b) The overlap of citrullinated proteins identified from mouse brain and other organs. Poor overlap between citrullinated proteins identified from brain and other organs was observed.
Figure 22:
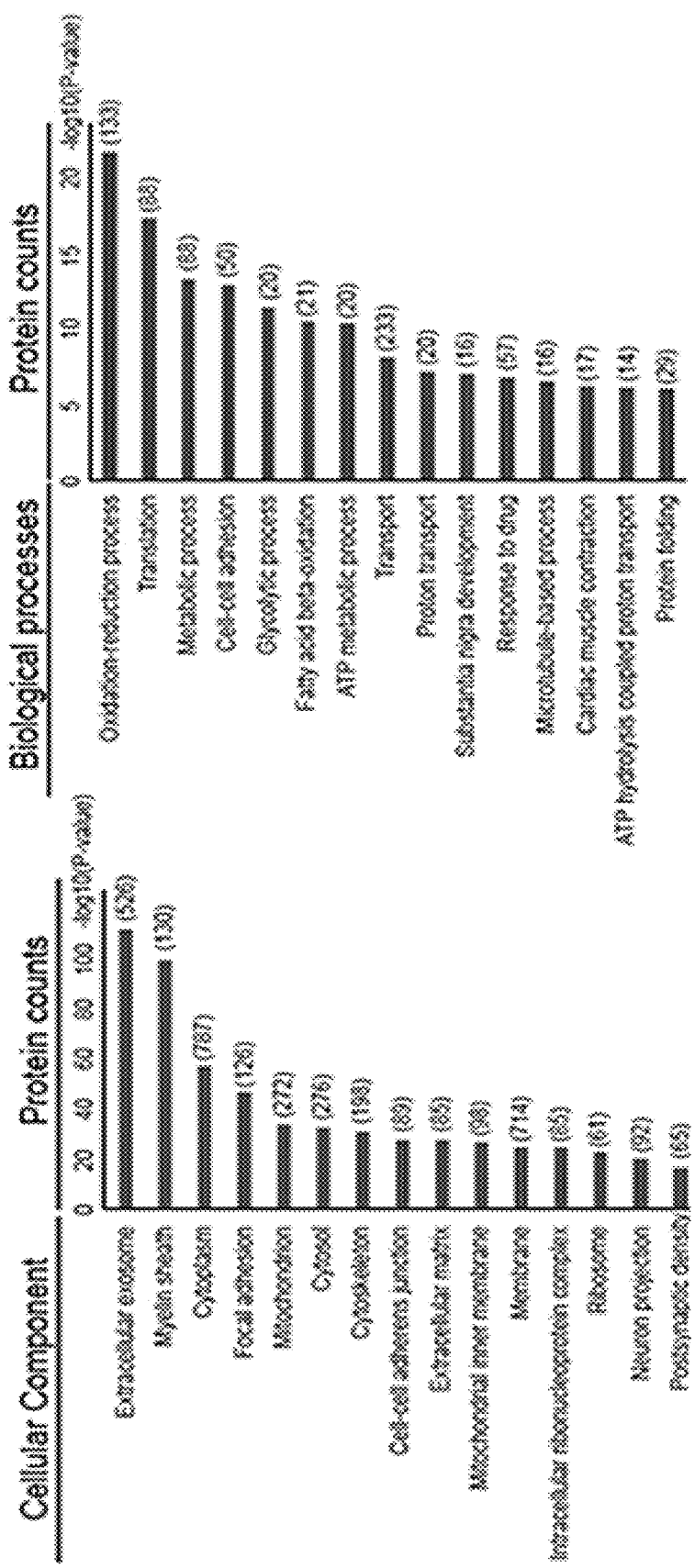
FIG. 22 shows gene ontology (GO) enrichment analysis of cellular component and biological processes of mouse-tissue citrullinated proteins.

Next, the method was applied to mouse tissue-specific protein citrullination analysis. In total, 1198 unique citrullinated proteins and 618 citrullination sites were identified with high confidence (FIG. 20, panel a). Protein citrullination showed distinct tissue-specific distribution patterns. Compared to other organs, more citrullinated proteins were identified from the brain although no apparent distribution pattern was observed from multiple brain regions. The poor overlap of citrullinated proteins was observed between these organs (FIG. 21). Citrullination motif analysis revealed that there was no conserved amino acid sequence flanking citrullination sites (FIG. 20, panel b). Gene ontology (GO) analysis indicated that citrullinated proteins are mainly present in cytoplasm, extracellular exosomes and membranes as well as mitochondrion, while biological process analysis showed the involvement of citrullinated proteins in diverse cellular processes, such as oxidation-reduction process, translation and transport (FIG. 22).

Figure 23:
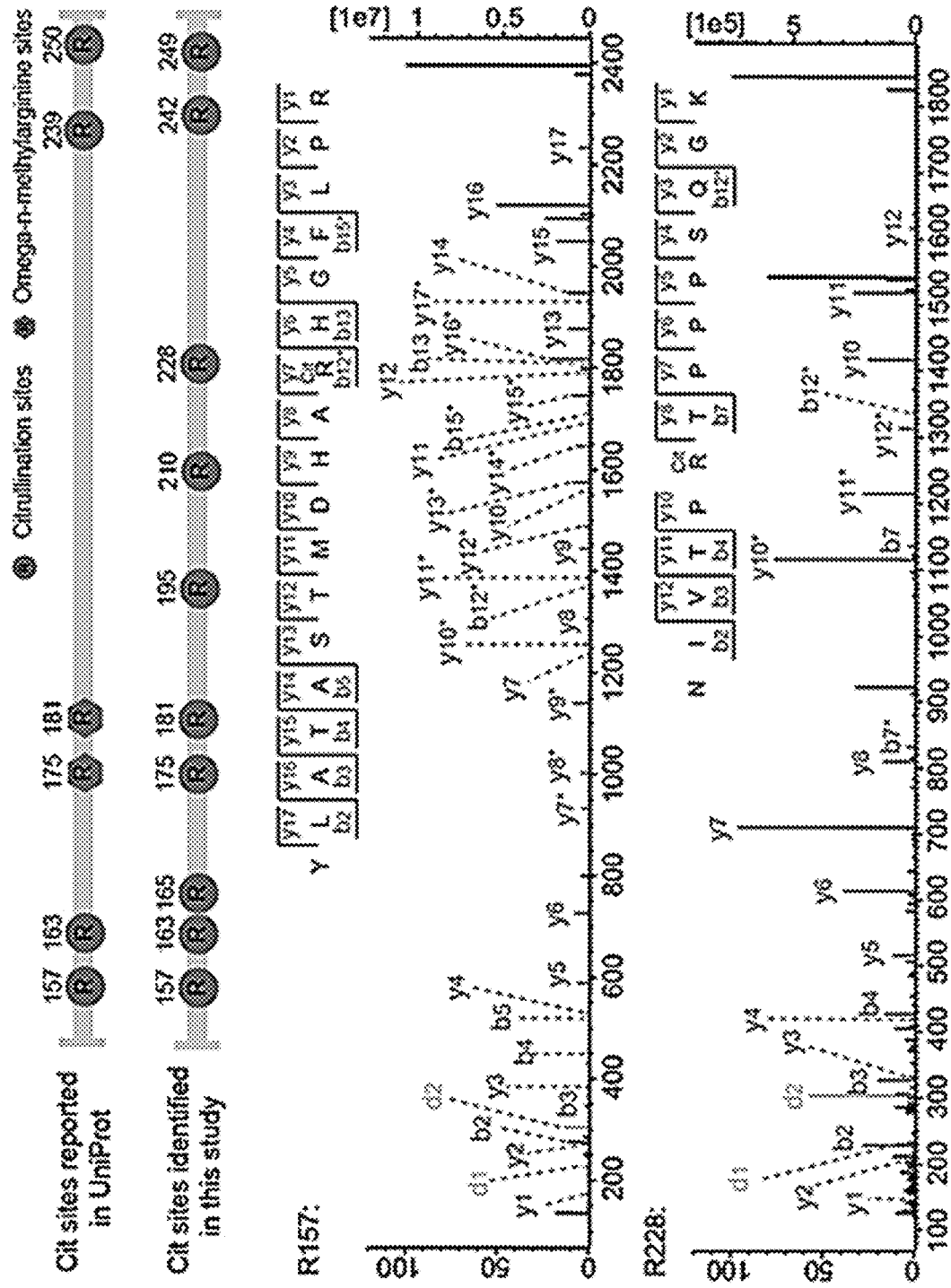
FIG. 23 shows citrullination sites of mouse myelin basic protein (P04370) reported in UniProt database and identified in this study. Tandem MS spectra of identified citrullinated peptides (SEQ ID NO:7 (top) and SEQ ID NO:8 (bottom)) containing citrullination sites at R157 and R228. Two diagnostic ions at m/z 227 (d1) and m/z 304 (d2) were observed. Fragment ions resulting from the neutral loss of biotin tag were labeled with superscript star.
Figure 24:
FIG. 24 illustrates glial fibrillary acidic protein (GFAP) identified with multiple high-confident citrullination sites from mice. (a) Citrullination sites of mouse GFAP protein reported in the UniProt database by similarity and the citrullination sites identified by the present method. (b) Tandem MS spectra of identified citrullinated peptides (SEQ ID NO:9 (top) and SEQ ID NO:10 (bottom)) containing citrullination sites at R413 and R102. Two diagnostic ions at m/z 227 (d1) and m/z 304 (d2) were observed and peptide fragment ions were annotated. Fragment ions resulting from the neutral loss of biotin tag were labeled with superscript star.
Figure 24:
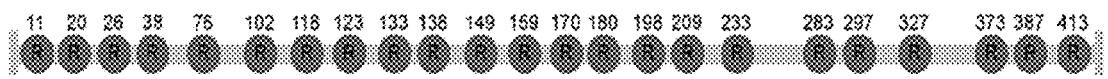
Figure 24:
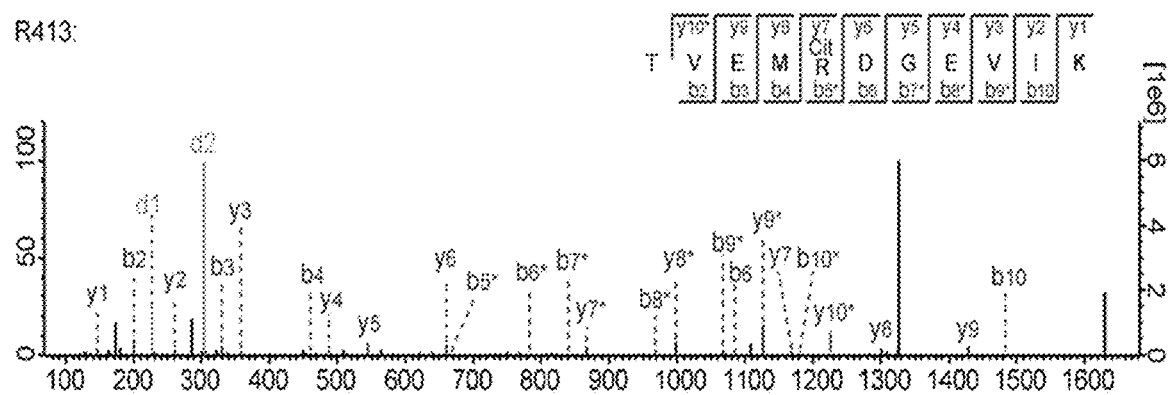
Figure 24:
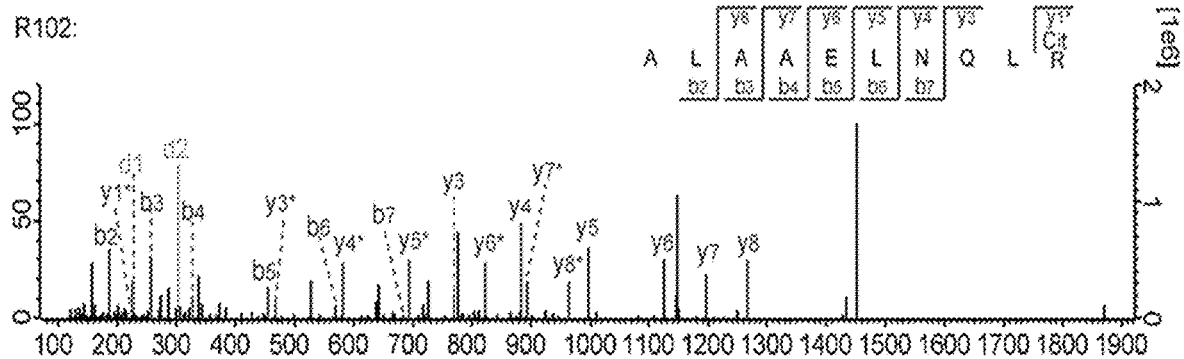

With the improved method reported here, not only were previously known citrullination sites detected, but also new citrullination sites from the reported citrullinated proteins. Taking myelin basic protein (MBP) as an example, only 4 citrulline residues are asserted by similarity in the Uniprot database. However, 10 citrullination sites were confidently identified on MBP from mouse brain tissues. Besides arginine 157 and 163, 8 new citrullination sites were assigned by their high-quality tandem MS spectra (FIG. 23). Another interesting citrullinated protein is the glial fibrillary acidic protein (GFAP), which is considered as an astrocyte-specific protein marker and involved in the astrocyte-neuron interactions. The present method pinpointed 14 citrullination sites in GFAP with high confidence, most of which have not been reported (FIG. 24).

Figure 25:
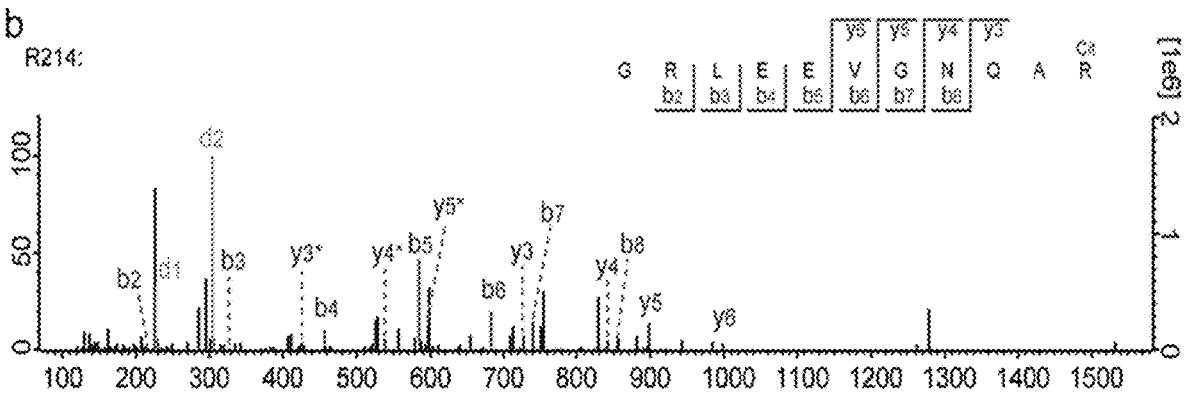
FIG. 25 illustrates at least one novel citrullination site identified from mouse protein apolipoprotein E. (a) No citrullination sites were reported on protein apolipoprotein E in the UniProt database. (b) Tandem MS spectra of identified citrullinated peptides (SEQ ID NO:11 (top) and SEQ ID NO:12 (bottom)) containing at least one citrullination site at R214. Two diagnostic ions at m/z 227 (d1) and m/z 304 (d2) were observed and peptide fragment ions were annotated. Fragment ions resulting from the neutral loss of biotin tag were labeled with superscript star.
Figure 26:
FIG. 26 illustrates at least one novel citrullination site identified from mouse microtubule-associated protein tau. (a) No citrullination sites were reported on mouse microtubule-associated protein tau in the UniProt database. (b) Tandem MS spectra of identified citrullinated peptides (SEQ ID NO:13 (top) and SEQ ID NO:14 (bottom)) containing at least one citrullination sites at R534. Two diagnostic ions at m/z 227 (d1) and m/z 304 (d2) were observed and peptide fragment ions were annotated. Fragment ions resulting from the neutral loss of biotin tag were labeled with superscript star.
Figure 26:
Figure 26:
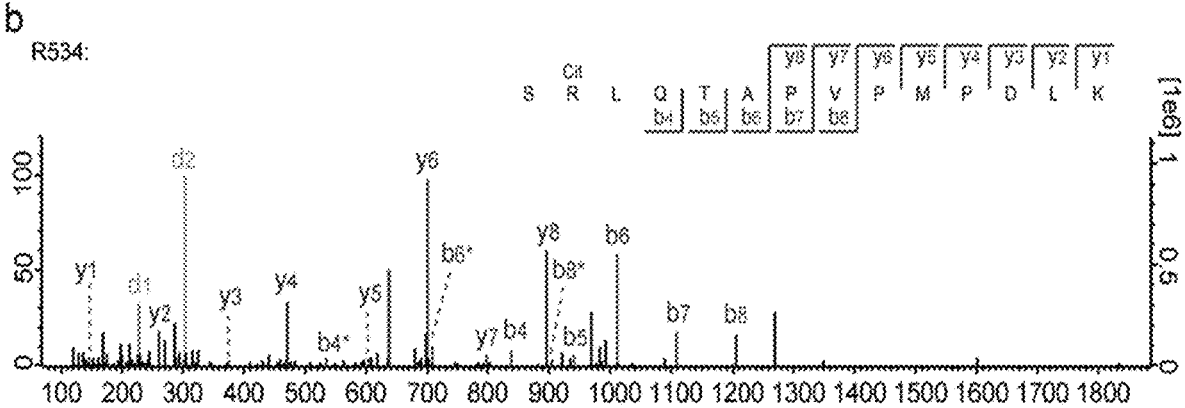
Figure 26:
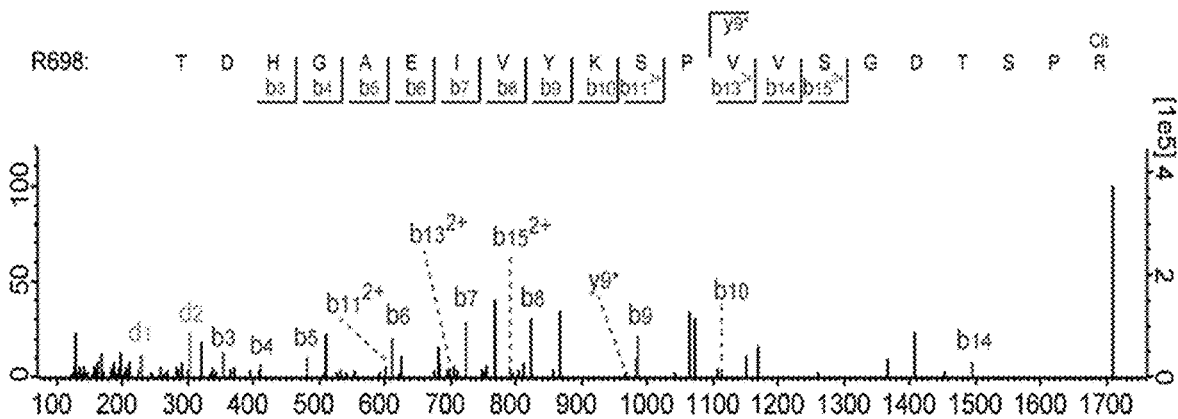
Figure 27:
FIG. 27 illustrates at least one novel citrullination site identified from mouse NAD-dependent protein deacetylase sirtuin-2. (a) No citrullination sites were reported on mouse NAD-dependent protein deacetylase sirtuin-2 in the UniProt database. (b) Tandem MS spectra of identified citrullinated peptides (SEQ ID NO:15 (top) and SEQ ID NO:16 (bottom)) containing citrullination sites at R57 and R153. Two diagnostic ions at m/z 227 (d1) and m/z 304 (d2) were observed and peptide fragment ions were annotated. Fragment ions resulting from the neutral loss of biotin tag were labeled with superscript star.
Figure 27:
Figure 27:
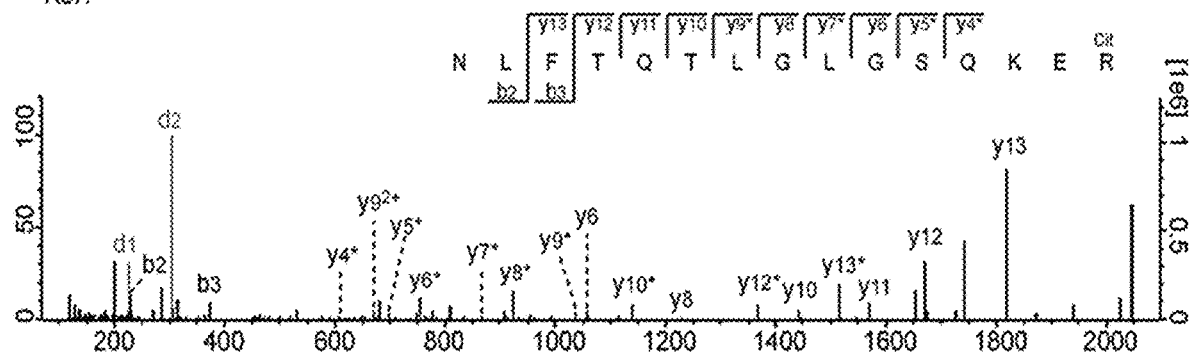
Figure 27:
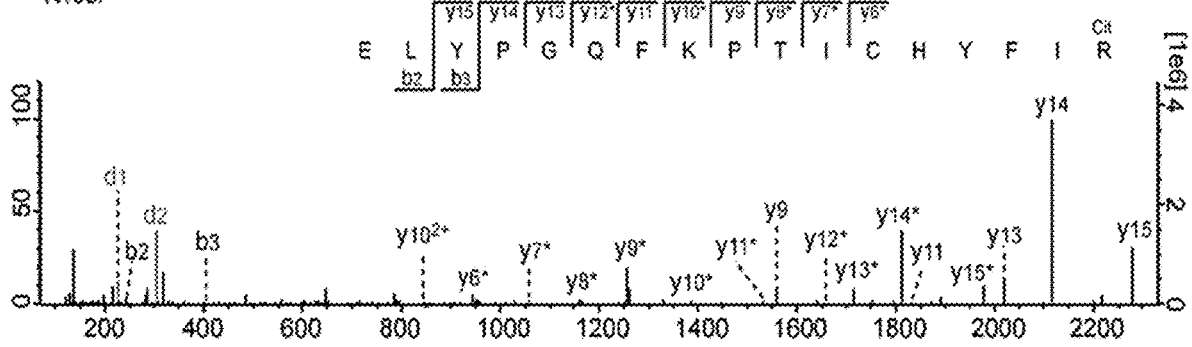

More importantly, the present method enabled the identification of many important citrullinated proteins for the first time. For example, apolipoprotein E (ApoE) is an important apolipoprotein associated with lipid metabolism and Aβ metabolism in the brain. ApoE4, one type of ApoE isoforms encoded by ε4 allele of the APOE gene, is considered as a strong risk factor of Alzheimer disease (AD). In this study, at least one new citrullination site was identified located at R214 of protein apolipoprotein E from mouse brain for the first time (FIG. 25). Another important citrullinated protein found in the mouse brain was microtubule-associated protein tau (Tau). It is well-known that hyperphosphorylation of the tau protein contributed to the pathogenesis of AD. Here, a citrullination modification was detected at least at R534, which has not been reported previously (FIG. 26). Besides those proteins, two citrullination sites at R57 and R153 were detected in NAD-dependent protein deacetylase sirtuin-2, which functions as an essential enzyme for the deacetylation of histones, tubulin and many transcription factors, and therefore plays a critical role in many biological processes (FIG. 27).

Figure 28:
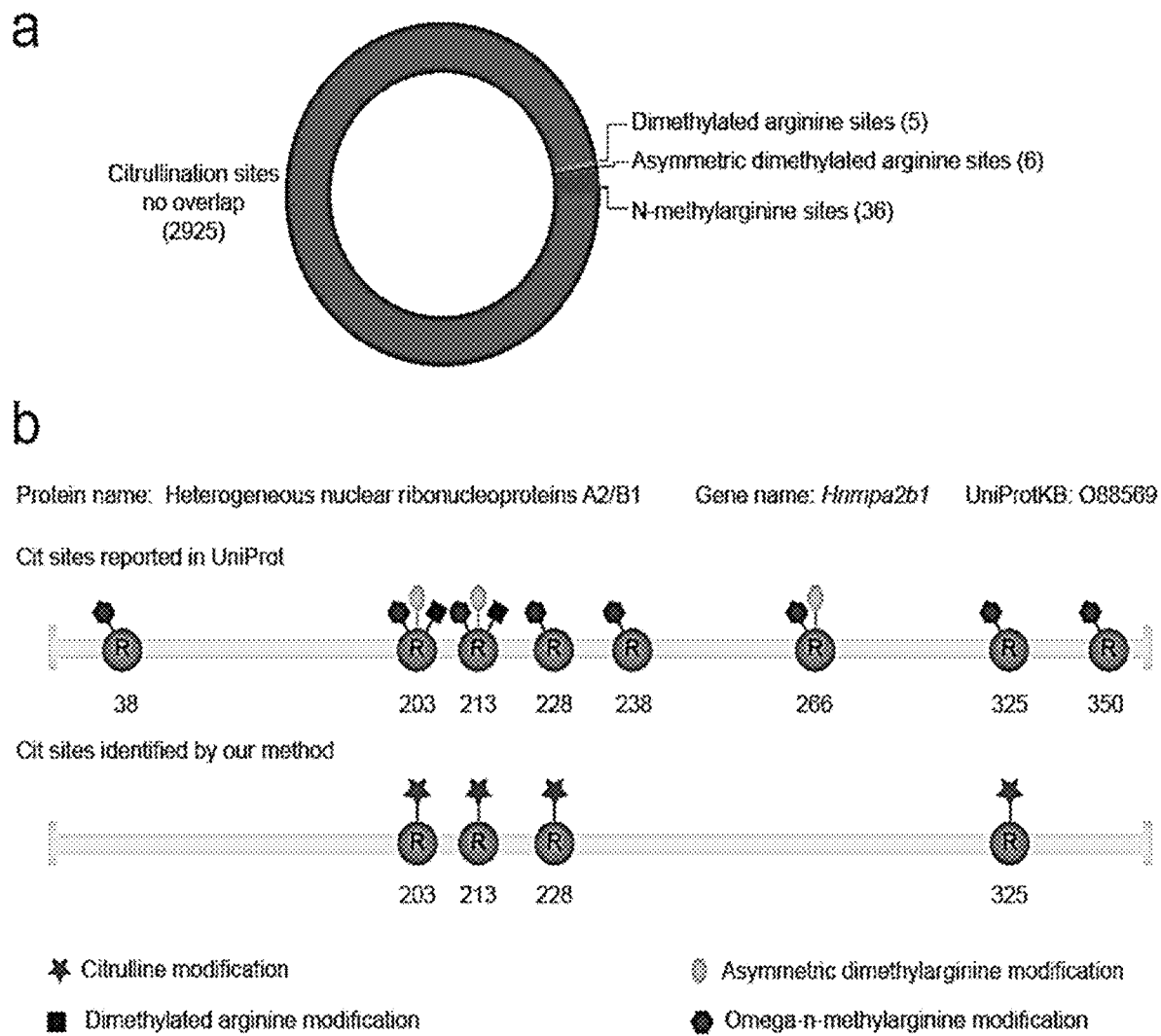
FIG. 28 illustrates ETD fragmentation pattern of a biotin tag-modified citrullinated peptide. (a) Cleavage sites of biotin tag-modified citrullinated peptide upon ETD fragmentation (i). No diagnostic ions were observed; Structural examples of c fragment ion, and z fragment ion with the intact modification group (ii); Structural examples of z fragment ion, and c fragment ion with the intact modification group (iii). (b) Tandem MS spectrum of biotin tag-modified citrullinated peptide standard fragmented by ETD fragmentation technique. A large number of c and z ions, especially those c and z ions containing the intact modification group enable high-confident identification of citrullinated peptide standard and its citrullination site. Star represents the intact chemical modification group.

It was further observed that citrullination modification was co-localized with some arginine methylation modifications at some arginine residues, especially the omega-n-methylarginine modification (FIG. 28, panel a). Thirty identified citrullination sites were overlapped with the omega-n-methylarginine sites in UniProt database, such as the R175 and R181 at MBP, and R20 at GFAP. Additionally, it was observed that 4 types of arginine modifications occurred at the R203 and R213 of the heterogeneous nuclear ribonucleoproteins A2/B1(Hnrnpa2b1), suggesting the presence of potential crosstalk between these arginine PTMs (FIG. 28, panel b).

Figure 29:
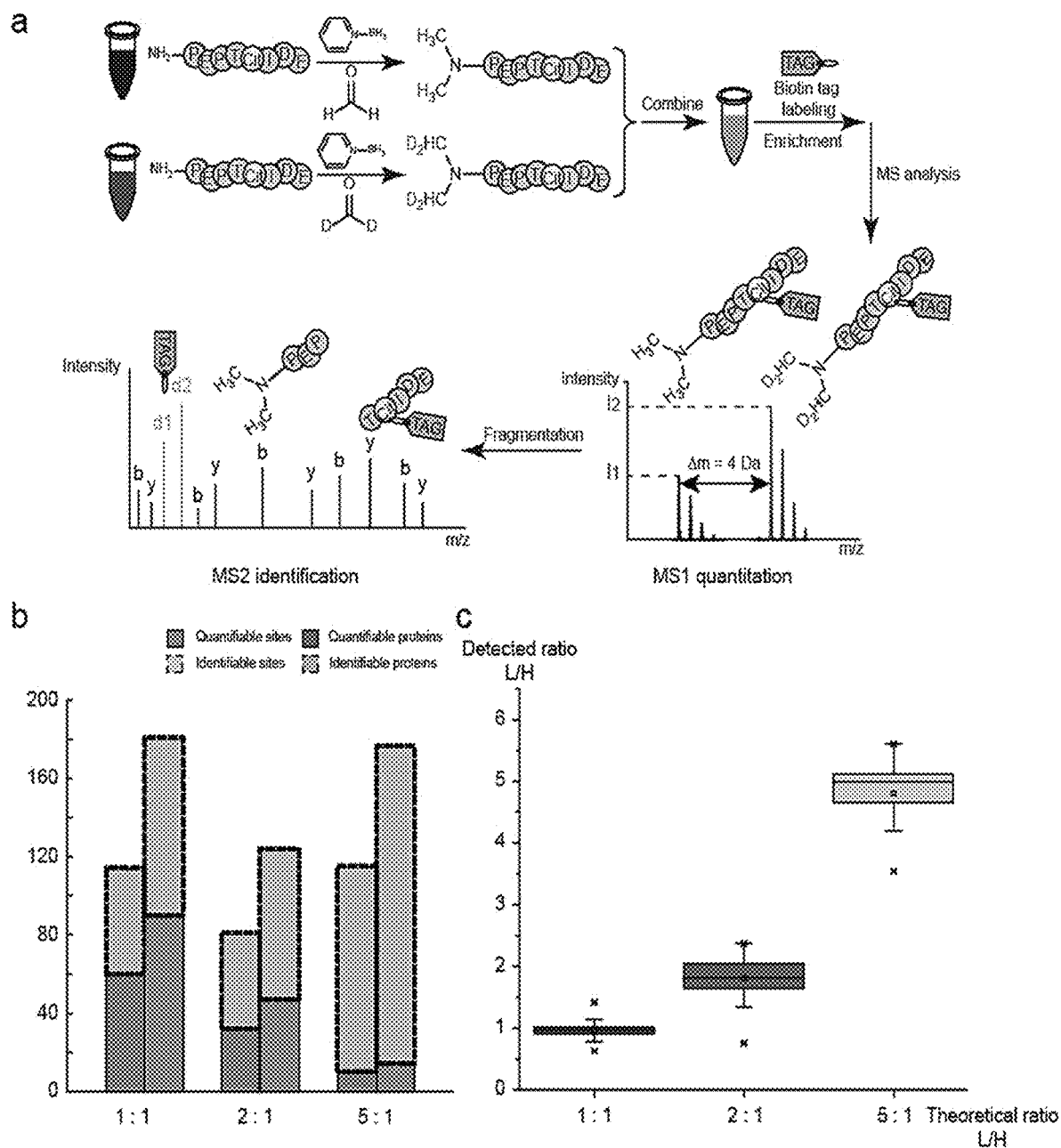
FIG. 29 describes development of a novel MS-based method for simultaneously qualitative and quantitative protein citrullination analysis. (a) Schematic diagram showing the principle of the new MS-based method. The biotin tag-based method for qualitative protein citrullination analysis is integrated with the stable isotopic dimethylation labeling strategy, enabling simultaneously qualitative and quantitative protein citrullination analysis from different biological samples. (b) Performance of the novel method was evaluated with biological samples. Due to the increased complexity of $MS^1$ spectra caused by the isotopic labeling, only half of the identified citrullinated peptides could be quantified. (c) Reliable relative quantitation accuracy could be obtained for the quantifiable citrullinated peptides from biological samples.
Figure 30:
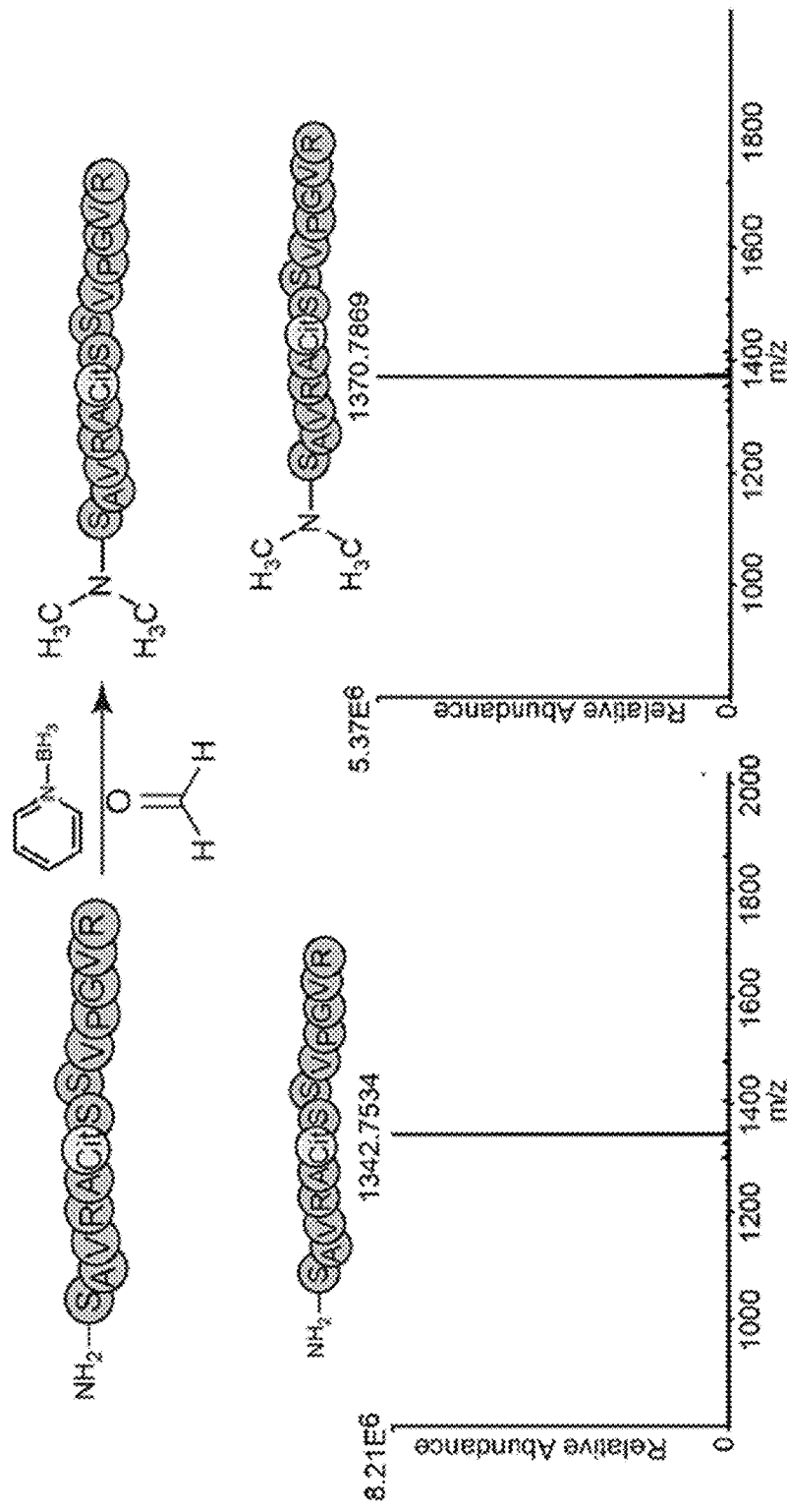
FIG. 30 shows dimethyl labeling of a citrullinated peptide standard (SEQ ID NO:1). No side reaction when labeling in $H_2O$ and complete labeling was observed.
Figure 31:
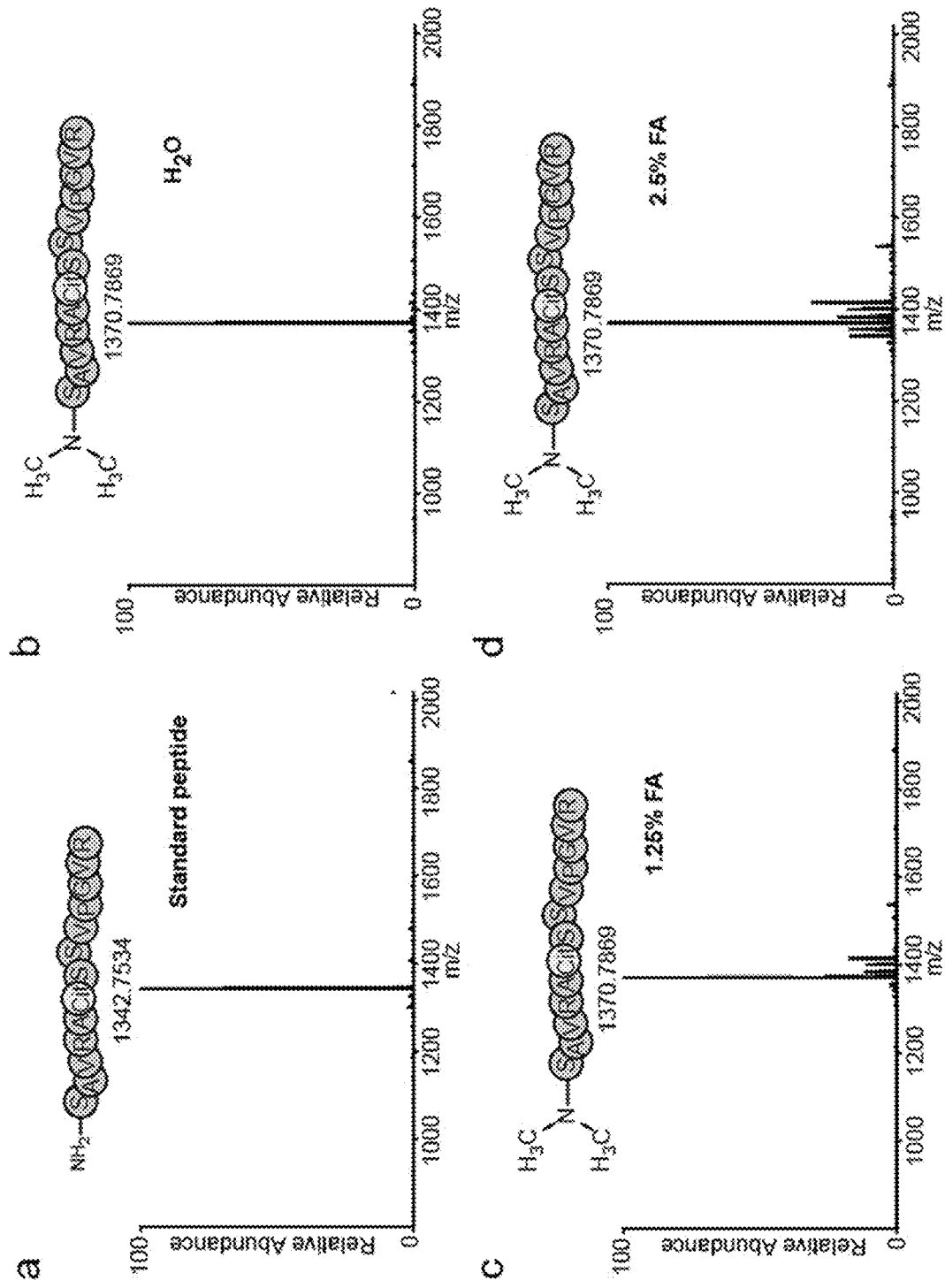
FIG. 31 illustrates an optimization of a reaction buffer for the dimethyl labeling of citrullinated peptides by using the citrullinated peptide standard (SEQ ID NO:1). Citrullinated peptide can be dimethylated in water solution without apparent side effect. (a) Synthesized citrullinated peptide standard detected by MALDI-LTQ orbitrap MS. Dimethylation of citrullinated peptide standard in water solution (b), 1.25% FA/water solution (c) and 2.5% FA/water solution (d).
Figure 32:
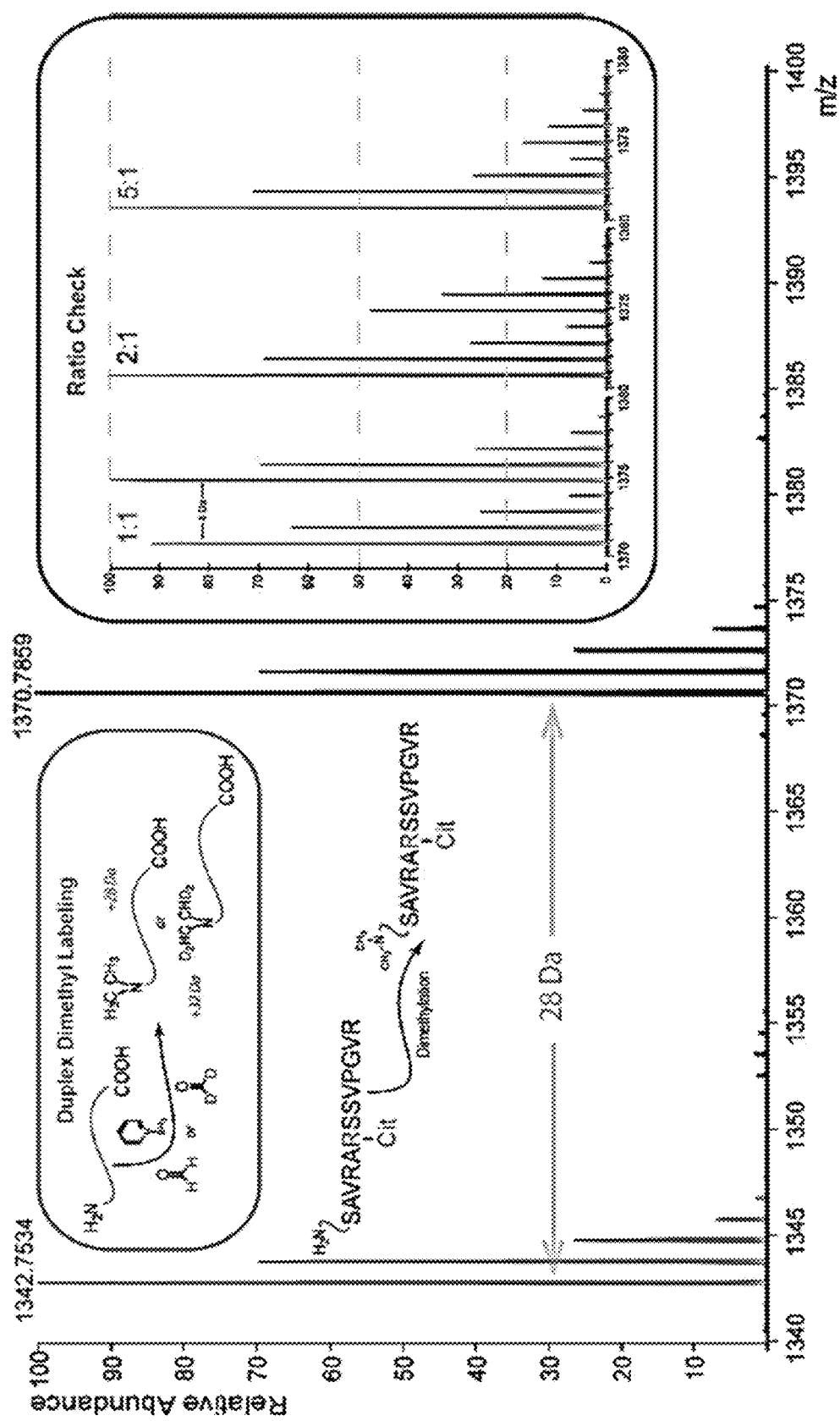
FIG. 32 shows quantitative accuracy of dimethyl labeling of a citrullinated peptide standard.
Figure 33:
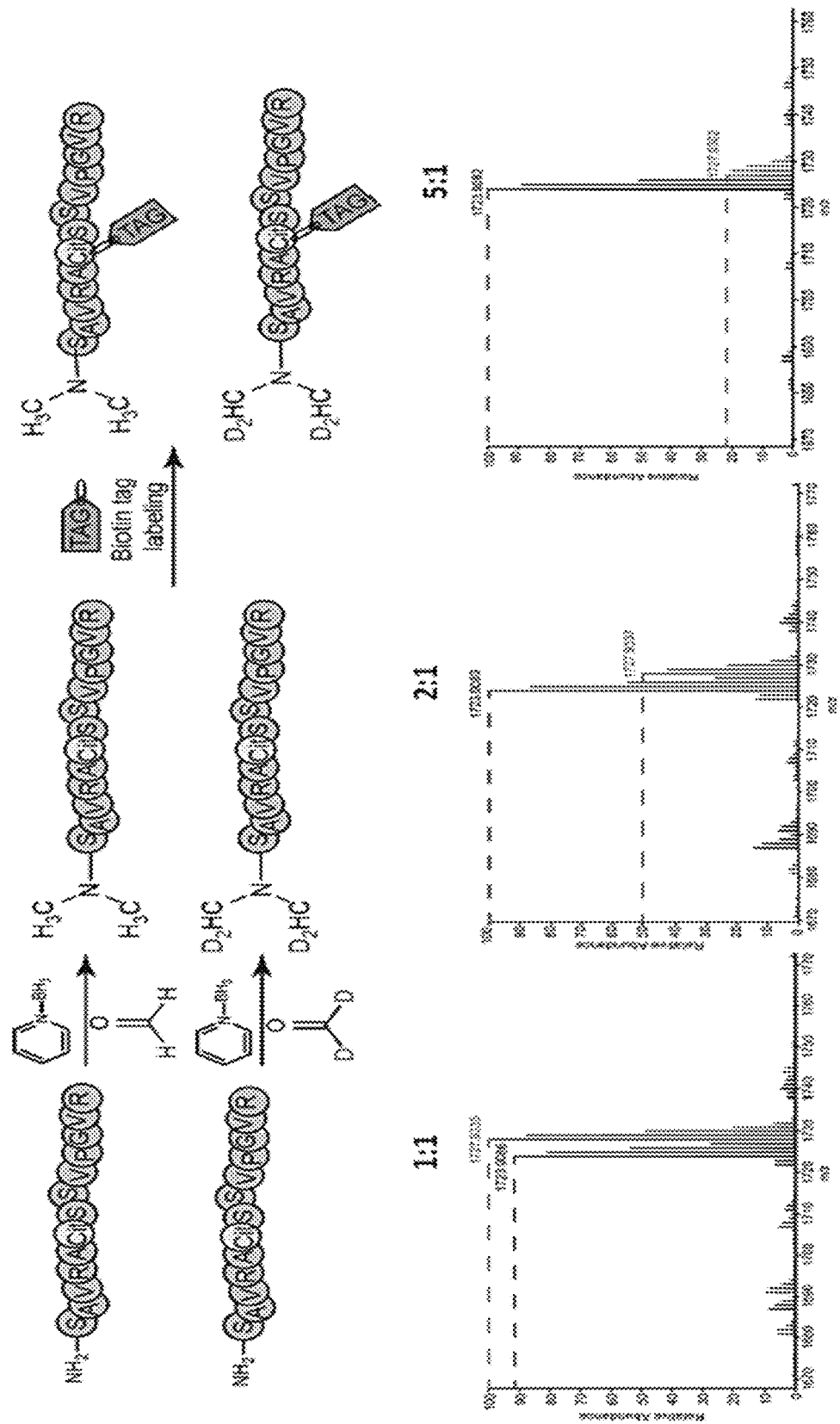
FIG. 33 shows a test of quantification accuracy using a citrullinated peptide standard (SEQ ID NO:1) after the combination of a biotin tag labeling method in conjunction with a dimethyl labeling strategy. Altering the relative amounts of the different isotopically labeled peptides (1:1, 2:1, and 5:1) can be seen in the resulting MS spectra.
Figure 34:
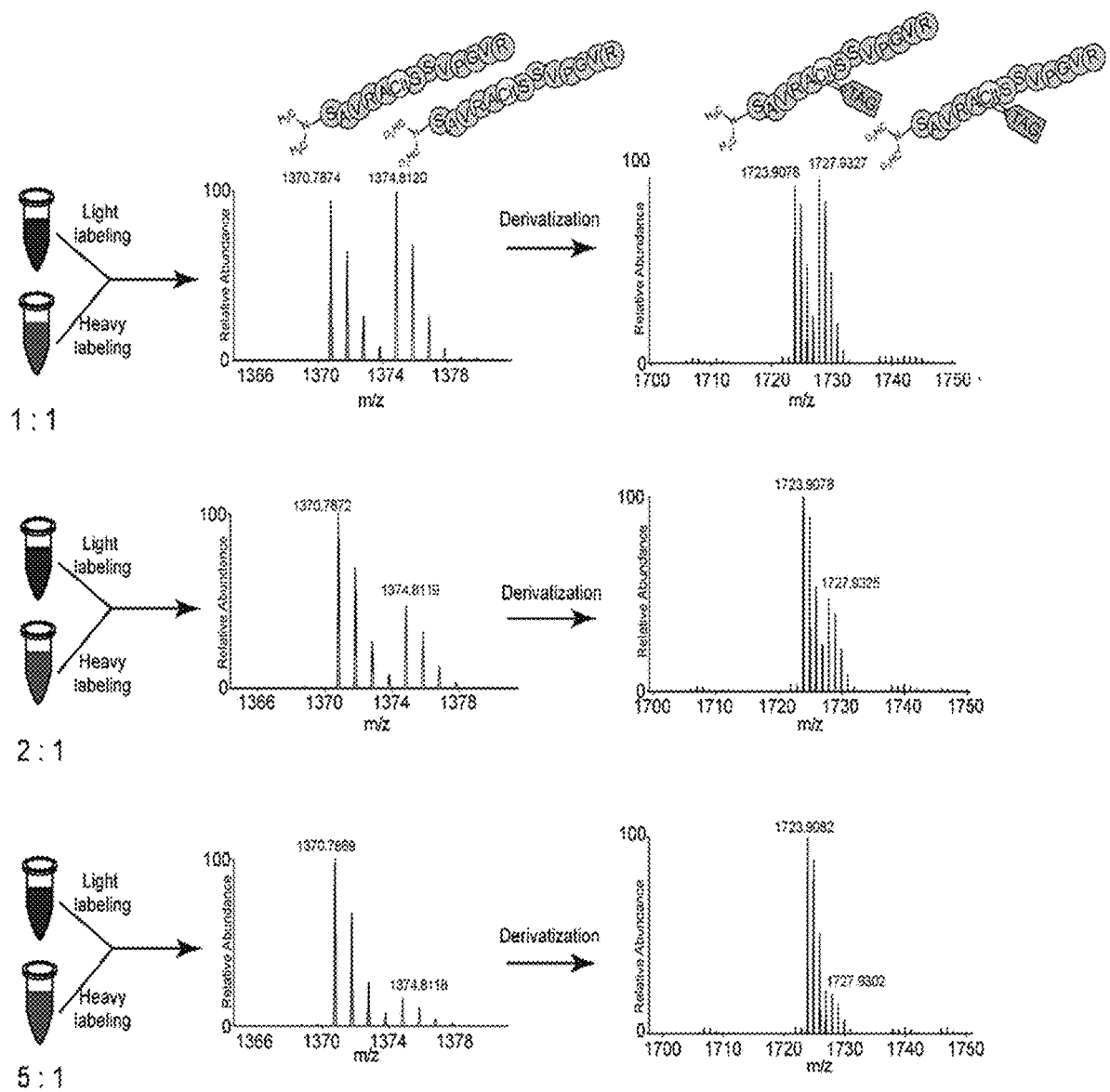
FIG. 34 shows evaluation of relative quantitation accuracy from combining a stable isotopic dimethylation labeling strategy with biotin tag-based qualitative analysis method by using the citrullinated peptide standard (SEQ ID NO:1). Three different ratios (1:1, 2:1 and 5:1) were evaluated and reliable quantitative accuracy could be obtained.

To extend the application scope, the present method was combined with stable isotopic dimethylation labeling strategy for simultaneously qualitative and quantitative analysis of citrullinated proteins from different biological samples (FIG. 29, panel a). The reaction condition of dimethyl labeling was determined by using the citrullinated peptide standard. It was found that citrullinated peptide standard could be completely dimethylated in aqueous solution without apparent side reaction observed (FIG. 30 and FIG. 31). Furthermore, the quantitative accuracy of the new method was evaluated using citrullinated peptide standard prepared at different ratios (1:1, 2:1 and 5:1), and reliable quantitative results were obtained (FIG. 32, FIG. 33 and FIG. 34). The performance of the new method was further tested using real biological samples. 600 µg of peptide digested from mouse brain extract was used for each analysis. It was no surprise that the number of identified citrullination sites and proteins reduced primarily due to the increased complexity of full MS spectrum. In addition, fewer identified citrullinated proteins could be quantified when sample difference increases, which is another drawback of isotopic labeling-based quantitative strategies (FIG. 29, panel b). Nevertheless, for these quantifiable citrullinated proteins, reliable quantitative accuracy was obtained (FIG. 29, panel c). Furthermore, integrating the biotin tag-based qualitative analysis method with isobaric labeling-based quantitative strategies may be able to reduce spectral complexity and improve throughput for large-scale quantitative analysis of citrullination.

In summary, a novel biotin cysteamine tag is described herein for the specific chemical derivatization of peptidyl-citrulline. By integrating the biotin tag-assisted enrichment approach, bottom-up proteomics, and stable isotopic dimethylation labeling strategy, a multi-faceted method has been developed, which is believed to be the first method enabling simultaneously qualitative and quantitative analysis of citrullinated proteins at large scale in different biological samples. This method provides a simple and reliable tool to unravel the roles of citrullination in biological and disease pathways, significantly expanding the understanding of this important protein PTM.

Example 2

Synthesis and storage of biotin thiol tag. A solution of biotin-NHS ester (100 mg, 0.29 mmol) and cysteamine (34 mg, 0.44 mmol, 1.5 equiv) in $CH_2Cl_2$ (5 mL) was added DIPEA (144 µL, 0.88 mmol. 3 equiv) and stirred at 40° C. for 24 h. The crude reaction product was purified using a CombiFlash system and a gradient from 0 to 20% of B, where A was dichloromethane and B was methanol. Fractions containing pure product (as detected by UV) were collected to yield the grey solid (60 mg, 0.20 mmol; 68% yield). $^1$H NMR data was obtained from a Varian Inova 500 MHz NMR spectrometer. $^{13}$C NMR data was obtained from a Bruker Avance III HD 400 MHz NMR spectrometer. The spectra were recorded in 10 mg $cm^{-3}$ $CD_3OD$ solutions with a probe temperature of ca. 300K and referenced to TMS. $^1$H NMR (500 MHz, $CD_3OD$) δ 8.17 (m, $^1$H), 4.56 (dd, J=7.7, 5.0 Hz, $^1$H), 4.37 (dd, J=7.8, 4.5 Hz, $^1$H), 3.57-3.53 (m, $^1$H), 3.42-3.40 (m, $^2$H), 3.28 (dt, J=9.9, 5.3 Hz, $^1$H), 3.00 (dd, J=12.7, 5.0 Hz, $^1$H), 2.89 (q, J=6.4 Hz, $^1$H), 2.77 (d, J=12.7 Hz, $^1$H), 2.67 (t, J=6.8 Hz, $^2$H), 2.29 (t, J=7.4 Hz, $^2$H), 1.85-1.63 (m, 4H), 1.55-1.49 (m, $^2$H). 13C NMR (101 MHz, CD$_3$OD) δ 174.8, 163.2, 62.0, 60.2, 55.6, 42.5, 39.6, 35.3, 28.4, 28.1, 25.4, 23.1. Formula: C12H22N3O2S2; [M+H]$^+$: m/z 304.1153 Da.

The dimerization of synthesized biotin thiol tag was observed upon purification and drying processes. To deal with this issue, the biotin tag powder was firstly reconstituted with methanol/water (50:50, v/v) to a concentration of 10 mg/ml. Then, neutral TCEP (Millipore Sigma, 580561) was added into the biotin tag solution to a final concentration of 10 mM for the reduction of biotin thiol tag dimer. Following that, the biotin tag solution was briefly sonicated and placed at room temperature until the solution was clear. The clear solution containing biotin thiol tag was ready for use or could be stored at −80° C. for long-term use.

Chemical derivatization of citrullinated peptide standard. A citrullinated peptide standard SAVRA{Cit}SSVPGVR was obtained from Genscript (New Jersey, USA), and dissolved in water to a concentration of 1 mg/ml. 2,3-butanedione solution was freshly prepared by transferring 1 μl of 2,3-butanedione (11038, Sigma-Aldrich) into 114 μl 12.5% TFA solution. 30 μl biotin thiol tag solution (10 mg/ml) was dried with SpeedVac, and then reconstituted with 40 μl 12.5% trifluoroacetic acid. 1 μl citrullinated peptide standard and 10 μl diluted 2,3-butanedione solution was subsequently added to initiate the chemical derivatization reaction. The mixture was incubated in the dark at 37° C. with shaking. After 6 h incubation, the reaction was stopped by drying the mixture out with SpeedVac.

To remove excess reactants, strong cation exchange (SCX) chromatography was performed using TopTips (TT200SEA, Poly LC) containing PolySULFOETHYL A beads. Briefly, SCX beads were pre-equilibrated with 100 μl loading buffer containing 50% ACN/0.2% FA/10 mM ammonium formate for three times. The derivatized citrullinated peptide standard was then reconstituted in 200 μl loading buffer and applied to the SCX beads twice followed by continuous washing of the beads with 100 μl loading buffer for 10 times. Peptide was finally eluted by rinsing the beads with 50 μl 25% ACN/0.4M ammonium formate for 3 times. All centrifugation steps were performed at 2,000 rpm for 2 min.

Protein extraction and digestion. Mouse tissues were collected and stored at −80° C. freezer until use. Tissues were homogenized with a probe ultrasonicator in 4% Sodium dodecyl sulfate (SDS)/50 mM Tris base buffer (~pH 8, adjusted with HCl). After homogenization, supernatant of tissue extract was collected after centrifugation at 16,000 rcf for 15 min. Protein concentration was determined by BCA protein assay reagent (Thermo Scientific, Fair Lawn, NJ).

800 μg of protein extract was reduced by 10 mM dithiothreitol (DTT) for 30 min at room temperature and then alkylated with 50 mM iodoacetic acid (IAA) for another 30 min in the dark. Protein was further precipitated by adding cold acetone (−20° C.) to a final concentration of 80% (v/v). After incubation in −20° C. overnight, the sample solution was centrifuged at 16,000 rcf for 15 min and the supernatant was discarded. To completely remove SDS, the pellet was washed with cold 80% acetone for another two times, and then dried in the air for 12 min. The dried pellet was reconstituted with 150 μl 5M Guanidine hydrochloride/50 mM Tris-base buffer (pH 8, adjusted with HCl). After reconstitution, the buffer solution was diluted tenfold with 50 mM Tris-base buffer to reduce Guanidine HCl to 0.5M. Mass spec grade Trypsin/Lys-C Mix (Promega, Madison, WI; Protein enzyme, 100:1, w/w) was added to samples and incubated at 37° C. for 6 h. The secondary digestion was performed by adding the same amount of Trypsin/Lys-C Mix and incubating samples at 37° C. for another 12 h. The digestion process was quenched by adding 10% TFA to reduce the pH to <3. Digested peptides were desalted with C18 columns (Sep-Pak, waters, Milford, MA) and eluted with 80% ACN/0.2% FA, which were dried out with SpeedVac.

Tryptic peptides were reconstituted with 800 μl of water. Peptide concentration was determined by colorimetric peptide assay (23275, Thermo Scientific, Fair Lawn, NJ). 400 μg of peptides were transferred to a new Eppendorf tube and dried for further analysis.

Chemical derivatization of citrullinated peptides. 30 μl of biotin thiol tag (10 mg/ml) solution was added to each sample tube containing 400 μg peptides and dried with SpeedVac. Then, the biotin thiol tag and peptides were reconstituted in 40 μl 12.5% TFA solution followed by adding 10 μl of 2,3-butanedione solution prepared as mentioned above. The reactants were well mixed and incubated at 37° C. for 6 h with shaking in the dark. Samples were further dried out by vacuum. To remove leftover reactants, SCX chromatography was performed as mentioned above. Peptides were finally eluted in 150 μl buffer of 25% ACN/0.4M ammonium formate and dried out with vacuum. A secondary drying process was conducted to reduce the concentration of ammonium formate in samples before enrichment by adding another 400 μl water to each sample and drying out in vacuum.

Enrichment of biotinylated citrullinated peptides with Streptavidin beads. To enable complete dissolution of peptides recovered from SCX, 300 μl 50% ACN/H$_2$O was added to each sample. After brief vortex and centrifugation, each sample was dried in a SpeedVac to less than 100 μl and further diluted with 900 μl PBS 1× buffer. The enrichment process was performed as previously described with some modifications. Briefly, 75 μl streptavidin beads were pre-washed with 1 ml PBS 1× buffer for 5 times. Then peptides in 1 ml PBS buffer were loaded onto streptavidin beads and incubated at room temperature for 2 h with rotation. The beads were subsequently washed 4 times each with 1 ml PBS 1× buffer, 1 ml 5% ACN/PBS 1× buffer and 1 ml water. The bound peptides were finally released with 300 μl 80% ACN/H$_2$O contain 0.2% TFA and 0.1% FA for four times. The first release was performed in room temperature for 5 mins, while other three release processes were conducted at 95° C. for 5 mins with shaking. The eluents were combined and dried in the SpeedVac. Enriched peptides were desalted with C18 columns (Zip-tips,) and eluted in 100 μl 80% ACN/0.2% FA solution, which was dried in vacuum to almost dry.

Mass spectrometry (MS) analysis of citrullinated and homo-citrullinated peptides. MS analysis was performed on an Orbitrap Fusion Lumos Tribrid mass spectrometer coupled with Dionex UltiMate 3000 UPLC system (Thermo Fisher Scientific, San Jose, CA). The mobile phase was composed of 0.1% formic acid in water (A) and 0.1% formic acid in acetonitrile (B). The flow rate was set as 300 nl/min. Each sample was resuspended in 15 μl 0.1% formic acid 3% acetonitrile in water and subjected to three LC-MS/MS runs. For each run, 2 μl of sample was loaded on a customized C18 column filled with 1.7 μm Ethylene Bridged Hybrid (EBH) packing materials (130 Å, Waters) and separated with the following gradient: 3% B for the first 18.3 min upon sample trapping; 3%-30% B for 18.3-120 min; 30%-75% B for 120-120.5 min; 75% B for 120.5-130 min; 75%-95% B for 130.0-130.5 min; 95% B for 130.5-140.0 min; 95%-3% B for 140.0-140.5 min and equilibrated at 3% B for 15 min. MS data was acquired in the positive ion mode with the spray voltage of 2 kV. MS1 spectra were collected from m/z 350-1500 by orbitrap at a resolution of 60 K. Automatic gain control (AGC) target and maximum injection time was set to $2e^5$ and 100 ms, respectively. Ions with the charge of 2-6 were included for screening, while a dynamic exclusion time of 45 s was used to avoid repeatedly sequencing the same precursor ion in a short time.

Database search. MS data from mouse tissues was searched against mouse protein database (Downloaded from Uniprot website on Dec. 30, 2018) using the software of MaxQuant. The search parameters were defined as following: 20 ppm and 4.5 ppm were set as the first search peptide tolerance and the main search peptide tolerance, respectively; 2 ppm was used for the isotope match tolerance. A minimum of six amino-acid peptide length and up to three missed cleavages were allowed for peptide identification; carbamidomethylation (C) was set as a static modification, while oxidation (M, +15.995 Da), citrullination+biotin tag label (R, +354.1071 Da) were defined as dynamic modifications. A neutral loss of biotin tag (303.1075) and two diagnostic peaks of 227.0848 Da and 304.1147 Da were included in the search. The maximum of three modifications were allowed for each peptide. The 1% false-discovery rate (FDR) was applied to filter both peptide and protein identification.

Example 3

Figure 35:
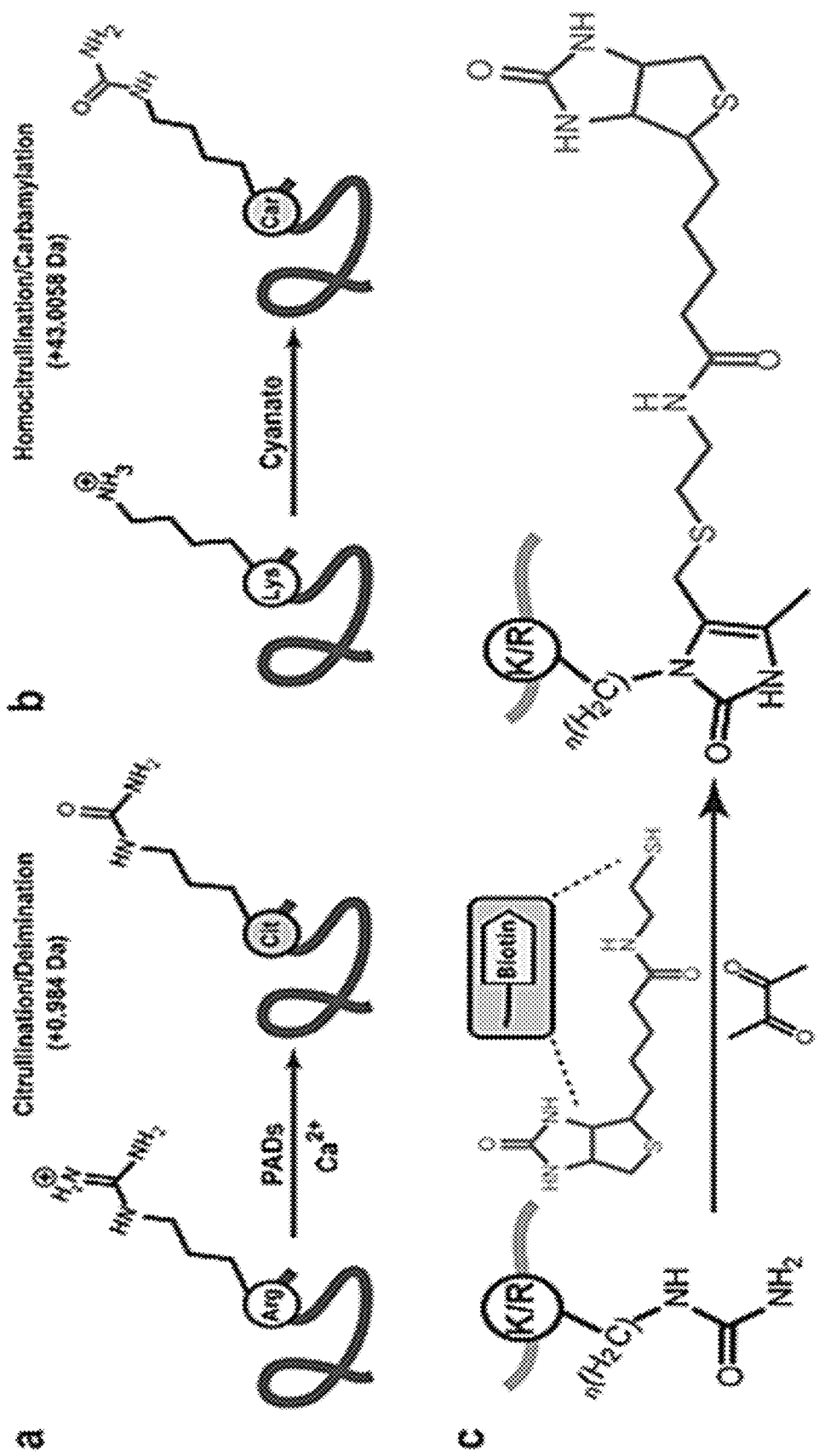
FIG. 35 illustrates hydrolytic conversion of peptidyl arginine residues into citrulline (a), and chemical modification of lysine residues into homocitrulline (b). The citrullinated or homocitrullinated peptides are able to be derivatized using the biotin thiol tag (c).

Introduction. PAD enzymes are able to catalyze the hydrolytic conversion of peptidyl arginine residues into citrulline (FIG. 35, panel a). Similarly, chemical modification of lysine residues can result in homocitrullination of polypeptides (FIG. 35, panel b).

Protein homocitrullination, also called protein carbamylation, is a type of non-enzymatic protein post-translation modification. In vivo, this modification results from the chemical modification of the free amine group of the lysine residue by cyanate, which produced either from urea or the conversion from thiocyanate (see Scheme 1 below). It has been reported that protein homocitrullination is involved in many autoimmune diseases, especially in rheumatoid arthritis (RA).

Chemical modification of citrullinated and homocitrullinated proteins with the novel thiol-containing biotin tag. Until the present study, there was no effective method for the large-scale identification of proteins with the homocitrullination modification from complex biological samples primarily due to the lack of enrichment tools.

Figure 36:
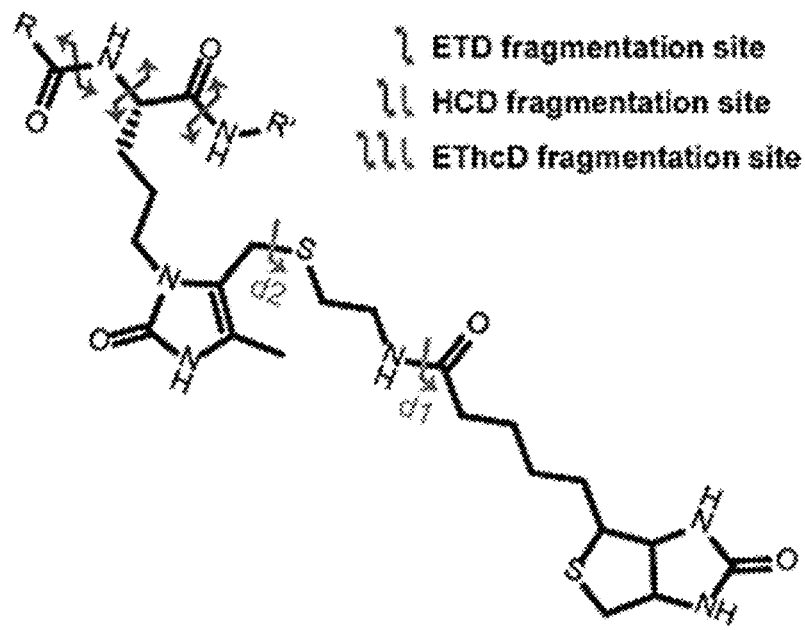
FIG. 36 shows fragmentation sites of biotin thiol tag-derivatized citrullinated peptides upon HCD, ETD, or EThcD fragmentations (a); and a tandem MS spectrum of the biotin thiol tag-derivatized citrullinated peptide standard (SEQ ID NO:1) upon HCD fragmentation (b).
Figure 36:
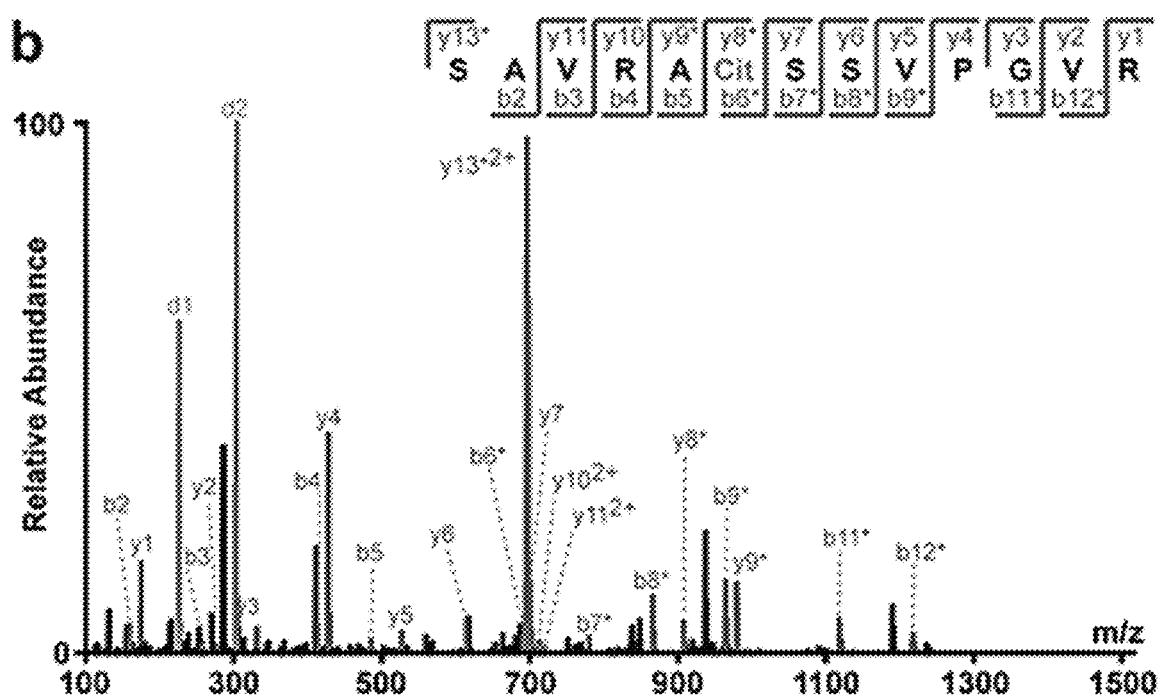

However, it was noticed that the homocitrullinated peptide could generate a ureido group at the side chain of lysine. Therefore, the side chains of both citrullinated and homocitrullinated peptides are characterized by the presence of an ureido group. The novel thiol-containing biotin tag reported in this invention, particularly with 2, 3-butanedione, can specifically modify an ureido group in low pH aqueous solution (see Scheme 2). Therefore, a thiol-containing biotin tag could be used to simultaneously modify and enrich citrullinated and homocitrullinated peptides from biological samples for mass spectrometry analysis (see FIG. 35, panel c). The enriched biotin tag-modified citrullinated and homocitrullinated peptides could be differentiated based on their different mass shift, as well as the specific fragmentation location sites (see FIG. 36).

Scheme 2 - Chemical modification of homocitrullinated peptide with 2, 3-butanedione and biotin cysteamine tag.

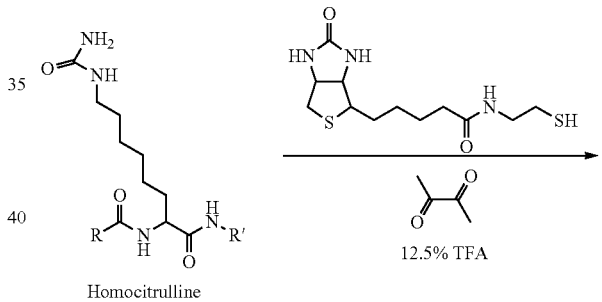

Scheme 1 - The chemical process of protein homocitrullination in vivo.

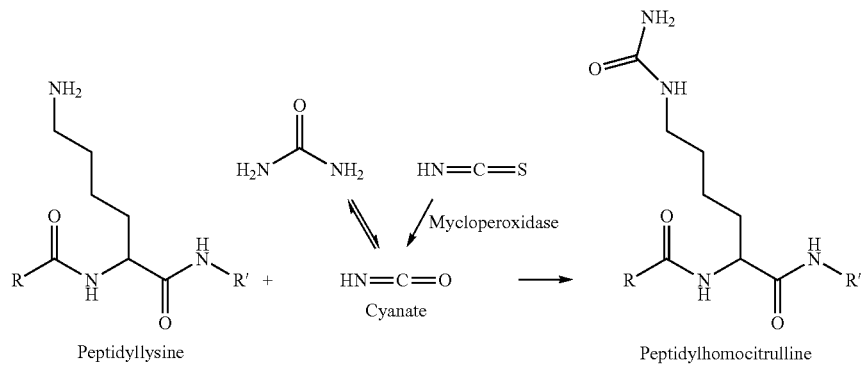

-continued

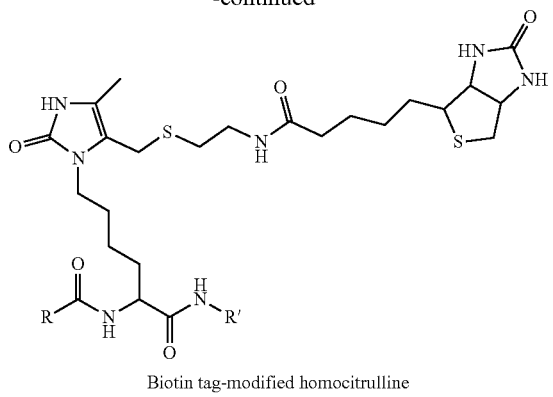

Biotin tag-modified homocitrulline

Figure 37:
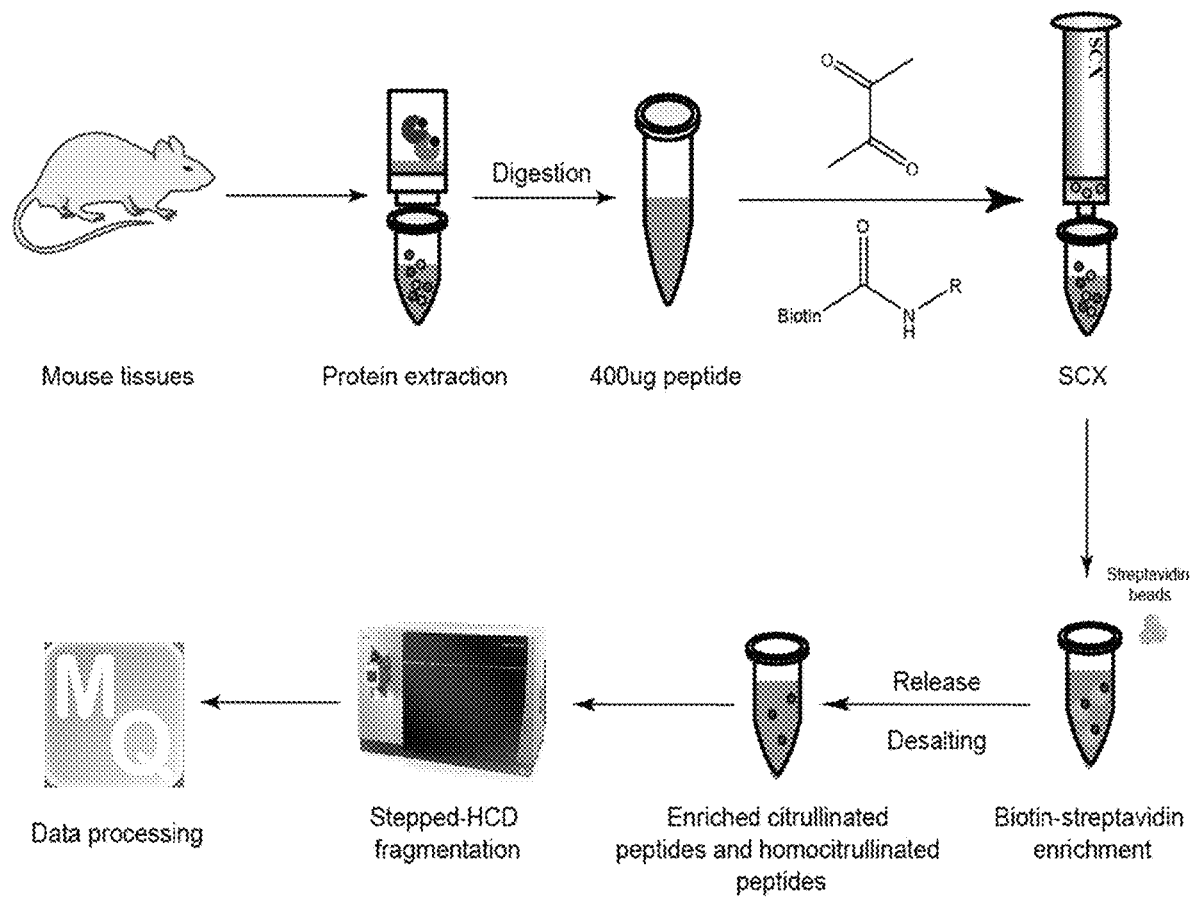
FIG. 37 shows a workflow for simultaneously qualitative analysis of citrullinated proteins and homocitrullinated proteins from biological samples.

Workflow for simultaneously qualitative analysis of citrullinated proteins and homocitrullinated proteins from biological samples. One example of a potential workflow is described in (FIG. 37). Briefly, mouse tissues were homogenized with a probe sonicator in 4% SDS/Tris base buffer and protein concentration was determined by BCA assay. Proteins were reduced by dithiothreitol at room temperature for 30 min followed by alkylation with excess iodoacetamide. After that, SDS was removed by iced acetone protein precipitation. Protein pellet was firstly reconstituted in 5M guanidine hydrochloride solution and then diluted 10 folds for trypsin digestion. After digestion and desalting, peptides were derivatized with the thiol-containing biotin tag and the unreacted derivatization reagents were removed by strong cation exchange (SCX) chromatography. The chemical derivatized citrullinated and homocitrullinated peptides were enriched with streptavidin beads and finally eluted for LC-MS/MS analysis. Note: urea must be excluded during sample preparation process.

Figure 38:
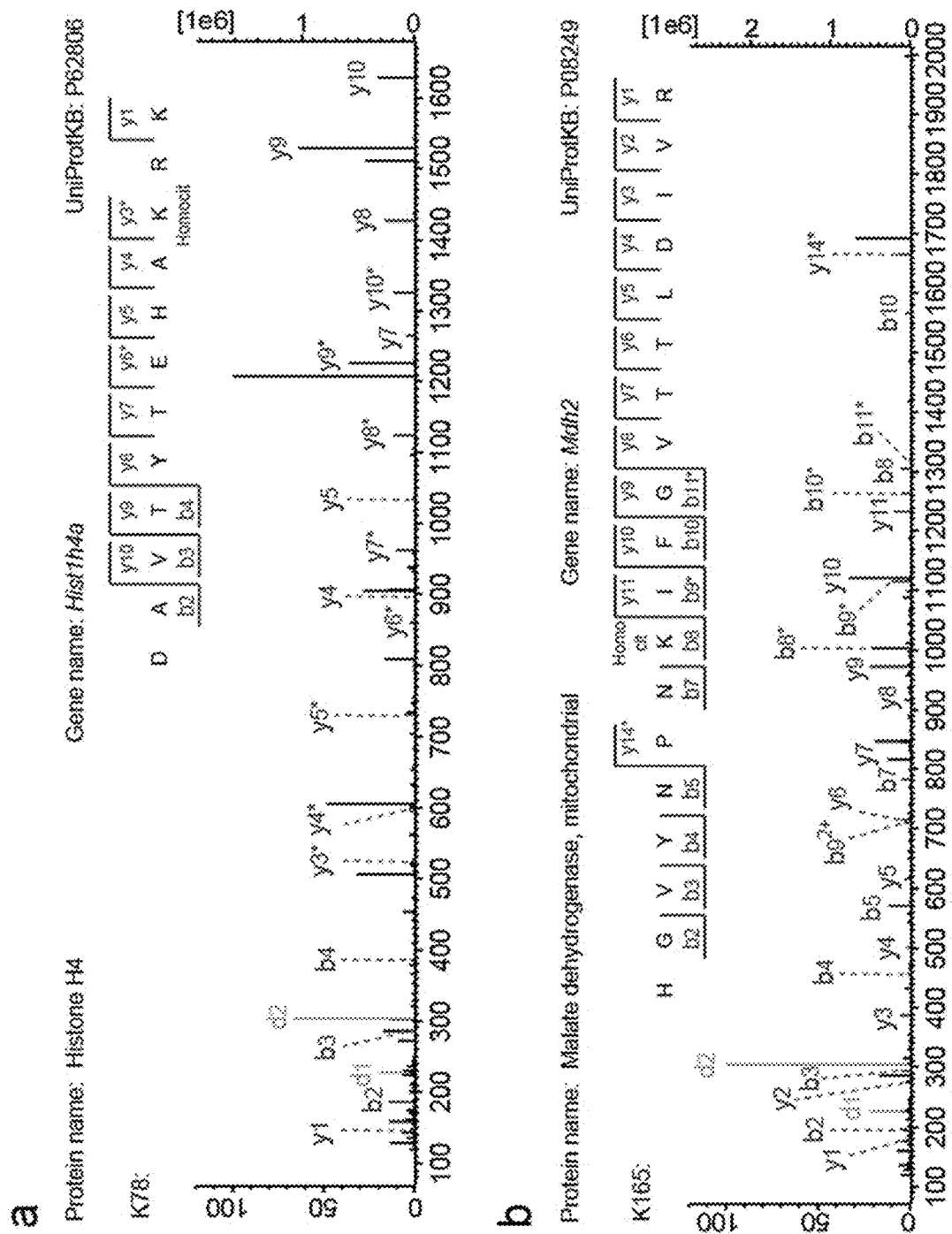
FIG. 38 shows examples of homocitrullinated peptides (SEQ ID NO:17 (top) and SEQ ID NO: 18 (bottom)) identified from mouse brain.

MS-based detection of homocitrullinated proteins from biological samples. MS data from mouse tissues was searched against mouse protein database (Downloaded from Uniprot website on Dec. 30, 2018) using the software of MaxQuant. The same parameters previously mentioned for citrullinaton analysis are used for homocitrullination analysis except that homocitrullination+biotin tag label (K, +396.1290 Da) instead of citrullination+biotin tag label (R, +354.1071 Da) is defined as one of the dynamic modifications. Mouse-tissue specific protein homocitrullination analysis was performed. Many homocitrullinated proteins were successfully identified from mouse tissues. Two examples of homocitrullinated proteins identified from mouse tissues are shown in (FIG. 38).

Figure 39:
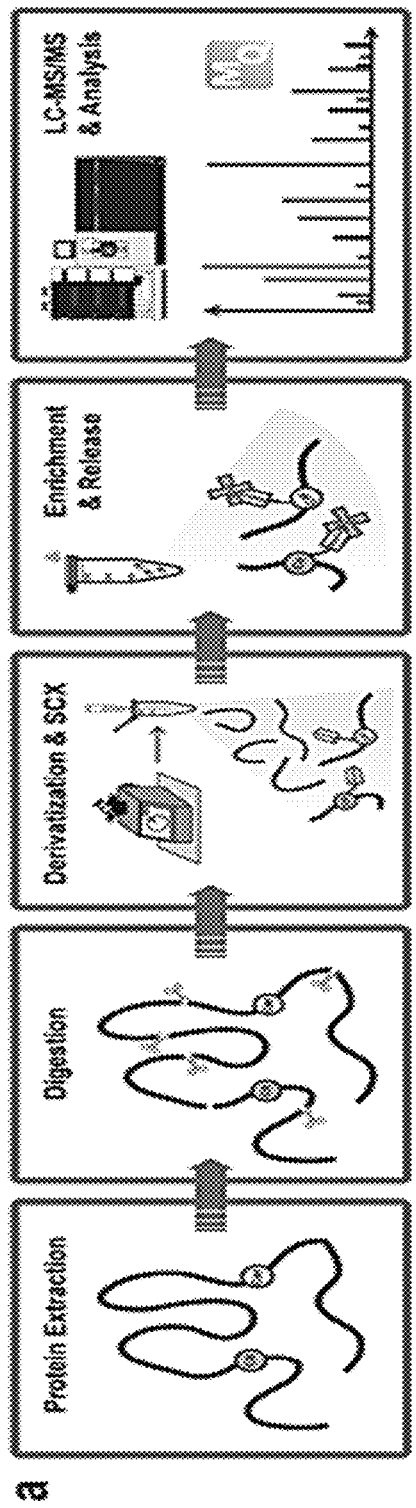
FIG. 39 shows an experimental workflow of protein citrullination analysis with a biotin thiol tag (a); an exemplary tandem MS spectrum of an identified citrullinated peptide (SEQ ID NO:19) from PAD treated histone H3 protein with the citrullination site (R18Cit) in the middle of the peptide (b); and an exemplary tandem MS spectrum of the same citrullination site (R18Cit) identified at the C-terminal of another citrullinated peptide (SEQ ID NO:20) from PAD treated histone H3 protein (c).
Figure 39:
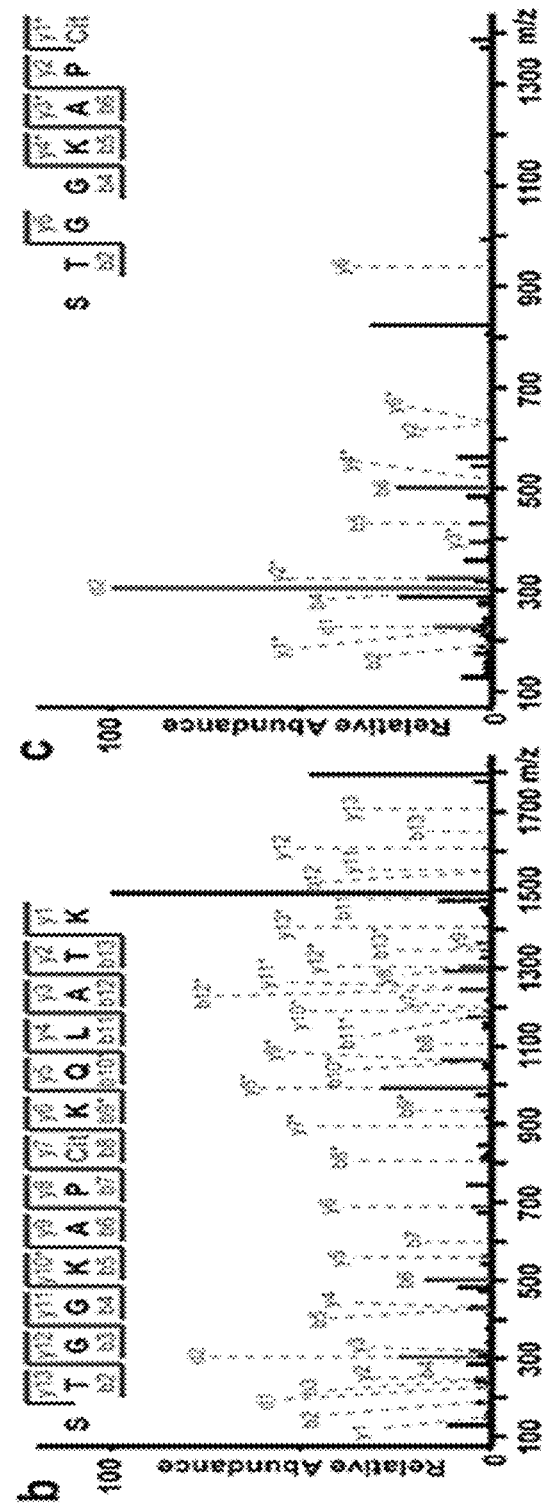
Figure 40:
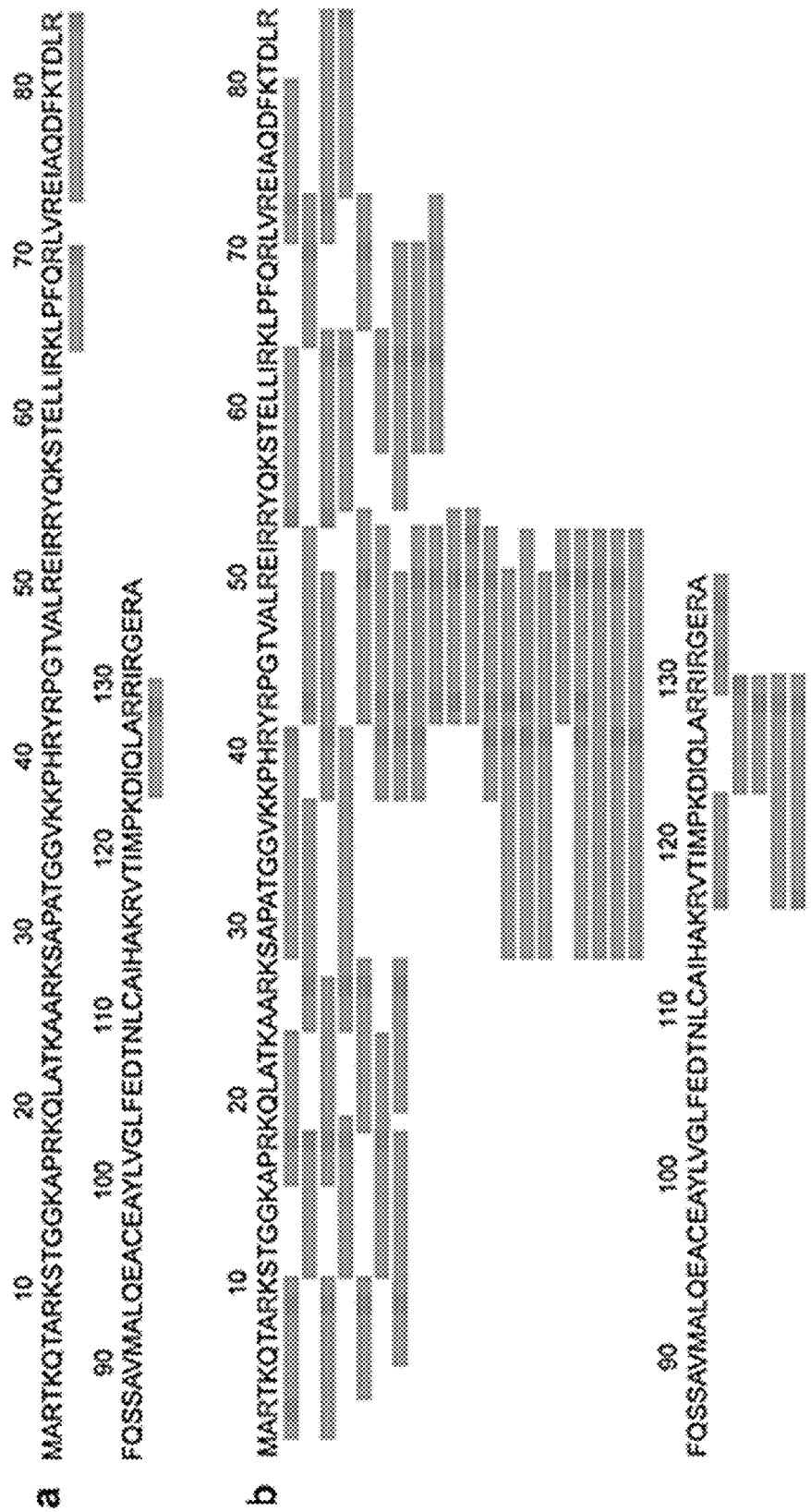
FIG. 40 shows a citrullination analysis on a histone H3 protein (SEQ ID NO:21) before (a) and after (b) in vitro PAD treatment. Rectangles below the sequences indicate confidently identified citrullinated peptides.

Improved in vitro protein citrullination analysis with biotin thiol tag. An additional experimental workflow of protein citrullination analysis with a biotin thiol tag is illustrated in FIG. 39, panel a. After protein extraction and digestion, the digested protein is derivatized with the biotin thiol tag, and is further enriched before MS analysis. For example, FIG. 40 shows citrullination analysis on histone H3 protein before (panel a) and after (panel b) in vitro PAD treatment. Rectangles below the sequence indicate confidently identified citrullinated peptides with identified citrullination sites. FIG. 39, panel b, shows an example tandem MS spectrum of an identified citrullinated peptide from PAD treated histone H3 with the citrullination site (R18Cit) in the middle of the peptide, and FIG. 39, panel c, shows an example tandem MS spectrum of the same citrullination site (R18Cit) identified at the C-terminal of another citrullinated peptide from PAD treated histone H3.

Figure 41:
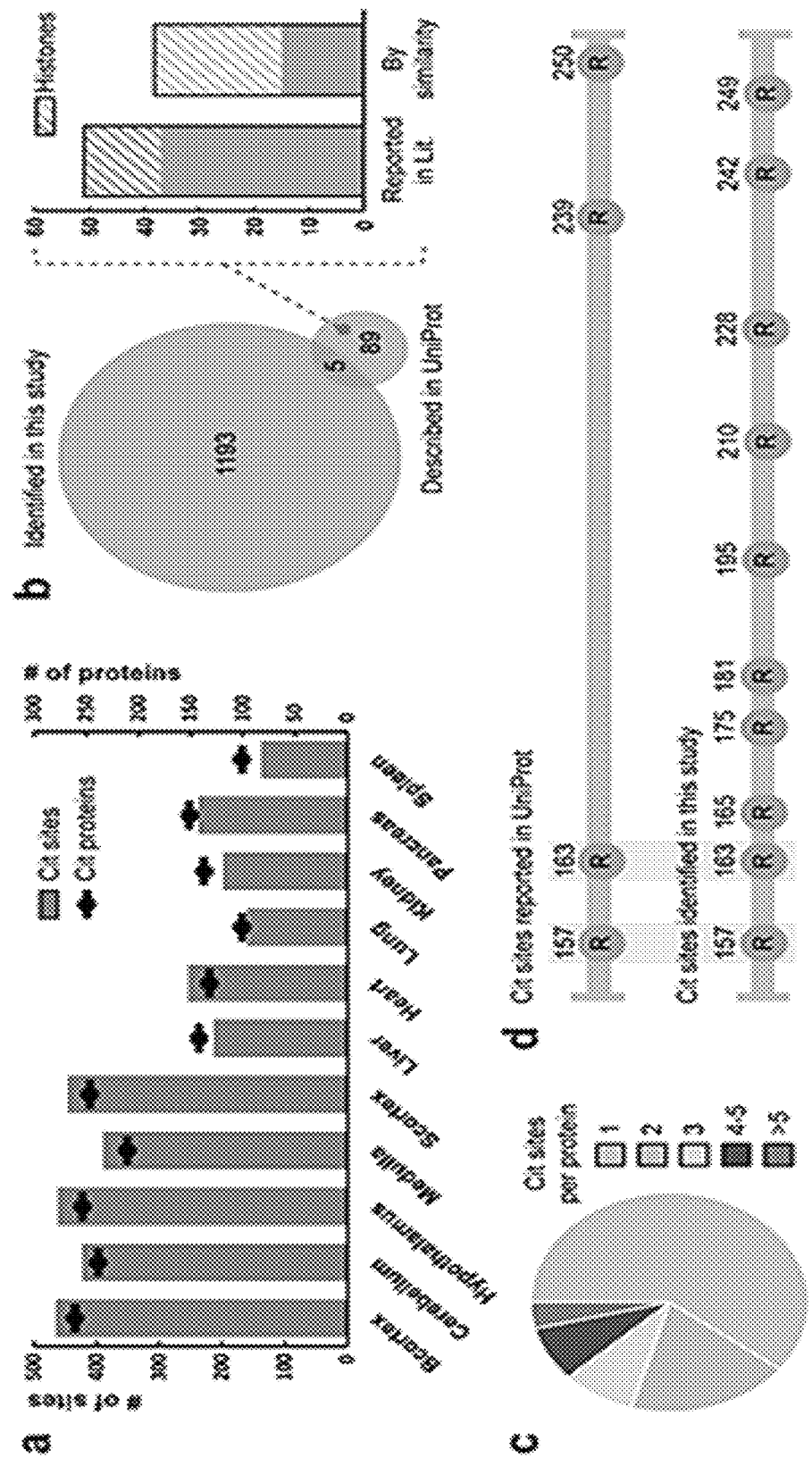
FIG. 41 shows a number of identified citrullinated proteins and citrullination sites in different mouse tissues (a); an overlap of citrullination sites identified in the study with those reported in the UniProt database (b); a distribution of the number of citrullination sites per identified citrullinated proteins (c); and a comparison of citrullination sites identified in the study and those reported in UniProt database on a myelin basic protein (d).

Large-scale citrullinome profiling of different mouse tissues. Using the biotin thiol tag, citrullinated proteins and citrullination sites were able to be identified in multiple different mouse tissues (FIG. 41, panel a). The overlap of citrullination sites identified in this study with those reported in the UniProt database are shown in FIG. 41, panel b. In addition to the low overlap, many of the sites only reported in UniProt are based on similarity prediction or location on histone proteins. FIG. 41, panels c and d, show the distribution of citrullination sites per identified citrullinated protein, and a comparison of citrullination sites identified in this study and those reported in UniProt database on the myelin basic protein.

Figure 42:
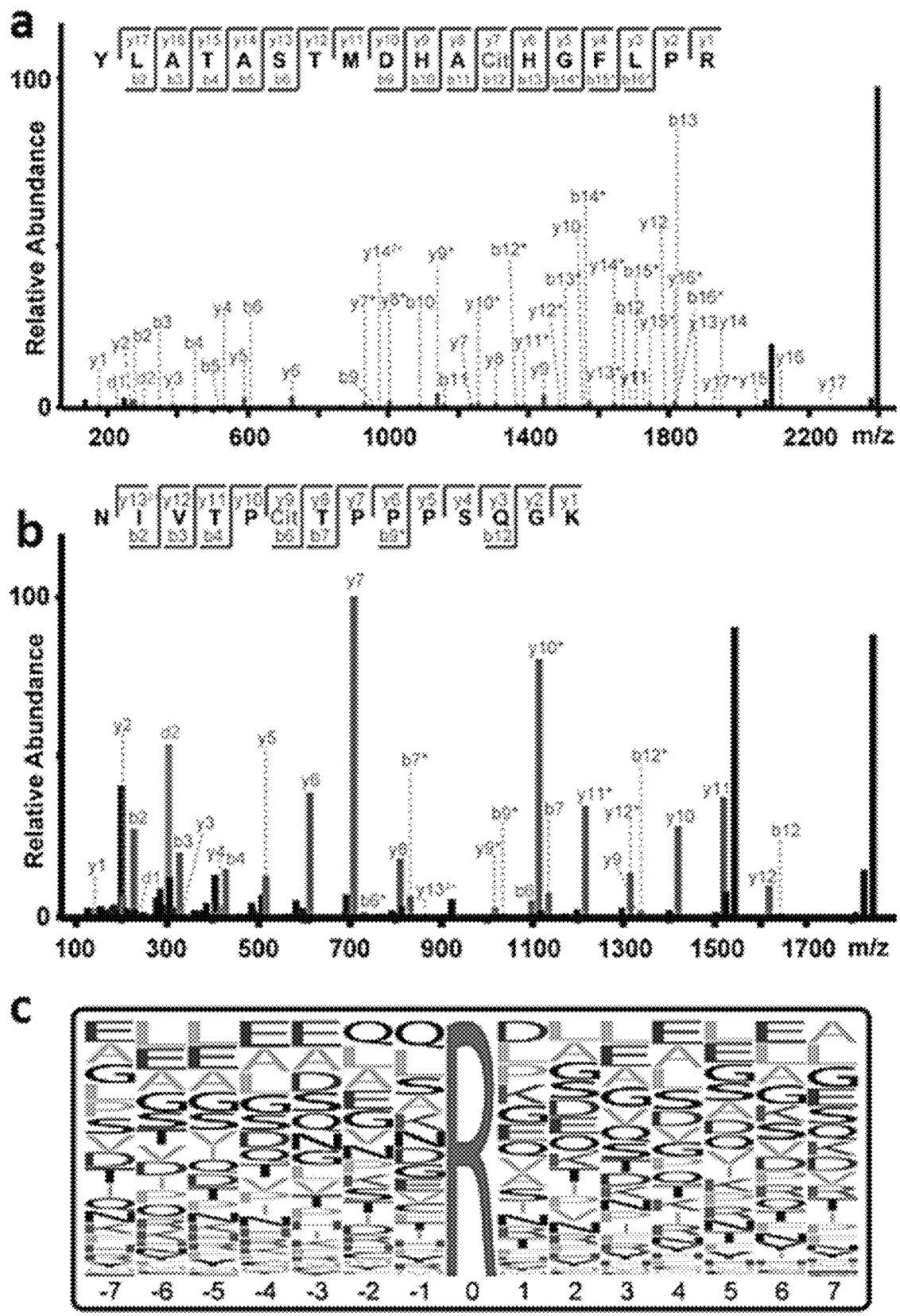
FIG. 42 shows exemplary tandem MS spectra of two citrullination sites identified on the myelin basic protein, R157Cit (a) and R228Cit (b); and a sequence motif of identified citrullinated peptides. Citrullination sites are centered in the middle as "0" position. The height of letters indicates the relative frequency of each amino acid at certain positions.

Exemplary tandem MS spectra of two citrullination sites identified on the myelin basic protein, R157Cit and R228Cit, are shown in FIG. 42, panels a and b, respectively). Additionally, a sequence motif of identified citrullinated peptides is shown in FIG. 42, panel c, where citrullination sites are centered in the middle as the "0" position. The height of letters indicates the relative frequency of each amino acid at certain positions.

Figure 43:
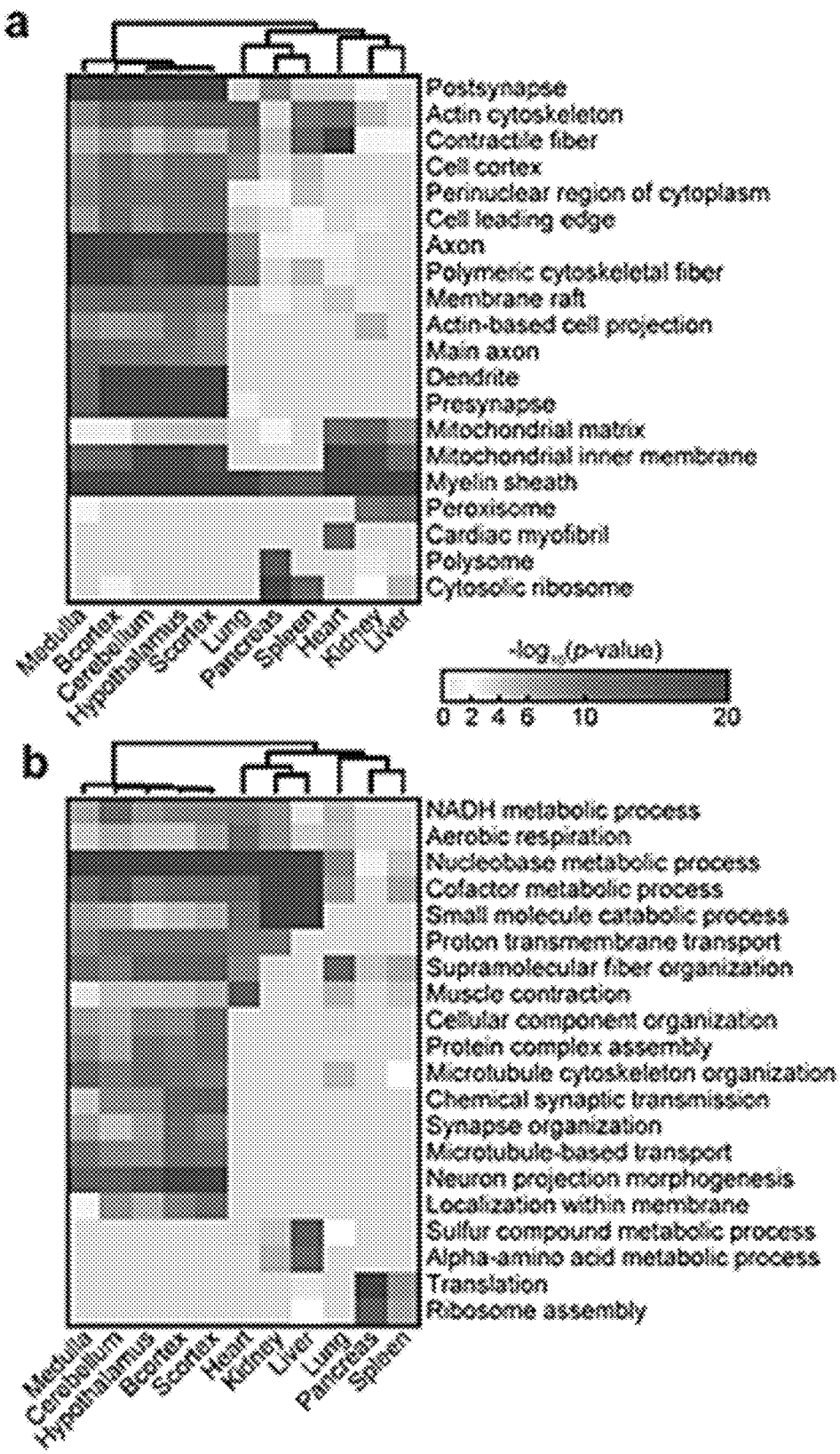
FIG. 43 shows the significantly enriched (p-value <0.01 in at least one tissue region) cellular components (a) and biological processes (b) in different mouse tissues. The most significant twenty terms are shown in each heatmap. The different shading indicates $-\log_{10}$ p-values. Columns are clustered based on their profile similarity.

Heatmaps showing the significantly enriched (p-value <0.01 in at least one tissue region) cellular components and biological processes in different mouse tissues are shown in FIG. 43, panels a and b, respectively. The most significant twenty terms are shown in each heatmap, and columns are clustered based on their profile similarity. The different shading indicates $-\log_{10}$ p-values.

Figure 44:
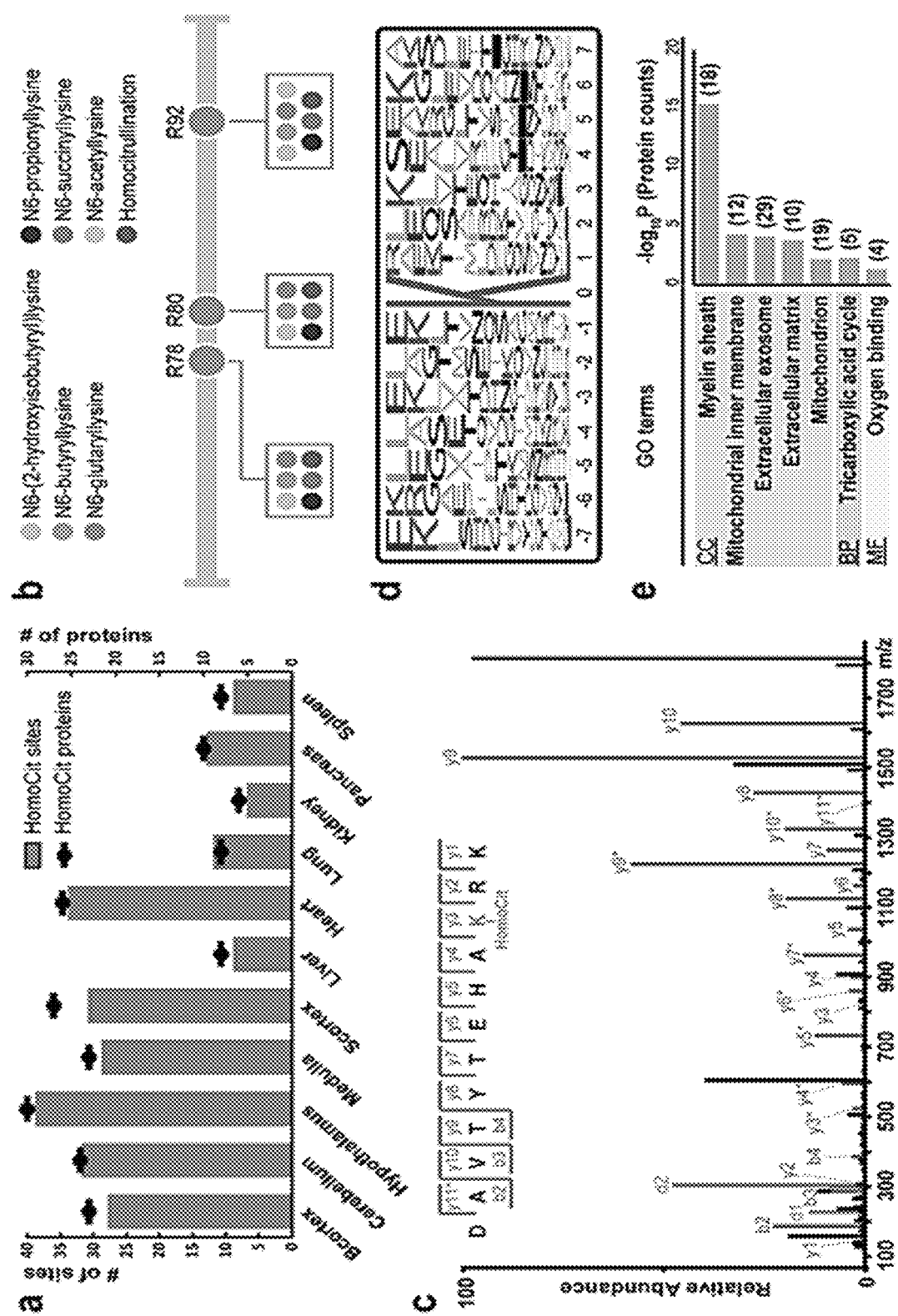
FIG. 44 shows a number of identified homocitrullinated proteins and homocitrullination sites in different mouse tissues (a); co-localization of homocitrullination sites identified in the study with other lysine modifications reported in the UniProt database on histone H4 (b); an exemplary tandem MS spectrum of a homocitrullination site identified on histone H4 (K78HomoCit) (c); a sequence motif of identified homocitrullinated peptides. Homocitrullination sites are centered in the middle as "0" position; and a gene ontology analysis of all identified homocitrullinated proteins showing the significantly enriched terms (p-value <0.05) (e). As used in the figure, CC=cellular component; BP=biological process; and MF=molecular function.

Profiling of protein homocitrullination in different mouse tissues. Using the biotin thiol tag, homocitrullinated proteins and homocitrullination sites were also able to be identified in multiple different mouse tissues (FIG. 44, panel a). Co-localization of homocitrullination sites identified in this study with other lysine modifications reported in UniProt database on histone H4 are shown in FIG. 44, panel b, and an exemplary tandem MS spectra of a homocitrullination site identified on histone H4 (K78HomoCit) is shown in FIG. 44, panel c. A sequence motif of identified citrullinated peptides is shown in FIG. 44, panel d, where citrullination sites are centered in the middle as the "0" position. The height of letters indicates the relative frequency of each amino acid at certain positions. A gene ontology analysis of all identified homocitrullinated proteins is shown in FIG. 44, panel e.

Figure 45:
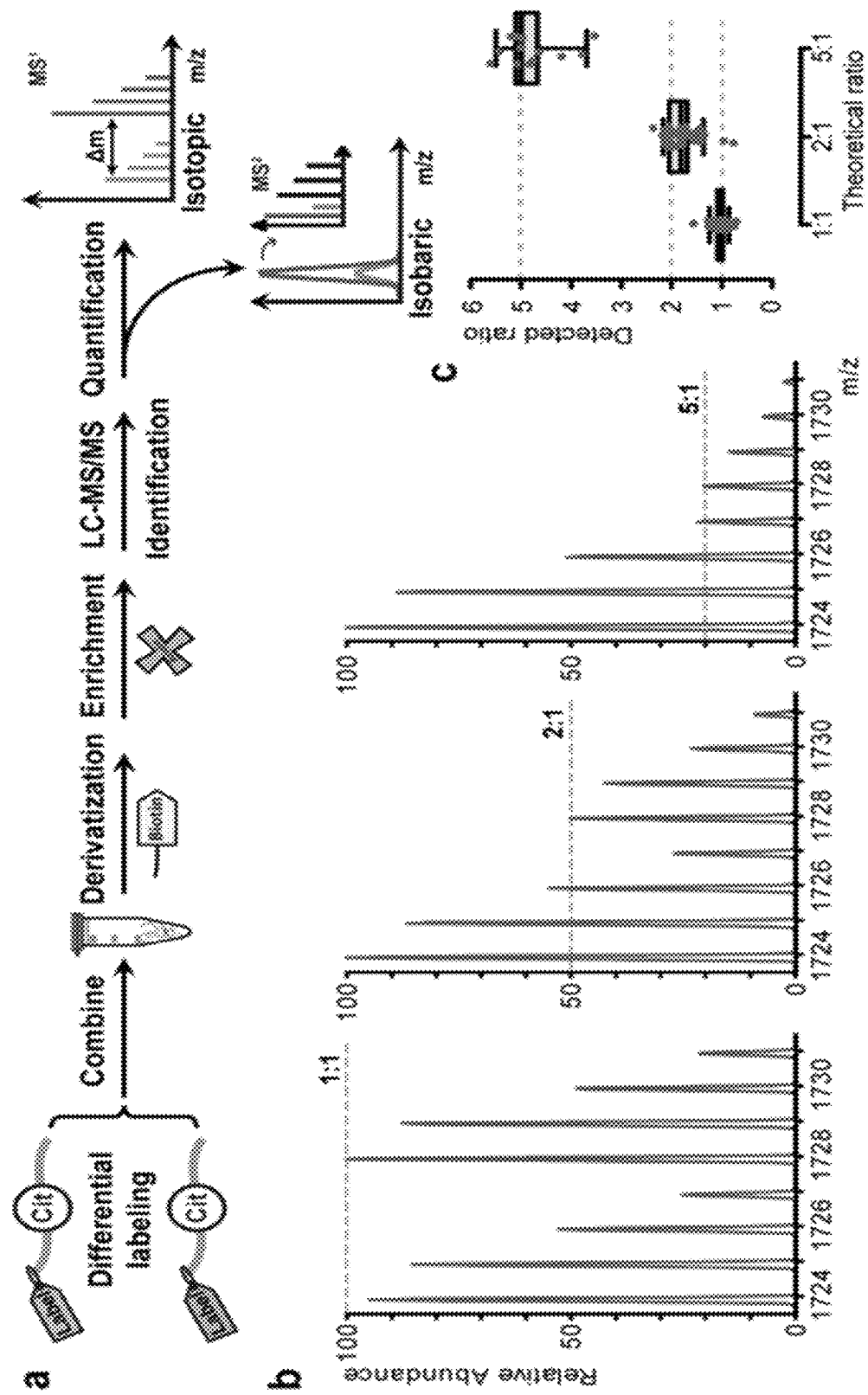
FIG. 45 shows a schematic for simultaneous qualitative and quantitative analysis of citrullination and homocitrullination using isotopic or isobaric labeling (a). Relative quantification can be achieved at MS1 or MS2 level, respectively. (b) Shows spectra showing quantitation accuracy in duplex dimethylation labeling using a citrullinated peptide standard. The peptide standard was dimethylated by either heavy isotope or light isotope labeling, resulting a 4 Da mass difference. Heavy and light labels were mixed in three known ratios (1:1, 2:1 and 5:1) and subjected to derivatization using biotin thiol tag. (c) Boxplots showing quantitation accuracy and precision in duplex dimethylation labeling using mouse brain digest.

Multiplexed quantitative citrullination analysis using chemical labeling strategies. FIG. 45, panel a, shows a schematic for simultaneous qualitative and quantitative analysis of citrullination and homocitrullination using isotopic or isobaric labeling tags described herein. Relative quantification can be achieved using MS1 or MS2.

Quantitation accuracy in duplex dimethylation labeling using a citrullinated peptide standard is shown in FIG. 45, panel b. A peptide standard was dimethylated by either heavy isotope or light isotope labeling, resulting a 4 Da mass difference. Heavy and light labels were mixed in three known ratios (1:1, 2:1 and 5:1) and subjected to derivatization using biotin thiol tag. FIG. 45, panel c, provides boxplots showing quantitation accuracy and precision in duplex dimethylation labeling using a mouse brain digest. The dots indicate the detected ratios for each quantified citrullinated peptide, with the top and bottom of boxes indicating the 3rd and 1st quartile, respectively, and the whiskers extending to 95th and 5th quartile. Horizontal lines within boxes denote the median.

Having now fully described the present invention in some detail by way of illustration and examples for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

When a group of materials, compositions, components or compounds is disclosed herein, it is understood that all individual members of those groups and all subgroups thereof are disclosed separately. Every formulation or combination of components described or exemplified herein can be used to practice the invention, unless otherwise stated. Whenever a range is given in the specification, for example, a temperature range, a time range, or a composition range, all intermediate ranges and subranges, as well as all individual values included in the ranges given are intended to be included in the disclosure. Additionally, the end points in a given range are to be included within the range. In the disclosure and the claims, "and/or" means additionally or alternatively. Moreover, any use of a term in the singular also encompasses plural forms.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements.

One of ordinary skill in the art will appreciate that starting materials, device elements, analytical methods, mixtures and combinations of components other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. The invention illustratively described herein suitably may be practiced in the absence of any element or elements, limitation or limitations which is not specifically disclosed herein. Headings are used herein for convenience only.

All publications referred to herein are incorporated herein to the extent not inconsistent herewith. Some references provided herein are incorporated by reference to provide details of additional uses of the invention. All patents and publications mentioned in the specification are indicative of the levels of skill of those skilled in the art to which the invention pertains. References cited herein are incorporated by reference herein in their entirety to indicate the state of the art as of their filing date and it is intended that this information can be employed herein, if needed, to exclude specific embodiments that are in the prior art.

The invention claimed is:

1. A method of analyzing a target biomolecule in a sample, said method comprising the steps of:
   a) providing a sample containing the target biomolecule, wherein the target biomolecule comprises a polypeptide having a region modified by a post-translational modification (PTM);
   b) reacting the target biomolecule with a tagging reagent to generate a labeled biomolecule, wherein the reacting step comprises adding the tagging reagent with 2,3-butanedione, 2,3-butanedione monoxime, or a phenylglyoxal derivative to the target biomolecule thereby generating a derivatized polypeptide from the polypeptide having the region modified by the PTM, wherein the tagging reagent comprises a thiol group or a disulfide group able to react with the derivatized polypeptide, and wherein reacting the tagging reagent with the target biomolecule imparts a mass shift to the target biomolecule;
   c) ionizing the labeled biomolecule to form a precursor ion;
   d) detecting and analyzing the precursor ion using a mass spectrometer; and
   e) identifying biomolecules with mass spectrometry data;

wherein the phenylglyoxal derivative has the formula:

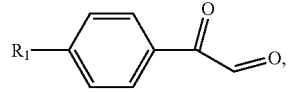

where $R_1$ comprises a thiol group or is functional group able to react with a biotin-thiol tag.

2. The method of claim 1 wherein the tagging reagent comprises a tag having the formula:

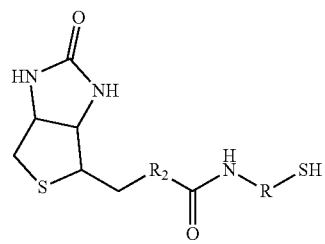

wherein R is selected from the group consisting of substituted and unsubstituted $C_1$ to $C_{24}$ alkyl groups, $C_4$ to $C_{24}$ cycloalkyl groups, $C_2$ to $C_{24}$ alkenyl groups, $C_5$ to $C_{24}$ cycloalkenyl groups, $C_6$ to $C_{24}$ aryl groups and $C_7$ to $C_{24}$ arylalkyl groups; and $R_2$ is selected from the group consisting of substituted and unsubstituted $C_1$ to $C_{10}$ alkyl groups and $C_2$ to $C_{10}$ alkenyl groups.

3. The method of claim 2 wherein R is:

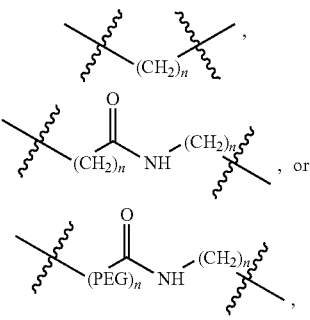

where PEG is polyethylene glycol and where n is an integer from 1 to 6.

4. The method of claim 2 wherein R is:

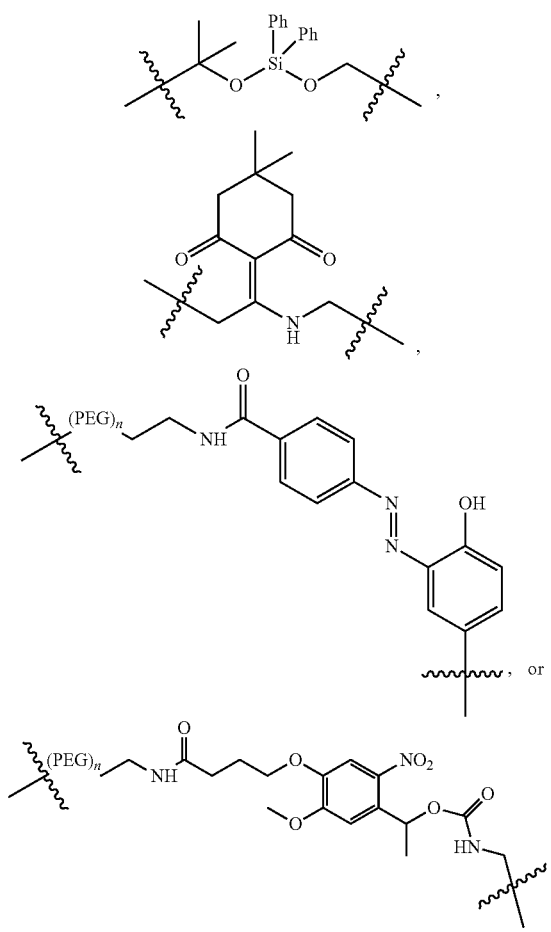

where n is an integer from 1 to 6.

5. The method of claim 1 wherein the tagging reagent comprises a tag having the formula:

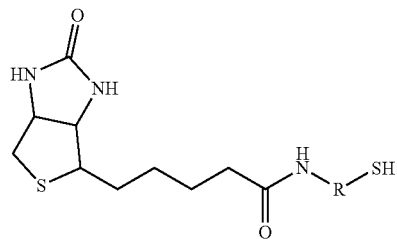

wherein R is selected from the group consisting of substituted and unsubstituted $C_1$ to $C_{24}$ alkyl groups, $C_4$ to $C_{24}$ cycloalkyl groups, $C_2$ to $C_{24}$ alkenyl groups, $C_5$ to $C_{24}$ cycloalkenyl groups, $C_6$ to $C_{24}$ aryl groups and $C_7$ to $C_{24}$ arylalkyl groups.

6. The method of claim 1 wherein the tagging reagent comprises a tag having the formula:

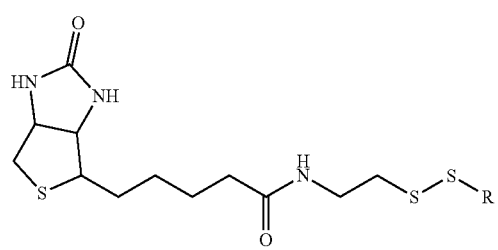

wherein R is selected from the group consisting of substituted and unsubstituted $C_1$ to $C_{24}$ alkyl groups, $C_4$ to $C_{24}$ cycloalkyl groups, $C_2$ to $C_{24}$ alkenyl groups, $C_5$ to $C_{24}$ cycloalkenyl groups, $C_6$ to $C_{24}$ aryl groups, $C_7$ to $C_{24}$ arylalkyl groups, and hydrogen.

7. The method of claim 1 wherein the tagging reagent is:

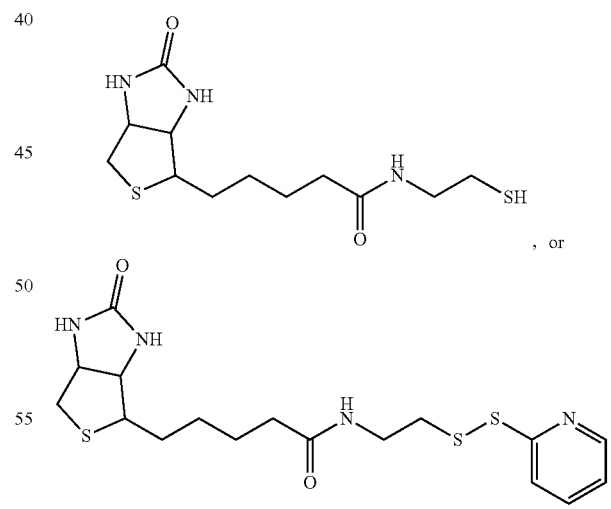

8. The method of claim 1 wherein the tagging reagent is attached to a solid support comprising a resin bead or magnetic bead.

9. The method of claim 1 wherein the tagging reagent is an isotopically enriched tagging reagent comprising one or more heavy isotopes present in an amount in excess of the natural isotopic abundance.

10. The method of claim 9 wherein the tagging reagent has the formula:

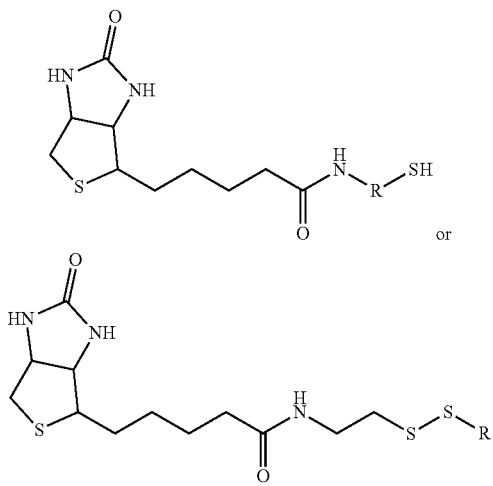

or wherein R is selected from the group consisting of substituted and unsubstituted $C_1$ to $C_{24}$ alkyl groups, $C_4$ to $C_{24}$ cycloalkyl groups, $C_2$ to $C_{24}$ alkenyl groups, $C_5$ to $C_{24}$ cycloalkenyl groups, $C_6$ to $C_{24}$ aryl groups, and $C_7$ to $C_{24}$ arylalkyl groups, wherein any number of carbons in the tagging reagent are $^{12}C$ or $^{13}C$;

wherein any number of nitrogens in the tagging reagent are $^{14}N$ or $^{15}N$;

wherein any number of hydrogens in the tagging reagent are $^{1}H$ or $^{2}H$; and wherein any number of oxygens in the tagging reagent are $^{16}O$ or $^{18}O$.

11. The method of claim 1 further comprising:

e) providing two or more samples containing the target biomolecule;

f) reacting the target biomolecule in each sample with a different isotopically enriched tagging reagent, thereby generating two or more samples comprising different isotopically labeled target biomolecules;

g) combining the different isotopically labeled target biomolecules from the two or more samples and ionizing to form precursor ions; and h) detecting and analyzing precursor ions from each of the two or more samples using a mass spectrometer.

12. The method of claim 11 wherein the different isotopically enriched tagging reagents have molecular weights within 1 Da of each other.

13. The method of claim 1 wherein the region of the polypeptide modified by the PTM comprises a citrulline residue.

14. A method of analyzing a target biomolecule in a sample, said method comprising the steps of:

a) providing a sample containing the target biomolecule, wherein the target biomolecule comprises a polypeptide having a post-translational modification (PTM) comprising a ureido group;

b) reacting the target biomolecule with a tagging reagent to generate a labeled biomolecule, wherein the reacting step comprises adding the tagging reagent with 2,3-butanedione, 2,3-butanedione monoxime, or a phenylglyoxal derivative to the target biomolecule thereby generating a derivatized polypeptide from the polypeptide having the region modified by the PTM comprising the ureido group, wherein the tagging reagent comprises a thiol group or a disulfide group able to react with the derivatized polypeptide, and wherein reacting the tagging reagent with the target biomolecule imparts a mass shift to the target biomolecule;

c) ionizing the labeled biomolecule to form a precursor ion;

d) detecting and analyzing the precursor ion using a mass spectrometer; and e) identifying biomolecules with mass spectrometry data;

wherein the phenylglyoxal derivative has the formula:

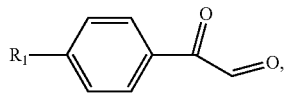

where $R_1$ comprises a thiol group or is functional group able to react with a biotin-thiol tag.

* * * * *

SEQUENCE LISTING

```
<160> NUMBER OF SEQ ID NOS: 21

<210> SEQ ID NO 1
<211> LENGTH: 13
<212> TYPE: PRT
<213> ORGANISM: Artificial sequence
<220> FEATURE:
<223> OTHER INFORMATION: Synthetic construct

<400> SEQUENCE: 1

Ser Ala Val Arg Ala Arg Ser Ser Val Pro Gly Val Arg
1               5                   10

<210> SEQ ID NO 2
<211> LENGTH: 12
<212> TYPE: PRT
<213> ORGANISM: Artificial sequence
<220> FEATURE:
<223> OTHER INFORMATION: Synthetic construct

<400> SEQUENCE: 2

His Arg Asp Thr Gly Ile Leu Asp Ser Ile Gly Arg
1               5                   10

<210> SEQ ID NO 3
<211> LENGTH: 25
<212> TYPE: PRT
<213> ORGANISM: Artificial sequence
<220> FEATURE:
<223> OTHER INFORMATION: Synthetic construct
```

```
<400> SEQUENCE: 3

Ala Val Asp His Ile Asn Ser Arg Ile Ala Pro Ala Leu Ile Ser Ser
1               5                   10                  15

Gly Ile Ser Val Val Glu Gln Glu Lys
            20                  25

<210> SEQ ID NO 4
<211> LENGTH: 8
<212> TYPE: PRT
<213> ORGANISM: Artificial sequence
<220> FEATURE:
<223> OTHER INFORMATION: Synthetic construct

<400> SEQUENCE: 4

Ala Val Asp His Ile Asn Ser Arg
1               5

<210> SEQ ID NO 5
<211> LENGTH: 15
<212> TYPE: PRT
<213> ORGANISM: Artificial sequence
<220> FEATURE:
<223> OTHER INFORMATION: Synthetic construct

<400> SEQUENCE: 5

Tyr Gln Leu Ser Ile His Glu Thr Glu Asp Pro Asn Asp Asn Arg
1               5                   10                  15

<210> SEQ ID NO 6
<211> LENGTH: 21
<212> TYPE: PRT
<213> ORGANISM: Artificial sequence
<220> FEATURE:
<223> OTHER INFORMATION: Synthetic construct

<400> SEQUENCE: 6

Tyr Gln Leu Ser Ile His Glu Thr Glu Asp Pro Asn Asp Asn Arg Tyr
1               5                   10                  15

Leu Leu Val Met Lys
            20

<210> SEQ ID NO 7
<211> LENGTH: 18
<212> TYPE: PRT
<213> ORGANISM: Artificial sequence
<220> FEATURE:
<223> OTHER INFORMATION: Synthetic construct

<400> SEQUENCE: 7

Tyr Leu Ala Thr Ala Ser Thr Met Asp His Ala Arg His Gly Phe Leu
1               5                   10                  15

Pro Arg

<210> SEQ ID NO 8
<211> LENGTH: 14
<212> TYPE: PRT
<213> ORGANISM: Artificial sequence
<220> FEATURE:
<223> OTHER INFORMATION: Synthetic construct

<400> SEQUENCE: 8

Asn Ile Val Thr Pro Arg Thr Pro Pro Pro Ser Gln Gly Lys
1               5                   10
```

```
<210> SEQ ID NO 9
<211> LENGTH: 11
<212> TYPE: PRT
<213> ORGANISM: Artificial sequence
<220> FEATURE:
<223> OTHER INFORMATION: Synthetic construct

<400> SEQUENCE: 9

Thr Val Glu Met Arg Asp Gly Glu Val Ile Lys
1               5                   10

<210> SEQ ID NO 10
<211> LENGTH: 10
<212> TYPE: PRT
<213> ORGANISM: Artificial sequence
<220> FEATURE:
<223> OTHER INFORMATION: Synthetic construct

<400> SEQUENCE: 10

Ala Leu Ala Ala Glu Leu Asn Gln Leu Arg
1               5                   10

<210> SEQ ID NO 11
<211> LENGTH: 11
<212> TYPE: PRT
<213> ORGANISM: Artificial sequence
<220> FEATURE:
<223> OTHER INFORMATION: Synthetic construct

<400> SEQUENCE: 11

Gly Arg Leu Glu Glu Val Gly Asn Gln Ala Arg
1               5                   10

<210> SEQ ID NO 12
<211> LENGTH: 15
<212> TYPE: PRT
<213> ORGANISM: Artificial sequence
<220> FEATURE:
<223> OTHER INFORMATION: Synthetic construct

<400> SEQUENCE: 12

Thr Ala Asn Leu Gly Ala Gly Ala Ala Gln Pro Leu Arg Asp Arg
1               5                   10                  15

<210> SEQ ID NO 13
<211> LENGTH: 14
<212> TYPE: PRT
<213> ORGANISM: Artificial sequence
<220> FEATURE:
<223> OTHER INFORMATION: Synthetic construct

<400> SEQUENCE: 13

Ser Arg Leu Gln Thr Ala Pro Val Pro Met Pro Asp Leu Lys
1               5                   10

<210> SEQ ID NO 14
<211> LENGTH: 21
<212> TYPE: PRT
<213> ORGANISM: Artificial sequence
<220> FEATURE:
<223> OTHER INFORMATION: Synthetic construct

<400> SEQUENCE: 14

Thr Asp His Gly Ala Glu Ile Val Tyr Lys Ser Pro Val Val Ser Gly
1               5                   10                  15

Asp Thr Ser Pro Arg
            20
```

```
<210> SEQ ID NO 15
<211> LENGTH: 15
<212> TYPE: PRT
<213> ORGANISM: Artificial sequence
<220> FEATURE:
<223> OTHER INFORMATION: Synthetic construct

<400> SEQUENCE: 15

Asn Leu Phe Thr Gln Thr Leu Gly Leu Gly Ser Gln Lys Glu Arg
1               5                   10                  15

<210> SEQ ID NO 16
<211> LENGTH: 17
<212> TYPE: PRT
<213> ORGANISM: Artificial sequence
<220> FEATURE:
<223> OTHER INFORMATION: Synthetic construct

<400> SEQUENCE: 16

Glu Leu Tyr Pro Gly Gln Phe Lys Pro Thr Ile Cys His Tyr Phe Ile
1               5                   10                  15

Arg

<210> SEQ ID NO 17
<211> LENGTH: 12
<212> TYPE: PRT
<213> ORGANISM: Artificial sequence
<220> FEATURE:
<223> OTHER INFORMATION: Synthetic construct

<400> SEQUENCE: 17

Asp Ala Val Thr Tyr Thr Glu His Ala Lys Arg Lys
1               5                   10

<210> SEQ ID NO 18
<211> LENGTH: 19
<212> TYPE: PRT
<213> ORGANISM: Artificial sequence
<220> FEATURE:
<223> OTHER INFORMATION: Synthetic construct

<400> SEQUENCE: 18

His Gly Val Tyr Asn Pro Asn Lys Ile Phe Gly Val Thr Thr Leu Asp
1               5                   10                  15

Ile Val Arg

<210> SEQ ID NO 19
<211> LENGTH: 14
<212> TYPE: PRT
<213> ORGANISM: Artificial sequence
<220> FEATURE:
<223> OTHER INFORMATION: Synthetic construct

<400> SEQUENCE: 19

Ser Thr Gly Gly Lys Ala Pro Arg Lys Gln Leu Ala Thr Lys
1               5                   10
```

```
<210> SEQ ID NO 20
<211> LENGTH: 8
<212> TYPE: PRT
<213> ORGANISM: Artificial sequence
<220> FEATURE:
<223> OTHER INFORMATION: Synthetic construct

<400> SEQUENCE: 20

Ser Thr Gly Gly Lys Ala Pro Arg
1               5

<210> SEQ ID NO 21
<211> LENGTH: 136
<212> TYPE: PRT
<213> ORGANISM: Artificial sequence
<220> FEATURE:
<223> OTHER INFORMATION: Synthetic construct

<400> SEQUENCE: 21

Met Ala Arg Thr Lys Gln Thr Ala Arg Lys Ser Thr Gly Gly Lys Ala
1               5                   10                  15

Pro Arg Lys Gln Leu Ala Thr Lys Ala Ala Arg Lys Ser Ala Pro Ala
                20                  25                  30

Thr Gly Gly Val Lys Lys Pro His Arg Tyr Arg Pro Gly Thr Val Ala
            35                  40                  45

Leu Arg Glu Ile Arg Arg Tyr Gln Lys Ser Thr Glu Leu Leu Ile Arg
        50                  55                  60

Lys Leu Pro Phe Gln Arg Leu Val Arg Glu Ile Ala Gln Asp Phe Lys
65                  70                  75                  80

Thr Asp Leu Arg Phe Gln Ser Ser Ala Val Met Ala Leu Gln Glu Ala
                85                  90                  95

Cys Glu Ala Tyr Leu Val Gly Leu Phe Glu Asp Thr Asn Leu Cys Ala
            100                 105                 110

Ile His Ala Lys Arg Val Thr Ile Met Pro Lys Asp Ile Gln Leu Ala
        115                 120                 125

Arg Arg Ile Arg Gly Glu Arg Ala
        130                 135
```